(12) United States Patent
Chang et al.

(10) Patent No.: US 7,297,679 B2
(45) Date of Patent: *Nov. 20, 2007

(54) CYCLOSPORIN COMPOSITIONS

(75) Inventors: James N. Chang, Newport Beach, CA (US); Orest Olejnik, Coto De Caza, CA (US); Bruce A. Firestone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 11/181,178

(22) Filed: Jul. 13, 2005

(65) Prior Publication Data

US 2007/0015690 A1  Jan. 18, 2007

(51) Int. Cl.
*A61K 38/12* (2006.01)

(52) U.S. Cl. .................. 514/9; 530/317; 514/912; 514/975

(58) Field of Classification Search ............... None
See application file for complete search history.

(56) References Cited

U.S. PATENT DOCUMENTS

| | | | |
|---|---|---|---|
| 4,388,307 A | 6/1983 | Cavanak | |
| 4,649,047 A | 3/1987 | Kaswan | |
| 4,814,323 A | 3/1989 | Andrieu et al. | |
| 4,839,342 A | 6/1989 | Kaswan | |
| 4,996,193 A | 2/1991 | Hewitt et al. | |
| 5,047,396 A | 9/1991 | Orban et al. | |
| 5,051,402 A | 9/1991 | Kurihara et al. | |
| 5,342,625 A | 8/1994 | Hauer et al. | |
| 5,474,979 A | 12/1995 | Ding et al. | |
| 5,543,393 A | 8/1996 | Kim et al. | |
| 5,614,491 A | 3/1997 | Walch et al. | |
| 5,639,724 A | 6/1997 | Cavanak | |
| 5,652,212 A | 7/1997 | Cavanak et al. | |
| 5,759,997 A | 6/1998 | Cavanak | |
| 5,766,629 A | 6/1998 | Cho et al. | |
| 5,798,333 A | 8/1998 | Sherman | |
| 5,827,822 A | 10/1998 | Floc'h et al. | |
| 5,834,017 A | 11/1998 | Cho et al. | |
| 5,891,846 A | 4/1999 | Ishida et al. | |
| 5,916,589 A | 6/1999 | Hauer et al. | |
| 5,951,971 A | 9/1999 | Kawashima et al. | |
| 5,962,014 A | 10/1999 | Hauer et al. | |
| 5,962,017 A | 10/1999 | Hauer et al. | |
| 5,962,019 A | 10/1999 | Cho et al. | |
| 5,977,066 A | 11/1999 | Cavanak | |
| 6,007,840 A | 12/1999 | Hauer et al. | |
| 6,024,978 A | 2/2000 | Hauer et al. | |
| 6,057,289 A | 5/2000 | Mulye | |
| 6,197,335 B1 | 3/2001 | Sherman | |
| 6,254,860 B1 | 7/2001 | Garst | |
| 6,254,885 B1 | 7/2001 | Cho et al. | |
| 6,267,985 B1 * | 7/2001 | Chen et al. | 424/455 |
| 6,284,268 B1 | 9/2001 | Mishra et al. | |
| 6,294,192 B1 | 9/2001 | Patel et al. | |
| 6,306,825 B1 | 10/2001 | Cavanak | |
| 6,350,442 B2 | 2/2002 | Garst | |
| 6,468,968 B2 | 10/2002 | Cavanak et al. | |
| 6,475,519 B1 | 11/2002 | Meinzer et al. | |
| 6,486,124 B2 | 11/2002 | Olbrich et al. | |
| 6,569,463 B2 | 5/2003 | Patel et al. | |
| 6,582,718 B2 | 6/2003 | Kawashima et al. | |
| 6,638,522 B1 | 10/2003 | Mulye | |
| 6,656,504 B1 | 12/2003 | Bosch et al. | |
| 6,723,339 B2 | 4/2004 | Meinzer et al. | |
| 6,916,785 B2 | 7/2005 | Patel | |
| 2001/0003589 A1 | 6/2001 | Neuer et al. | |
| 2001/0036449 A1 | 11/2001 | Garst | |
| 2002/0012680 A1 | 1/2002 | Patel et al. | |
| 2002/0013272 A1 | 1/2002 | Cavanak et al. | |
| 2002/0016290 A1 | 2/2002 | Floc'h et al. | |
| 2002/0016292 A1 | 2/2002 | Richter et al. | |
| 2002/0025927 A1 | 2/2002 | Olbrich et al. | |
| 2002/0045601 A1 | 4/2002 | Kawashima et al. | |
| 2002/0107183 A1 | 8/2002 | Petszulat et al. | |
| 2002/0119190 A1 | 8/2002 | Meinzer et al. | |
| 2002/0165134 A1 | 11/2002 | Richter et al. | |
| 2003/0060402 A1 | 3/2003 | Cavanak et al. | |
| 2003/0133984 A1 | 7/2003 | Ambuhl et al. | |
| 2003/0143250 A1 | 7/2003 | Hauer et al. | |
| 2003/0147954 A1 | 8/2003 | Yang et al. | |
| 2003/0166517 A1 | 9/2003 | Fricker et al. | |
| 2003/0211983 A1 | 11/2003 | Petszulat et al. | |
| 2003/0215496 A1 | 11/2003 | Patel et al. | |

(Continued)

FOREIGN PATENT DOCUMENTS

EP  0471293  2/1992

(Continued)

OTHER PUBLICATIONS

Kuwano, et al., Pharmaceutical Research, 2002, 19, 108-111.*

(Continued)

*Primary Examiner*—Anish Gupta
*Assistant Examiner*—Satyanarayana R. Gudibande
(74) *Attorney, Agent, or Firm*—Brent A. Johnson; Martin A. Voet

(57) ABSTRACT

A composition comprising from about 0.001% to about 0.4% cyclosporin A, a surfactant, and an oil having a specific gravity from 0.8 to 0.95 is disclosed herein.

3 Claims, No Drawings

U.S. PATENT DOCUMENTS

| | | |
|---|---|---|
| 2004/0048789 A1 | 3/2004 | Patel |
| 2004/0101552 A1 | 5/2004 | Patel |
| 2004/0102366 A1 | 5/2004 | Patel |
| 2004/0161458 A1 | 8/2004 | Meinzer et al. |
| 2004/0167063 A1 | 8/2004 | Cavanak et al. |
| 2004/0198645 A1 | 10/2004 | Ambuhl et al. |
| 2005/0048087 A1 | 3/2005 | Posanski |
| 2005/0059583 A1 | 3/2005 | Acheampong et al. |
| 2005/0118254 A1 | 6/2005 | Choi et al. |
| 2005/0129718 A1 | 6/2005 | Sherman |
| 2005/0147659 A1 | 7/2005 | Carli et al. |

FOREIGN PATENT DOCUMENTS

| | | |
|---|---|---|
| WO | WO 00/00179 | 1/2000 |

OTHER PUBLICATIONS

Kuwano, 2002, Pharmaceutical Research, 19, 108-111.*
Kuwano et al, "Cyclosporine A Formulation Affects Its Ocular Distribution in Rabbits", Pharmaceutical Research, vol. 19, No. 1, Jan. 2002, 108-111.

* cited by examiner

CYCLOSPORIN COMPOSITIONS

BACKGROUND

Description of the Relevant Art

Cyclosporins are a group of nonpolar cyclic oligopeptides with known immunosuppressant activity. In addition, as set forth in U.S. Pat. No. 4,839,342, cyclosporin (sometimes referred to in the literature as "cyclosporine") has been found as effective in treating immune medicated keratoconjunctivitis sicca (KCS or dry eye disease) in a patient suffering therefrom.

As hereinabove noted, cyclosporin comprises a group of cyclic oligopeptides and the major component thereof is cyclosporin A ($C_{62}H_{111}N_{11}O_{12}$) which has been identified along with several other minor metabolites, cyclosporin B through I. In addition, a number of synthetic analogs have been prepared.

In general, commercially available cyclosporins may contain a mixture of several individual cyclosporins which all share a cyclic peptide structure consisting of eleven amino acid residues with a total molecular weight of about 1,200, but with different substituents or configurations of some of the amino acids.

The activity of cyclosporins, as hereinabove noted, is as an immunosuppressant and in the enhancement or restoring of lacrimal gland tearing.

Unfortunately, the solubility of cyclosporin in water is extremely low and as elaborated in U.S. Pat. No. 5,051,402, it has been considered not merely difficult but practically impossible to prepare a pharmaceutical composition containing cyclosporin dissolved in an aqueous medium.

As reported, the solubility of cyclosporin in water is between about 20 µg/ml to 30 µg/ml for cyclosporin A. Hence, heretofore prepared formulations incorporating cyclosporin have been prepared as oily solutions containing ethanol. However, these preparations limit the bioavailability to oral preparations and this is believed to be due to the separation of cyclosporin as a solid immediately after it comes into contact with water, such as in the mouth or eye of a patient.

Surface active agents such as polyoxyethylated castor oil have been utilized as solubilizers to inject preparations in order to prevent cyclosporin from separating. However, this also may give rise to safety problems (see U.S. Pat. No. 5,051,402).

U.S. Pat. No. 5,474,979 discloses a pharmaceutical composition in the form of a nonirritating emulsion which includes at least one cyclosporin in admixture with a higher fatty acid glyceride and polysorbate 80. More particularly, the cyclosporin may be cyclosporin A and the higher fatty acid glyceride may be castor oil.

U.S. Pat. No. 6,582,718 discloses an ophthalmic composition particularly in the form of eye-drops suitable for the treatment of diseases of the eye and surrounding areas. The composition contains a cyclosporin and a surfactant selected from polyoxyethylene fatty acid esters, polyoxyethylene alkylphenyl ethers and polyoxyethylene alkyl ethers, or mixtures thereof.

Copending U.S. Patent Application No. 60/503,137, filed Sep. 15, 2003, and U.S. patent application Ser. No. 10/865,638, filed Jun. 9, 2004 also disclose compositions of interest.

DESCRIPTION OF THE INVENTION

A composition comprising from about 0.001% to about 0.4% cyclosporin A, a surfactant, and an oil having a specific gravity from 0.8 to 0.95 is disclosed herein.

Another embodiment is a composition wherein said oil has a specific gravity of from 0.90 to 0.95.

Another embodiment is a composition comprising from about 0.005% to about 0.05% cyclosporin A.

Another embodiment is a composition comprising about 0.05% cyclosporin A.

While not intending to limit the scope of the invention in any way, the following are examples of oils with a specific gravity of from 0.90 to 0.95: almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalpytus oil, and sesame oil.

While not intending to limit the scope of the invention in any way, the following are examples of oils with a specific gravity below 0.9: mineral oil, coriander oil, lavender oil, citronella oil, juniper oil, lemon oil, orange oil, clary sage oil, nutmeg oil, and tea tree oil.

While not intending to limit the scope of the invention in any way, one type of useful surfactant is a sorbitan ester. Examples include, but are not limited to, Polysorbate 20, Polysorbate 40, Polysorbate 60, and Polysorbate 80.

While not intending to limit the scope of the invention in any way, another type of useful surfactant is a stearate. Examples include, but are not limited to, glyceryl stearate, isopropyl stearate, polyoxyl stearate, propylene glycol stearate, and sucrose stearate.

While not intending to limit the scope of the invention in any way, another useful surfactant is polyethylene glycol.

While not intending to limit the scope of the invention in any way. Other useful surfactants comprise polyethylene oxide or polypropylene oxide. Examples, include, but are not limited to, polyethylene oxides, polypropylene oxides, polyethylene oxide, polypropylene oxide copolymers, alcohol ethoxylates, and alkylphenol ethoxylates.

While not intending to limit the scope of the invention in any way, another useful type of surfactant is alkyl glycosides.

While not intending to limit the scope of the invention in any way, another useful type of surfactant is alkyl polyglycosides While not intending to limit the scope of the invention in any way, another useful type of surfactant is fatty alcohols.

While not intending to limit the scope of the invention in any way, another useful type of surfactant is cellulose derivatives, including, but not limited to, hydroxypropylmethyl cellulose (HPMC) and carboxymethyl cellulose (CMC).

While not intending to limit the scope of the invention in any way, another useful type of surfactant is polyacrylic acids, including, but not limited to, Carbomers.

While not intending to limit the scope of the invention in any way, another useful type of surfactant is phospholipids, including, but not limited to, phosphatidyl chloline and phosphatidyl serine.

Another embodiment comprises cyclosporin A, a sorbitan ester, and an oil having a specific gravity between 0.90 and 0.95.

Another embodiment comprises cyclosporin A, a sorbitan ester, and almond oil.

Another embodiment comprises cyclosporin A, a sorbitan ester, and corn oil.

Another embodiment comprises cyclosporin A, a sorbitan ester, and arachis oil.

Another embodiment comprises cyclosporin A, a sorbitan ester, and cottonseed oil.

Another embodiment comprises cyclosporin A, a sorbitan ester, and safflower oil.

Another embodiment comprises cyclosporin A, a sorbitan ester, and maize oil.

Another embodiment comprises cyclosporin A, a sorbitan ester, and linseed oil.

Another embodiment comprises cyclosporin A, a sorbitan ester, and rapeseed oil.

Another embodiment comprises cyclosporin A, a sorbitan ester, and soybean oil.

Another embodiment comprises cyclosporin A, a sorbitan ester, and olive oil.

Another embodiment comprises cyclosporin A, a sorbitan ester, and caraway oil.

Another embodiment comprises cyclosporin A, a sorbitan ester, and rosemary oil.

Another embodiment comprises cyclosporin A, a sorbitan ester, and peanut oil.

Another embodiment comprises cyclosporin A, a sorbitan ester, and peppermint oil.

Another embodiment comprises cyclosporin A, a sorbitan ester, and sunflower oil.

Another embodiment comprises cyclosporin A, a sorbitan ester, and eucalpytus oil.

Another embodiment comprises cyclosporin A, a sorbitan ester, and sesame oil.

Another embodiment comprises cyclosporin A, a sorbitan ester, and an oil having a specific gravity below 0.9.

Another embodiment comprises cyclosporin A, a sorbitan ester, and mineral oil.

Another embodiment comprises cyclosporin A, a sorbitan ester, and coriander oil.

Another embodiment comprises cyclosporin A, a sorbitan ester, and lavender oil.

Another embodiment comprises cyclosporin A, a sorbitan ester, and citronella oil.

Another embodiment comprises cyclosporin A, a sorbitan ester, and juniper oil.

Another embodiment comprises cyclosporin A, a sorbitan ester, and lemon oil.

Another embodiment comprises cyclosporin A, a sorbitan ester, and orange oil.

Another embodiment comprises cyclosporin A, a sorbitan ester, and clary sage oil.

Another embodiment comprises cyclosporin A, a sorbitan ester, and nutmeg oil.

Another embodiment comprises cyclosporin A, a sorbitan ester, and tea tree oil.

Another embodiment comprises cyclosporin A, Polysorbate 20, and an oil having a specific gravity between 0.90 and 0.95.

Another embodiment comprises cyclosporin A, Polysorbate 20, and almond oil.

Another embodiment comprises cyclosporin A, Polysorbate 20, and corn oil.

Another embodiment comprises cyclosporin A, Polysorbate 20, and arachis oil.

Another embodiment comprises cyclosporin A, Polysorbate 20, and cottonseed oil.

Another embodiment comprises cyclosporin A, Polysorbate 20, and safflower oil.

Another embodiment comprises cyclosporin A, Polysorbate 20, and maize oil.

Another embodiment comprises cyclosporin A, Polysorbate 20, and linseed oil.

Another embodiment comprises cyclosporin A, Polysorbate 20, and rapeseed oil.

Another embodiment comprises cyclosporin A, Polysorbate 20, and soybean oil.

Another embodiment comprises cyclosporin A, Polysorbate 20, and olive oil.

Another embodiment comprises cyclosporin A, Polysorbate 20, and caraway oil.

Another embodiment comprises cyclosporin A, Polysorbate 20, and rosemary oil.

Another embodiment comprises cyclosporin A, Polysorbate 20, and peanut oil.

Another embodiment comprises cyclosporin A, Polysorbate 20, and peppermint oil.

Another embodiment comprises cyclosporin A, Polysorbate 20, and sunflower oil.

Another embodiment comprises cyclosporin A, Polysorbate 20, and eucalpytus oil.

Another embodiment comprises cyclosporin A, Polysorbate 20, and sesame oil.

Another embodiment comprises cyclosporin A, Polysorbate 20, and an oil having a specific gravity below 0.9.

Another embodiment comprises cyclosporin A, Polysorbate 20, and mineral oil.

Another embodiment comprises cyclosporin A, Polysorbate 20, and coriander oil.

Another embodiment comprises cyclosporin A, Polysorbate 20, and lavender oil.

Another embodiment comprises cyclosporin A, Polysorbate 20, and citronella oil.

Another embodiment comprises cyclosporin A, Polysorbate 20, and juniper oil.

Another embodiment comprises cyclosporin A, Polysorbate 20, and lemon oil.

Another embodiment comprises cyclosporin A, Polysorbate 20, and orange oil.

Another embodiment comprises cyclosporin A, Polysorbate 20, and clary sage oil.

Another embodiment comprises cyclosporin A, Polysorbate 20, and nutmeg oil.

Another embodiment comprises cyclosporin A, Polysorbate 20, and tea tree oil.

Another embodiment comprises cyclosporin A, Polysorbate 40, and an oil having a specific gravity between 0.90 and 0.95.

Another embodiment comprises cyclosporin A, Polysorbate 40, and almond oil.

Another embodiment comprises cyclosporin A, Polysorbate 40, and corn oil.

Another embodiment comprises cyclosporin A, Polysorbate 40, and arachis oil.

Another embodiment comprises cyclosporin A, Polysorbate 40, and cottonseed oil.

Another embodiment comprises cyclosporin A, Polysorbate 40, and safflower oil.

Another embodiment comprises cyclosporin A, Polysorbate 40, and maize oil.

Another embodiment comprises cyclosporin A, Polysorbate 40, and linseed oil.

Another embodiment comprises cyclosporin A, Polysorbate 40, and rapeseed oil.

Another embodiment comprises cyclosporin A, Polysorbate 40, and soybean oil.

Another embodiment comprises cyclosporin A, Polysorbate 40, and olive oil.

Another embodiment comprises cyclosporin A, Polysorbate 40, and caraway oil.
Another embodiment comprises cyclosporin A, Polysorbate 40, and rosemary oil.
Another embodiment comprises cyclosporin A, Polysorbate 40, and peanut oil.
Another embodiment comprises cyclosporin A, Polysorbate 40, and peppermint oil.
Another embodiment comprises cyclosporin A, Polysorbate 40, and sunflower oil.
Another embodiment comprises cyclosporin A, Polysorbate 40, and eucalpytus oil.
Another embodiment comprises cyclosporin A, Polysorbate 40, and sesame oil.
Another embodiment comprises cyclosporin A, Polysorbate 40, and an oil having a specific gravity below 0.9.
Another embodiment comprises cyclosporin A, Polysorbate 40, and mineral oil.
Another embodiment comprises cyclosporin A, Polysorbate 40, and coriander oil.
Another embodiment comprises cyclosporin A, Polysorbate 40, and lavender oil.
Another embodiment comprises cyclosporin A, Polysorbate 40, and citronella oil.
Another embodiment comprises cyclosporin A, Polysorbate 40, and juniper oil.
Another embodiment comprises cyclosporin A, Polysorbate 40, and lemon oil.
Another embodiment comprises cyclosporin A, Polysorbate 40, and orange oil.
Another embodiment comprises cyclosporin A, Polysorbate 40, and clary sage oil.
Another embodiment comprises cyclosporin A, Polysorbate 40, and nutmeg oil.
Another embodiment comprises cyclosporin A, Polysorbate 40, and tea tree oil.
Another embodiment comprises cyclosporin A, Polysorbate 60, and an oil having a specific gravity between 0.90 and 0.95.
Another embodiment comprises cyclosporin A, Polysorbate 60, and almond oil.
Another embodiment comprises cyclosporin A, Polysorbate 60, and corn oil.
Another embodiment comprises cyclosporin A, Polysorbate 60, and arachis oil.
Another embodiment comprises cyclosporin A, Polysorbate 60, and cottonseed oil.
Another embodiment comprises cyclosporin A, Polysorbate 60, and safflower oil.
Another embodiment comprises cyclosporin A, Polysorbate 60, and maize oil.
Another embodiment comprises cyclosporin A, Polysorbate 60, and linseed oil.
Another embodiment comprises cyclosporin A, Polysorbate 60, and rapeseed oil.
Another embodiment comprises cyclosporin A, Polysorbate 60, and soybean oil.
Another embodiment comprises cyclosporin A, Polysorbate 60, and olive oil.
Another embodiment comprises cyclosporin A, Polysorbate 60, and caraway oil.
Another embodiment comprises cyclosporin A, Polysorbate 60, and rosemary oil.
Another embodiment comprises cyclosporin A, Polysorbate 60, and peanut oil.
Another embodiment comprises cyclosporin A, Polysorbate 60, and peppermint oil.
Another embodiment comprises cyclosporin A, Polysorbate 60, and sunflower oil.
Another embodiment comprises cyclosporin A, Polysorbate 60, and eucalpytus oil.
Another embodiment comprises cyclosporin A, Polysorbate 60, and sesame oil.
Another embodiment comprises cyclosporin A, Polysorbate 60, and an oil having a specific gravity below 0.9.
Another embodiment comprises cyclosporin A, Polysorbate 60, and mineral oil.
Another embodiment comprises cyclosporin A, Polysorbate 60, and coriander oil.
Another embodiment comprises cyclosporin A, Polysorbate 60, and lavender oil.
Another embodiment comprises cyclosporin A, Polysorbate 60, and citronella oil.
Another embodiment comprises cyclosporin A, Polysorbate 60, and juniper oil.
Another embodiment comprises cyclosporin A, Polysorbate 60, and lemon oil.
Another embodiment comprises cyclosporin A, Polysorbate 60, and orange oil.
Another embodiment comprises cyclosporin A, Polysorbate 60, and clary sage oil.
Another embodiment comprises cyclosporin A, Polysorbate 60, and nutmeg oil.
Another embodiment comprises cyclosporin A, Polysorbate 60, and tea tree oil.
Another embodiment comprises cyclosporin A, Polysorbate 80, and an oil having a specific gravity between 0.90 and 0.95.
Another embodiment comprises cyclosporin A, Polysorbate 80, and almond oil.
Another embodiment comprises cyclosporin A, Polysorbate 80, and corn oil.
Another embodiment comprises cyclosporin A, Polysorbate 80, and arachis oil.
Another embodiment comprises cyclosporin A, Polysorbate 80, and cottonseed oil.
Another embodiment comprises cyclosporin A, Polysorbate 80, and safflower oil.
Another embodiment comprises cyclosporin A, Polysorbate 80, and maize oil.
Another embodiment comprises cyclosporin A, Polysorbate 80, and linseed oil.
Another embodiment comprises cyclosporin A, Polysorbate 80, and rapeseed oil.
Another embodiment comprises cyclosporin A, Polysorbate 80, and soybean oil.
Another embodiment comprises cyclosporin A, Polysorbate 80, and olive oil.
Another embodiment comprises cyclosporin A, Polysorbate 80, and caraway oil.
Another embodiment comprises cyclosporin A, Polysorbate 80, and rosemary oil.
Another embodiment comprises cyclosporin A, Polysorbate 80, and peanut oil.
Another embodiment comprises cyclosporin A, Polysorbate 80, and peppermint oil.
Another embodiment comprises cyclosporin A, Polysorbate 80, and sunflower oil.
Another embodiment comprises cyclosporin A, Polysorbate 80, and eucalpytus oil.
Another embodiment comprises cyclosporin A, Polysorbate 80, and sesame oil.
Another embodiment comprises cyclosporin A, Polysorbate 80, and an oil having a specific gravity below 0.9.

Another embodiment comprises cyclosporin A, Polysorbate 80, and mineral oil.
Another embodiment comprises cyclosporin A, Polysorbate 80, and coriander oil.
Another embodiment comprises cyclosporin A, Polysorbate 80, and lavender oil.
Another embodiment comprises cyclosporin A, Polysorbate 80, and citronella oil.
Another embodiment comprises cyclosporin A, Polysorbate 80, and juniper oil.
Another embodiment comprises cyclosporin A, Polysorbate 80, and lemon oil.
Another embodiment comprises cyclosporin A, Polysorbate 80, and orange oil.
Another embodiment comprises cyclosporin A, Polysorbate 80, and clary sage oil.
Another embodiment comprises cyclosporin A, Polysorbate 80, and nutmeg oil.
Another embodiment comprises cyclosporin A, Polysorbate 80, and tea tree oil.
Another embodiment comprises cyclosporin A, a stearate, and an oil having a specific gravity between 0.90 and 0.95.
Another embodiment comprises cyclosporin A, a stearate, and almond oil.
Another embodiment comprises cyclosporin A, a stearate, and corn oil.
Another embodiment comprises cyclosporin A, a stearate, and arachis oil.
Another embodiment comprises cyclosporin A, a stearate, and cottonseed oil.
Another embodiment comprises cyclosporin A, a stearate, and safflower oil.
Another embodiment comprises cyclosporin A, a stearate, and maize oil.
Another embodiment comprises cyclosporin A, a stearate, and linseed oil.
Another embodiment comprises cyclosporin A, a stearate, and rapeseed oil.
Another embodiment comprises cyclosporin A, a stearate, and soybean oil.
Another embodiment comprises cyclosporin A, a stearate, and olive oil.
Another embodiment comprises cyclosporin A, a stearate, and caraway oil.
Another embodiment comprises cyclosporin A, a stearate, and rosemary oil.
Another embodiment comprises cyclosporin A, a stearate, and peanut oil.
Another embodiment comprises cyclosporin A, a stearate, and peppermint oil.
Another embodiment comprises cyclosporin A, a stearate, and sunflower oil.
Another embodiment comprises cyclosporin A, a stearate, and eucalpytus oil.
Another embodiment comprises cyclosporin A, a stearate, and sesame oil.
Another embodiment comprises cyclosporin A, a stearate, and an oil having a specific gravity below 0.9.
Another embodiment comprises cyclosporin A, a stearate, and mineral oil.
Another embodiment comprises cyclosporin A, a stearate, and coriander oil.
Another embodiment comprises cyclosporin A, a stearate, and lavender oil.
Another embodiment comprises cyclosporin A, a stearate, and citronella oil.
Another embodiment comprises cyclosporin A, a stearate, and juniper oil.
Another embodiment comprises cyclosporin A, a stearate, and lemon oil.
Another embodiment comprises cyclosporin A, a stearate, and orange oil.
Another embodiment comprises cyclosporin A, a stearate, and clary sage oil.
Another embodiment comprises cyclosporin A, a stearate, and nutmeg oil.
Another embodiment comprises cyclosporin A, a stearate, and tea tree oil.
Another embodiment comprises cyclosporin A, glyceryl stearate, and an oil having a specific gravity between 0.90 and 0.95.
Another embodiment comprises cyclosporin A, glyceryl stearate, and almond oil.
Another embodiment comprises cyclosporin A, glyceryl stearate, and corn oil.
Another embodiment comprises cyclosporin A, glyceryl stearate, and arachis oil.
Another embodiment comprises cyclosporin A, glyceryl stearate, and cottonseed oil.
Another embodiment comprises cyclosporin A, glyceryl stearate, and safflower oil.
Another embodiment comprises cyclosporin A, glyceryl stearate, and maize oil.
Another embodiment comprises cyclosporin A, glyceryl stearate, and linseed oil.
Another embodiment comprises cyclosporin A, glyceryl stearate, and rapeseed oil.
Another embodiment comprises cyclosporin A, glyceryl stearate, and soybean oil.
Another embodiment comprises cyclosporin A, glyceryl stearate, and olive oil.
Another embodiment comprises cyclosporin A, glyceryl stearate, and caraway oil.
Another embodiment comprises cyclosporin A, glyceryl stearate, and rosemary oil.
Another embodiment comprises cyclosporin A, glyceryl stearate, and peanut oil.
Another embodiment comprises cyclosporin A, glyceryl stearate, and peppermint oil.
Another embodiment comprises cyclosporin A, glyceryl stearate, and sunflower oil.
Another embodiment comprises cyclosporin A, glyceryl stearate, and eucalpytus oil.
Another embodiment comprises cyclosporin A, glyceryl stearate, and sesame oil.
Another embodiment comprises cyclosporin A, glyceryl stearate, and an oil having a specific gravity below 0.9.
Another embodiment comprises cyclosporin A, glyceryl stearate, and mineral oil.
Another embodiment comprises cyclosporin A, glyceryl stearate, and coriander oil.
Another embodiment comprises cyclosporin A, glyceryl stearate, and lavender oil.
Another embodiment comprises cyclosporin A, glyceryl stearate, and citronella oil.
Another embodiment comprises cyclosporin A, glyceryl stearate, and juniper oil.
Another embodiment comprises cyclosporin A, glyceryl stearate, and lemon oil.
Another embodiment comprises cyclosporin A, glyceryl stearate, and orange oil.
Another embodiment comprises cyclosporin A, glyceryl stearate, Another embodiment comprises cyclosporin A, glyceryl stearate, and nutmeg oil.

Another embodiment comprises cyclosporin A, glyceryl stearate, and tea tree oil.

Another embodiment comprises cyclosporin A, isopropyl stearate, and an oil having a specific gravity between 0.90 and 0.95.

Another embodiment comprises cyclosporin A, isopropyl stearate, and almond oil.

Another embodiment comprises cyclosporin A, isopropyl stearate, and corn oil.

Another embodiment comprises cyclosporin A, isopropyl stearate, and arachis oil.

Another embodiment comprises cyclosporin A, isopropyl stearate, and cottonseed oil.

Another embodiment comprises cyclosporin A, isopropyl stearate, and safflower oil.

Another embodiment comprises cyclosporin A, isopropyl stearate, and maize oil.

Another embodiment comprises cyclosporin A, isopropyl stearate, and linseed oil.

Another embodiment comprises cyclosporin A, isopropyl stearate, and rapeseed oil.

Another embodiment comprises cyclosporin A, isopropyl stearate, and soybean oil.

Another embodiment comprises cyclosporin A, isopropyl stearate, and olive oil.

Another embodiment comprises cyclosporin A, isopropyl stearate, and caraway oil.

Another embodiment comprises cyclosporin A, isopropyl stearate, and rosemary oil.

Another embodiment comprises cyclosporin A, isopropyl stearate, and peanut oil.

Another embodiment comprises cyclosporin A, isopropyl stearate, and peppermint oil.

Another embodiment comprises cyclosporin A, isopropyl stearate, and sunflower oil.

Another embodiment comprises cyclosporin A, isopropyl stearate, and eucalpytus oil.

Another embodiment comprises cyclosporin A, isopropyl stearate, and sesame oil.

Another embodiment comprises cyclosporin A, isopropyl stearate, and an oil having a specific gravity below 0.9.

Another embodiment comprises cyclosporin A, isopropyl stearate, and mineral oil.

Another embodiment comprises cyclosporin A, isopropyl stearate, and coriander oil.

Another embodiment comprises cyclosporin A, isopropyl stearate, and lavender oil.

Another embodiment comprises cyclosporin A, isopropyl stearate, and citronella oil.

Another embodiment comprises cyclosporin A, isopropyl stearate, and juniper oil.

Another embodiment comprises cyclosporin A, isopropyl stearate, and lemon oil.

Another embodiment comprises cyclosporin A, isopropyl stearate, and orange oil.

Another embodiment comprises cyclosporin A, isopropyl stearate, and clary sage oil.

Another embodiment comprises cyclosporin A, isopropyl stearate, and nutmeg oil.

Another embodiment comprises cyclosporin A, isopropyl stearate, and tea tree oil.

Another embodiment comprises cyclosporin A, polyoxyl stearate, and an oil having a specific gravity between 0.90 and 0.95.

Another embodiment comprises cyclosporin A, polyoxyl stearate, and almond oil.

Another embodiment comprises cyclosporin A, polyoxyl stearate, and corn oil.

Another embodiment comprises cyclosporin A, polyoxyl stearate, and arachis oil.

Another embodiment comprises cyclosporin A, polyoxyl stearate, and cottonseed oil.

Another embodiment comprises cyclosporin A, polyoxyl stearate, and safflower oil.

Another embodiment comprises cyclosporin A, polyoxyl stearate, and maize oil.

Another embodiment comprises cyclosporin A, polyoxyl stearate, and linseed oil.

Another embodiment comprises cyclosporin A, polyoxyl stearate, and rapeseed oil.

Another embodiment comprises cyclosporin A, polyoxyl stearate, and soybean oil.

Another embodiment comprises cyclosporin A, polyoxyl stearate, and olive oil.

Another embodiment comprises cyclosporin A, polyoxyl stearate, and caraway oil.

Another embodiment comprises cyclosporin A, polyoxyl stearate, and rosemary oil.

Another embodiment comprises cyclosporin A, polyoxyl stearate, and peanut oil.

Another embodiment comprises cyclosporin A, polyoxyl stearate, and peppermint oil.

Another embodiment comprises cyclosporin A, polyoxyl stearate, and sunflower oil.

Another embodiment comprises cyclosporin A, polyoxyl stearate, and eucalpytus oil.

Another embodiment comprises cyclosporin A, polyoxyl stearate, and sesame oil.

Another embodiment comprises cyclosporin A, polyoxyl stearate, and an oil having a specific gravity below 0.9.

Another embodiment comprises cyclosporin A, polyoxyl stearate, and mineral oil.

Another embodiment comprises cyclosporin A, polyoxyl stearate, and coriander oil.

Another embodiment comprises cyclosporin A, polyoxyl stearate, and lavender oil.

Another embodiment comprises cyclosporin A, polyoxyl stearate, and citronella oil.

Another embodiment comprises cyclosporin A, polyoxyl stearate, and juniper oil.

Another embodiment comprises cyclosporin A, polyoxyl stearate, and lemon oil.

Another embodiment comprises cyclosporin A, polyoxyl stearate, and orange oil.

Another embodiment comprises cyclosporin A, polyoxyl stearate, and clary sage oil.

Another embodiment comprises cyclosporin A, polyoxyl stearate, and nutmeg oil.

Another embodiment comprises cyclosporin A, polyoxyl stearate, and tea tree oil.

Another embodiment comprises cyclosporin A, propylene glycol stearate, and an oil having a specific gravity between 0.90 and 0.95.

Another embodiment comprises cyclosporin A, propylene glycol stearate, and almond oil.

Another embodiment comprises cyclosporin A, propylene glycol stearate, and corn oil.

Another embodiment comprises cyclosporin A, propylene glycol stearate, and arachis oil.

Another embodiment comprises cyclosporin A, propylene glycol stearate, and cottonseed oil.

Another embodiment comprises cyclosporin A, propylene glycol stearate, and safflower oil.

Another embodiment comprises cyclosporin A, propylene glycol stearate, and maize oil.

Another embodiment comprises cyclosporin A, propylene glycol stearate, and linseed oil.

Another embodiment comprises cyclosporin A, propylene glycol stearate, and rapeseed oil.

Another embodiment comprises cyclosporin A, propylene glycol stearate, and soybean oil.

Another embodiment comprises cyclosporin A, propylene glycol stearate, and olive oil.

Another embodiment comprises cyclosporin A, propylene glycol stearate, and caraway oil.

Another embodiment comprises cyclosporin A, propylene glycol stearate, and rosemary oil.

Another embodiment comprises cyclosporin A, propylene glycol stearate, and peanut oil.

Another embodiment comprises cyclosporin A, propylene glycol stearate, and peppermint oil.

Another embodiment comprises cyclosporin A, propylene glycol stearate, and sunflower oil.

Another embodiment comprises cyclosporin A, propylene glycol stearate, and eucalpytus oil.

Another embodiment comprises cyclosporin A, propylene glycol stearate, and sesame oil.

Another embodiment comprises cyclosporin A, propylene glycol stearate, and an oil having a specific gravity below 0.9.

Another embodiment comprises cyclosporin A, propylene glycol stearate, and mineral oil.

Another embodiment comprises cyclosporin A, propylene glycol stearate, and coriander oil.

Another embodiment comprises cyclosporin A, propylene glycol stearate, and lavender oil.

Another embodiment comprises cyclosporin A, propylene glycol stearate, and citronella oil.

Another embodiment comprises cyclosporin A, propylene glycol stearate, and juniper oil.

Another embodiment comprises cyclosporin A, propylene glycol stearate, and lemon oil.

Another embodiment comprises cyclosporin A, propylene glycol stearate, and orange oil.

Another embodiment comprises cyclosporin A, propylene glycol stearate, and clary sage oil.

Another embodiment comprises cyclosporin A, propylene glycol stearate, and nutmeg oil.

Another embodiment comprises cyclosporin A, propylene glycol stearate, and tea tree oil.

Another embodiment comprises cyclosporin A, sucrose stearate, and an oil having a specific gravity between 0.90 and 0.95.

Another embodiment comprises cyclosporin A, sucrose stearate, and almond oil.

Another embodiment comprises cyclosporin A, sucrose stearate, and corn oil.

Another embodiment comprises cyclosporin A, sucrose stearate, and arachis oil.

Another embodiment comprises cyclosporin A, sucrose stearate, and cottonseed oil.

Another embodiment comprises cyclosporin A, sucrose stearate, and safflower oil.

Another embodiment comprises cyclosporin A, sucrose stearate, and maize oil.

Another embodiment comprises cyclosporin A, sucrose stearate, and linseed oil.

Another embodiment comprises cyclosporin A, sucrose stearate, and rapeseed oil.

Another embodiment comprises cyclosporin A, sucrose stearate, and soybean oil.

Another embodiment comprises cyclosporin A, sucrose stearate, and olive oil.

Another embodiment comprises cyclosporin A, sucrose stearate, and caraway oil.

Another embodiment comprises cyclosporin A, sucrose stearate, and rosemary oil.

Another embodiment comprises cyclosporin A, sucrose stearate, and peanut oil.

Another embodiment comprises cyclosporin A, sucrose stearate, and peppermint oil.

Another embodiment comprises cyclosporin A, sucrose stearate, and sunflower oil.

Another embodiment comprises cyclosporin A, sucrose stearate, and eucalpytus oil.

Another embodiment comprises cyclosporin A, sucrose stearate, and sesame oil.

Another embodiment comprises cyclosporin A, sucrose stearate, and an oil having a specific gravity below 0.9.

Another embodiment comprises cyclosporin A, sucrose stearate, and mineral oil.

Another embodiment comprises cyclosporin A, sucrose stearate, and coriander oil.

Another embodiment comprises cyclosporin A, sucrose stearate, and lavender oil.

Another embodiment comprises cyclosporin A, sucrose stearate, and citronella oil.

Another embodiment comprises cyclosporin A, sucrose stearate, and juniper oil.

Another embodiment comprises cyclosporin A, sucrose stearate, and lemon oil.

Another embodiment comprises cyclosporin A, sucrose stearate, and orange oil.

Another embodiment comprises cyclosporin A, sucrose stearate, and clary sage oil.

Another embodiment comprises cyclosporin A, sucrose stearate, and nutmeg oil.

Another embodiment comprises cyclosporin A, sucrose stearate, and tea tree oil.

Another embodiment comprises cyclosporin A, polyethylene glycol, and an oil having a specific gravity between 0.90 and 0.95.

Another embodiment comprises cyclosporin A, polyethylene glycol, and almond oil.

Another embodiment comprises cyclosporin A, polyethylene glycol, and corn oil.

Another embodiment comprises cyclosporin A, polyethylene glycol, and arachis oil.

Another embodiment comprises cyclosporin A, polyethylene glycol, and cottonseed oil.

Another embodiment comprises cyclosporin A, polyethylene glycol, and safflower oil.

Another embodiment comprises cyclosporin A, polyethylene glycol, and maize oil.

Another embodiment comprises cyclosporin A, polyethylene glycol, and linseed oil.

Another embodiment comprises cyclosporin A, polyethylene glycol, and rapeseed oil.

Another embodiment comprises cyclosporin A, polyethylene glycol, and soybean oil.

Another embodiment comprises cyclosporin A, polyethylene glycol, and olive oil.

Another embodiment comprises cyclosporin A, polyethylene glycol, and caraway oil.

Another embodiment comprises cyclosporin A, polyethylene glycol, and rosemary oil.

Another embodiment comprises cyclosporin A, polyethylene glycol, and peanut oil.

Another embodiment comprises cyclosporin A, polyethylene glycol, and peppermint oil.

Another embodiment comprises cyclosporin A, polyethylene glycol, and sunflower oil.

Another embodiment comprises cyclosporin A, polyethylene glycol, and eucalpytus oil.

Another embodiment comprises cyclosporin A, polyethylene glycol, and sesame oil.

Another embodiment comprises cyclosporin A, polyethylene glycol, and an oil having a specific gravity below 0.9.

Another embodiment comprises cyclosporin A, polyethylene glycol, and mineral oil.

Another embodiment comprises cyclosporin A, polyethylene glycol, and coriander oil.

Another embodiment comprises cyclosporin A, polyethylene glycol, and lavender oil.

Another embodiment comprises cyclosporin A, polyethylene glycol, and citronella oil.

Another embodiment comprises cyclosporin A, polyethylene glycol, and juniper oil.

Another embodiment comprises cyclosporin A, polyethylene glycol, and lemon oil.

Another embodiment comprises cyclosporin A, polyethylene glycol, and orange oil.

Another embodiment comprises cyclosporin A, polyethylene glycol, and clary sage oil.

Another embodiment comprises cyclosporin A, polyethylene glycol, and nutmeg oil.

Another embodiment comprises cyclosporin A, polyethylene glycol, and tea tree oil.

Another embodiment comprises cyclosporin A, polyethylene oxide, and an oil having a specific gravity between 0.90 and 0.95.

Another embodiment comprises cyclosporin A, polyethylene oxide, and almond oil.

Another embodiment comprises cyclosporin A, polyethylene oxide, and corn oil.

Another embodiment comprises cyclosporin A, polyethylene oxide, and arachis oil.

Another embodiment comprises cyclosporin A, polyethylene oxide, and cottonseed oil.

Another embodiment comprises cyclosporin A, polyethylene oxide, and safflower oil.

Another embodiment comprises cyclosporin A, polyethylene oxide, and maize oil.

Another embodiment comprises cyclosporin A, polyethylene oxide, and linseed oil.

Another embodiment comprises cyclosporin A, polyethylene oxide, and rapeseed oil.

Another embodiment comprises cyclosporin A, polyethylene oxide, and soybean oil.

Another embodiment comprises cyclosporin A, polyethylene oxide, and olive oil.

Another embodiment comprises cyclosporin A, polyethylene oxide, and caraway oil.

Another embodiment comprises cyclosporin A, polyethylene oxide, and rosemary oil.

Another embodiment comprises cyclosporin A, polyethylene oxide, and peanut oil.

Another embodiment comprises cyclosporin A, polyethylene oxide, and peppermint oil.

Another embodiment comprises cyclosporin A, polyethylene oxide, and sunflower oil.

Another embodiment comprises cyclosporin A, polyethylene oxide, and eucalpytus oil.

Another embodiment comprises cyclosporin A, polyethylene oxide, and sesame oil.

Another embodiment comprises cyclosporin A, polyethylene oxide, and an oil having a specific gravity below 0.9.

Another embodiment comprises cyclosporin A, polyethylene oxide, and mineral oil.

Another embodiment comprises cyclosporin A, polyethylene oxide, and coriander oil.

Another embodiment comprises cyclosporin A, polyethylene oxide, and lavender oil.

Another embodiment comprises cyclosporin A, polyethylene oxide, and citronella oil.

Another embodiment comprises cyclosporin A, polyethylene oxide, and juniper oil.

Another embodiment comprises cyclosporin A, polyethylene oxide, and lemon oil.

Another embodiment comprises cyclosporin A, polyethylene oxide, and orange oil.

Another embodiment comprises cyclosporin A, polyethylene oxide, and clary sage oil.

Another embodiment comprises cyclosporin A, polyethylene oxide, and nutmeg oil.

Another embodiment comprises cyclosporin A, polyethylene oxide, and tea tree oil.

Another embodiment comprises cyclosporin A, polypropylene oxide, and an oil having a specific gravity between 0.90 and 0.95.

Another embodiment comprises cyclosporin A, polypropylene oxide, and almond oil.

Another embodiment comprises cyclosporin A, polypropylene oxide, and corn oil.

Another embodiment comprises cyclosporin A, polypropylene oxide, and arachis oil.

Another embodiment comprises cyclosporin A, polypropylene oxide, and cottonseed oil.

Another embodiment comprises cyclosporin A, polypropylene oxide, and safflower oil.

Another embodiment comprises cyclosporin A, polypropylene oxide, and maize oil.

Another embodiment comprises cyclosporin A, polypropylene oxide, and linseed oil.

Another embodiment comprises cyclosporin A, polypropylene oxide, and rapeseed oil.

Another embodiment comprises cyclosporin A, polypropylene oxide, and soybean oil.

Another embodiment comprises cyclosporin A, polypropylene oxide, and olive oil.

Another embodiment comprises cyclosporin A, polypropylene oxide, and caraway oil.

Another embodiment comprises cyclosporin A, polypropylene oxide, and rosemary oil.

Another embodiment comprises cyclosporin A, polypropylene oxide, and peanut oil.

Another embodiment comprises cyclosporin A, polypropylene oxide, and peppermint oil.

Another embodiment comprises cyclosporin A, polypropylene oxide, and sunflower oil.

Another embodiment comprises cyclosporin A, polypropylene oxide, and eucalpytus oil.

Another embodiment comprises cyclosporin A, polypropylene oxide, and sesame oil.

Another embodiment comprises cyclosporin A, polypropylene oxide, and an oil having a specific gravity below 0.9.

Another embodiment comprises cyclosporin A, polypropylene oxide, and mineral oil.

Another embodiment comprises cyclosporin A, polypropylene oxide, and coriander oil.

Another embodiment comprises cyclosporin A, polypropylene oxide, and lavender oil.

Another embodiment comprises cyclosporin A, polypropylene oxide, and citronella oil.

Another embodiment comprises cyclosporin A, polypropylene oxide, and juniper oil.

Another embodiment comprises cyclosporin A, polypropylene oxide, and lemon oil.

Another embodiment comprises cyclosporin A, polypropylene oxide, and orange oil.

Another embodiment comprises cyclosporin A, polypropylene oxide, and clary sage oil.

Another embodiment comprises cyclosporin A, polypropylene oxide, and nutmeg oil.

Another embodiment comprises cyclosporin A, polypropylene oxide, and tea tree oil.

Another embodiment comprises cyclosporin A, a polyethylene oxide-polypropylene oxide copolymer, and an oil having a specific gravity between 0.90 and 0.95.

Another embodiment comprises cyclosporin A, a polyethylene oxide-polypropylene oxide copolymer, and almond oil.

Another embodiment comprises cyclosporin A, a polyethylene oxide-polypropylene oxide copolymer, and corn oil.

Another embodiment comprises cyclosporin A, a polyethylene oxide-polypropylene oxide copolymer, and arachis oil.

Another embodiment comprises cyclosporin A, a polyethylene oxide-polypropylene oxide copolymer, and cottonseed oil.

Another embodiment comprises cyclosporin A, a polyethylene oxide-polypropylene oxide copolymer, and safflower oil.

Another embodiment comprises cyclosporin A, a polyethylene oxide-polypropylene oxide copolymer, and maize oil.

Another embodiment comprises cyclosporin A, a polyethylene oxide-polypropylene oxide copolymer, and linseed oil.

Another embodiment comprises cyclosporin A, a polyethylene oxide-polypropylene oxide copolymer, and rapeseed oil.

Another embodiment comprises cyclosporin A, a polyethylene oxide-polypropylene oxide copolymer, and soybean oil.

Another embodiment comprises cyclosporin A, a polyethylene oxide-polypropylene oxide copolymer, and olive oil.

Another embodiment comprises cyclosporin A, a polyethylene oxide-polypropylene oxide copolymer, and caraway oil.

Another embodiment comprises cyclosporin A, a polyethylene oxide-polypropylene oxide copolymer, and rosemary oil.

Another embodiment comprises cyclosporin A, a polyethylene oxide-polypropylene oxide copolymer, and peanut oil.

Another embodiment comprises cyclosporin A, a polyethylene oxide-polypropylene oxide copolymer, and peppermint oil.

Another embodiment comprises cyclosporin A, a polyethylene oxide-polypropylene oxide copolymer, and sunflower oil.

Another embodiment comprises cyclosporin A, a polyethylene oxide-polypropylene oxide copolymer, and eucalpytus oil.

Another embodiment comprises cyclosporin A, a polyethylene oxide-polypropylene oxide copolymer, and sesame oil.

Another embodiment comprises cyclosporin A, a polyethylene oxide-polypropylene oxide copolymer, and an oil having a specific gravity below 0.9.

Another embodiment comprises cyclosporin A, a polyethylene oxide-polypropylene oxide copolymer, and mineral oil.

Another embodiment comprises cyclosporin A, a polyethylene oxide-polypropylene oxide copolymer, and coriander oil.

Another embodiment comprises cyclosporin A, a polyethylene oxide-polypropylene oxide copolymer, and lavender oil.

Another embodiment comprises cyclosporin A, a polyethylene oxide-polypropylene oxide copolymer, and citronella oil.

Another embodiment comprises cyclosporin A, a polyethylene oxide-polypropylene oxide copolymer, and juniper oil.

Another embodiment comprises cyclosporin A, a polyethylene oxide-polypropylene oxide copolymer, and lemon oil.

Another embodiment comprises cyclosporin A, a polyethylene oxide-polypropylene oxide copolymer, and orange oil.

Another embodiment comprises cyclosporin A, a polyethylene oxide-polypropylene oxide copolymer, and clary sage oil.

Another embodiment comprises cyclosporin A, a polyethylene oxide-polypropylene oxide copolymer, and nutmeg oil.

Another embodiment comprises cyclosporin A, a polyethylene oxide-polypropylene oxide copolymer, and tea tree oil.

Another embodiment comprises cyclosporin A, an alcohol ethoxylate, and an oil having a specific gravity between 0.90 and 0.95.

Another embodiment comprises cyclosporin A, an alcohol ethoxylate, and almond oil.

Another embodiment comprises cyclosporin A, an alcohol ethoxylate, and corn oil.

Another embodiment comprises cyclosporin A, an alcohol ethoxylate, and arachis oil.

Another embodiment comprises cyclosporin A, an alcohol ethoxylate, and cottonseed oil.

Another embodiment comprises cyclosporin A, an alcohol ethoxylate, and safflower oil.

Another embodiment comprises cyclosporin A, an alcohol ethoxylate, and maize oil.

Another embodiment comprises cyclosporin A, an alcohol ethoxylate, and linseed oil.

Another embodiment comprises cyclosporin A, an alcohol ethoxylate, and rapeseed oil.

Another embodiment comprises cyclosporin A, an alcohol ethoxylate, and soybean oil.

Another embodiment comprises cyclosporin A, an alcohol ethoxylate, and olive oil.

Another embodiment comprises cyclosporin A, an alcohol ethoxylate, and caraway oil.

Another embodiment comprises cyclosporin A, an alcohol ethoxylate, and rosemary oil.

Another embodiment comprises cyclosporin A, an alcohol ethoxylate, and peanut oil.

Another embodiment comprises cyclosporin A, an alcohol ethoxylate, and peppermint oil.

Another embodiment comprises cyclosporin A, an alcohol ethoxylate, and sunflower oil.

Another embodiment comprises cyclosporin A, an alcohol ethoxylate, and eucalpytus oil.

Another embodiment comprises cyclosporin A, an alcohol ethoxylate, and sesame oil.

Another embodiment comprises cyclosporin A, an alcohol ethoxylate, and an oil having a specific gravity below 0.9.

Another embodiment comprises cyclosporin A, an alcohol ethoxylate, and mineral oil.

Another embodiment comprises cyclosporin A, an alcohol ethoxylate, and coriander oil.

Another embodiment comprises cyclosporin A, an alcohol ethoxylate, and lavender oil.

Another embodiment comprises cyclosporin A, an alcohol ethoxylate, and citronella oil.

Another embodiment comprises cyclosporin A, an alcohol ethoxylate, and juniper oil.

Another embodiment comprises cyclosporin A, an alcohol ethoxylate, and lemon oil.

Another embodiment comprises cyclosporin A, an alcohol ethoxylate, and orange oil.

Another embodiment comprises cyclosporin A, an alcohol ethoxylate, and clary sage oil.

Another embodiment comprises cyclosporin A, an alcohol ethoxylate, and nutmeg oil.

Another embodiment comprises cyclosporin A, an alcohol ethoxylate, and tea tree oil.

Another embodiment comprises cyclosporin A, an alkylphenol ethoxylate, and an oil having a specific gravity between 0.90 and 0.95.

Another embodiment comprises cyclosporin A, an alkylphenol ethoxylate, and almond oil.

Another embodiment comprises cyclosporin A, an alkylphenol ethoxylate, and corn oil.

Another embodiment comprises cyclosporin A, an alkylphenol ethoxylate, and arachis oil.

Another embodiment comprises cyclosporin A, an alkylphenol ethoxylate, and cottonseed oil.

Another embodiment comprises cyclosporin A, an alkylphenol ethoxylate, and safflower oil.

Another embodiment comprises cyclosporin A, an alkylphenol ethoxylate, and maize oil.

Another embodiment comprises cyclosporin A, an alkylphenol ethoxylate, and linseed oil.

Another embodiment comprises cyclosporin A, an alkylphenol ethoxylate, and rapeseed oil.

Another embodiment comprises cyclosporin A, an alkylphenol ethoxylate, and soybean oil.

Another embodiment comprises cyclosporin A, an alkylphenol ethoxylate, and olive oil.

Another embodiment comprises cyclosporin A, an alkylphenol ethoxylate, and caraway oil.

Another embodiment comprises cyclosporin A, an alkylphenol ethoxylate, and rosemary oil.

Another embodiment comprises cyclosporin A, an alkylphenol ethoxylate, and peanut oil.

Another embodiment comprises cyclosporin A, an alkylphenol ethoxylate, and peppermint oil.

Another embodiment comprises cyclosporin A, an alkylphenol ethoxylate, and sunflower oil.

Another embodiment comprises cyclosporin A, an alkylphenol ethoxylate, and eucalpytus oil.

Another embodiment comprises cyclosporin A, an alkylphenol ethoxylate, and sesame oil.

Another embodiment comprises cyclosporin A, an alkylphenol ethoxylate, and an oil having a specific gravity below 0.9.

Another embodiment comprises cyclosporin A, an alkylphenol ethoxylate, and mineral oil.

Another embodiment comprises cyclosporin A, an alkylphenol ethoxylate, and coriander oil.

Another embodiment comprises cyclosporin A, an alkylphenol ethoxylate, and lavender oil.

Another embodiment comprises cyclosporin A, an alkylphenol ethoxylate, and citronella oil.

Another embodiment comprises cyclosporin A, an alkylphenol ethoxylate, and juniper oil.

Another embodiment comprises cyclosporin A, an alkylphenol ethoxylate, and lemon oil.

Another embodiment comprises cyclosporin A, an alkylphenol ethoxylate, and orange oil.

Another embodiment comprises cyclosporin A, an alkylphenol ethoxylate, and clary sage oil.

Another embodiment comprises cyclosporin A, an alkylphenol ethoxylate, and nutmeg oil.

Another embodiment comprises cyclosporin A, an alkylphenol ethoxylate, and tea tree oil.

Another embodiment comprises cyclosporin A, an alkyl glycoside, and an oil having a specific gravity between 0.90 and 0.95.

Another embodiment comprises cyclosporin A, an alkyl glycoside, and almond oil.

Another embodiment comprises cyclosporin A, an alkyl glycoside, and corn oil.

Another embodiment comprises cyclosporin A, an alkyl glycoside, and arachis oil.

Another embodiment comprises cyclosporin A, an alkyl glycoside, and cottonseed oil.

Another embodiment comprises cyclosporin A, an alkyl glycoside, and safflower oil.

Another embodiment comprises cyclosporin A, an alkyl glycoside, and maize oil.

Another embodiment comprises cyclosporin A, an alkyl glycoside, and linseed oil.

Another embodiment comprises cyclosporin A, an alkyl glycoside, and rapeseed oil.

Another embodiment comprises cyclosporin A, an alkyl glycoside, and soybean oil.

Another embodiment comprises cyclosporin A, an alkyl glycoside, and olive oil.

Another embodiment comprises cyclosporin A, an alkyl glycoside, and caraway oil.

Another embodiment comprises cyclosporin A, an alkyl glycoside, and rosemary oil.

Another embodiment comprises cyclosporin A, an alkyl glycoside, and peanut oil.

Another embodiment comprises cyclosporin A, an alkyl glycoside, and peppermint oil.

Another embodiment comprises cyclosporin A, an alkyl glycoside, and sunflower oil.

Another embodiment comprises cyclosporin A, an alkyl glycoside, and eucalpytus oil.

Another embodiment comprises cyclosporin A, an alkyl glycoside, and sesame oil.

Another embodiment comprises cyclosporin A, an alkyl glycoside, and an oil having a specific gravity below 0.9.

Another embodiment comprises cyclosporin A

Another embodiment comprises cyclosporin A, an alkyl glycoside, and coriander oil.

Another embodiment comprises cyclosporin A, an alkyl glycoside, and lavender oil.

Another embodiment comprises cyclosporin A, an alkyl glycoside, and citronella oil.

Another embodiment comprises cyclosporin A, an alkyl glycoside, and juniper oil.

Another embodiment comprises cyclosporin A, an alkyl glycoside, and lemon oil.

Another embodiment comprises cyclosporin A, an alkyl glycoside, and orange oil.

Another embodiment comprises cyclosporin A, an alkyl glycoside, and clary sage oil.

Another embodiment comprises cyclosporin A, an alkyl glycoside, and nutmeg oil.

Another embodiment comprises cyclosporin A, an alkyl glycoside, and tea tree oil.

Another embodiment comprises cyclosporin A, alkyl polyglycoside, and an oil having a specific gravity between 0.90 and 0.95.

Another embodiment comprises cyclosporin A, alkyl polyglycoside, and almond oil.

Another embodiment comprises cyclosporin A, alkyl polyglycoside, and corn oil.

Another embodiment comprises cyclosporin A, alkyl polyglycoside, and arachis oil.

Another embodiment comprises cyclosporin A, alkyl polyglycoside, and cottonseed oil.

Another embodiment comprises cyclosporin A, alkyl polyglycoside, and safflower oil.

Another embodiment comprises cyclosporin A, alkyl polyglycoside, and maize oil.

Another embodiment comprises cyclosporin A, alkyl polyglycoside, and linseed oil.

Another embodiment comprises cyclosporin A, alkyl polyglycoside, and rapeseed oil.

Another embodiment comprises cyclosporin A, alkyl polyglycoside, and soybean oil.

Another embodiment comprises cyclosporin A, alkyl polyglycoside, and olive oil.

Another embodiment comprises cyclosporin A, alkyl polyglycoside, and caraway oil.

Another embodiment comprises cyclosporin A, alkyl polyglycoside, and rosemary oil.

Another embodiment comprises cyclosporin A, alkyl polyglycoside, and peanut oil.

Another embodiment comprises cyclosporin A, alkyl polyglycoside, and peppermint oil.

Another embodiment comprises cyclosporin A, alkyl polyglycoside, and sunflower oil.

Another embodiment comprises cyclosporin A, alkyl polyglycoside, and eucalpytus oil.

Another embodiment comprises cyclosporin A, alkyl polyglycoside, and sesame oil.

Another embodiment comprises cyclosporin A, alkyl polyglycoside, and an oil having a specific gravity below 0.9.

Another embodiment comprises cyclosporin A, alkyl polyglycoside, and mineral oil.

Another embodiment comprises cyclosporin A, alkyl polyglycoside, and coriander oil.

Another embodiment comprises cyclosporin A, alkyl polyglycoside, and lavender oil.

Another embodiment comprises cyclosporin A, alkyl polyglycoside, and citronella oil.

Another embodiment comprises cyclosporin A, alkyl polyglycoside, and juniper oil.

Another embodiment comprises cyclosporin A, alkyl polyglycoside, and lemon oil.

Another embodiment comprises cyclosporin A, alkyl polyglycoside, and orange oil.

Another embodiment comprises cyclosporin A, alkyl polyglycoside, and clary sage oil.

Another embodiment comprises cyclosporin A, alkyl polyglycoside, and nutmeg oil.

Another embodiment comprises cyclosporin A, alkyl polyglycoside, and tea tree oil.

Another embodiment comprises cyclosporin A, a fatty alcohol, and an oil having a specific gravity between 0.90 and 0.95.

Another embodiment comprises cyclosporin A, a fatty alcohol, and almond oil.

Another embodiment comprises cyclosporin A, a fatty alcohol, and corn oil.

Another embodiment comprises cyclosporin A, a fatty alcohol, and arachis oil.

Another embodiment comprises cyclosporin A, a fatty alcohol, and cottonseed oil.

Another embodiment comprises cyclosporin A, a fatty alcohol, and safflower oil.

Another embodiment comprises cyclosporin A, a fatty alcohol, and maize oil.

Another embodiment comprises cyclosporin A, a fatty alcohol, and linseed oil.

Another embodiment comprises cyclosporin A, a fatty alcohol, and rapeseed oil.

Another embodiment comprises cyclosporin A, a fatty alcohol, and soybean oil.

Another embodiment comprises cyclosporin A, a fatty alcohol, and olive oil.

Another embodiment comprises cyclosporin A, a fatty alcohol, and caraway oil.

Another embodiment comprises cyclosporin A, a fatty alcohol, and rosemary oil.

Another embodiment comprises cyclosporin A, a fatty alcohol, and peanut oil.

Another embodiment comprises cyclosporin A, a fatty alcohol, and peppermint oil.

Another embodiment comprises cyclosporin A, a fatty alcohol, and sunflower oil.

Another embodiment comprises cyclosporin A, a fatty alcohol, and eucalpytus oil.

Another embodiment comprises cyclosporin A, a fatty alcohol, and sesame oil.

Another embodiment comprises cyclosporin A, a fatty alcohol, and an oil having a specific gravity below 0.9.

Another embodiment comprises cyclosporin A, a fatty alcohol, and mineral oil.

Another embodiment comprises cyclosporin A, a fatty alcohol, and coriander oil.

Another embodiment comprises cyclosporin A, a fatty alcohol, and lavender oil.

Another embodiment comprises cyclosporin A, a fatty alcohol, and citronella oil.

Another embodiment comprises cyclosporin A, a fatty alcohol, and juniper oil.

Another embodiment comprises cyclosporin A, a fatty alcohol, and lemon oil.

Another embodiment comprises cyclosporin A, a fatty alcohol, and orange oil.

Another embodiment comprises cyclosporin A, a fatty alcohol, and clary sage oil.

Another embodiment comprises cyclosporin A, a fatty alcohol, and nutmeg oil.

Another embodiment comprises cyclosporin A, a fatty alcohol, and tea tree oil.

Another embodiment comprises cyclosporin A, hydroxypropylmethyl cellulose, and an oil having a specific gravity between 0.90 and 0.95.

Another embodiment comprises cyclosporin A, hydroxypropylmethyl cellulose, and almond oil.

Another embodiment comprises cyclosporin A, hydroxypropylmethyl cellulose, and corn oil.

Another embodiment comprises cyclosporin A, hydroxypropylmethyl cellulose, and arachis oil.

Another embodiment comprises cyclosporin A, hydroxypropylmethyl cellulose, and cottonseed oil.

Another embodiment comprises cyclosporin A, hydroxypropylmethyl cellulose, and safflower oil.

Another embodiment comprises cyclosporin A, hydroxypropylmethyl cellulose, and maize oil.

Another embodiment comprises cyclosporin A, hydroxypropylmethyl cellulose, and linseed oil.

Another embodiment comprises cyclosporin A, hydroxypropylmethyl cellulose, and rapeseed oil.

Another embodiment comprises cyclosporin A, hydroxypropylmethyl cellulose, and soybean oil.

Another embodiment comprises cyclosporin A, hydroxypropylmethyl cellulose, and olive oil.

Another embodiment comprises cyclosporin A, hydroxypropylmethyl cellulose, and caraway oil.

Another embodiment comprises cyclosporin A, hydroxypropylmethyl cellulose, and rosemary oil.

Another embodiment comprises cyclosporin A, hydroxypropylmethyl cellulose, and peanut oil.

Another embodiment comprises cyclosporin A, hydroxypropylmethyl cellulose, and peppermint oil.

Another embodiment comprises cyclosporin A, hydroxypropylmethyl cellulose, and sunflower oil.

Another embodiment comprises cyclosporin A, hydroxypropylmethyl cellulose, and eucalpytus oil.

Another embodiment comprises cyclosporin A, hydroxypropylmethyl cellulose, and sesame oil.

Another embodiment comprises cyclosporin A, hydroxypropylmethyl cellulose, and an oil having a specific gravity below 0.9.

Another embodiment comprises cyclosporin A, hydroxypropylmethyl cellulose, and mineral oil.

Another embodiment comprises cyclosporin A, hydroxypropylmethyl cellulose, and coriander oil.

Another embodiment comprises cyclosporin A, hydroxypropylmethyl cellulose, and lavender oil.

Another embodiment comprises cyclosporin A, hydroxypropylmethyl cellulose, and citronella oil.

Another embodiment comprises cyclosporin A, hydroxypropylmethyl cellulose, and juniper oil.

Another embodiment comprises cyclosporin A, hydroxypropylmethyl cellulose, and lemon oil.

Another embodiment comprises cyclosporin A, hydroxypropylmethyl cellulose, and orange oil.

Another embodiment comprises cyclosporin A, hydroxypropylmethyl cellulose, and clary sage oil.

Another embodiment comprises cyclosporin A, hydroxypropylmethyl cellulose, and nutmeg oil.

Another embodiment comprises cyclosporin A, hydroxypropylmethyl cellulose, and tea tree oil.

Another embodiment comprises cyclosporin A, carboxymethyl cellulose, and an oil having a specific gravity between 0.90 and 0.95.

Another embodiment comprises cyclosporin A, carboxymethyl cellulose, and almond oil.

Another embodiment comprises cyclosporin A, carboxymethyl cellulose, and corn oil.

Another embodiment comprises cyclosporin A, carboxymethyl cellulose, and arachis oil.

Another embodiment comprises cyclosporin A, carboxymethyl cellulose, and cottonseed oil.

Another embodiment comprises cyclosporin A, carboxymethyl cellulose, and safflower oil.

Another embodiment comprises cyclosporin A, carboxymethyl cellulose, and maize oil.

Another embodiment comprises cyclosporin A, carboxymethyl cellulose, and linseed oil.

Another embodiment comprises cyclosporin A, carboxymethyl cellulose, and rapeseed oil.

Another embodiment comprises cyclosporin A, carboxymethyl cellulose, and soybean oil.

Another embodiment comprises cyclosporin A, carboxymethyl cellulose, and olive oil.

Another embodiment comprises cyclosporin A, carboxymethyl cellulose, and caraway oil.

Another embodiment comprises cyclosporin A, carboxymethyl cellulose, and rosemary oil.

Another embodiment comprises cyclosporin A, carboxymethyl cellulose, and peanut oil.

Another embodiment comprises cyclosporin A, carboxymethyl cellulose, and peppermint oil.

Another embodiment comprises cyclosporin A, carboxymethyl cellulose, and sunflower oil.

Another embodiment comprises cyclosporin A, carboxymethyl cellulose, and eucalpytus oil.

Another embodiment comprises cyclosporin A, carboxymethyl cellulose, and sesame oil.

Another embodiment comprises cyclosporin A, carboxymethyl cellulose, and an oil having a specific gravity below 0.9.

Another embodiment comprises cyclosporin A, carboxymethyl cellulose, and mineral oil.

Another embodiment comprises cyclosporin A, carboxymethyl cellulose, and coriander oil.

Another embodiment comprises cyclosporin A, carboxymethyl cellulose, and lavender oil.

Another embodiment comprises cyclosporin A, carboxymethyl cellulose, and citronella oil.

Another embodiment comprises cyclosporin A, carboxymethyl cellulose, and juniper oil.

Another embodiment comprises cyclosporin A, carboxymethyl cellulose, and lemon oil.

Another embodiment comprises cyclosporin A, carboxymethyl cellulose, and orange oil.

Another embodiment comprises cyclosporin A, carboxymethyl cellulose, and clary sage oil.

Another embodiment comprises cyclosporin A, carboxymethyl cellulose, and nutmeg oil.

Another embodiment comprises cyclosporin A, carboxymethyl cellulose, and tea tree oil.

Another embodiment comprises cyclosporin A, a polyacrylic acid, and an oil having a specific gravity between 0.90 and 0.95.

Another embodiment comprises cyclosporin A, a polyacrylic acid, and almond oil.

Another embodiment comprises cyclosporin A, a polyacrylic acid, and corn oil.

Another embodiment comprises cyclosporin A, a polyacrylic acid, and arachis oil.

Another embodiment comprises cyclosporin A, a polyacrylic acid, and cottonseed oil.
Another embodiment comprises cyclosporin A, a polyacrylic acid, and safflower oil.
Another embodiment comprises cyclosporin A, a polyacrylic acid, and maize oil.
Another embodiment comprises cyclosporin A, a polyacrylic acid, and linseed oil.
Another embodiment comprises cyclosporin A, a polyacrylic acid, and rapeseed oil.
Another embodiment comprises cyclosporin A, a polyacrylic acid, and soybean oil.
Another embodiment comprises cyclosporin A, a polyacrylic acid, and olive oil.
Another embodiment comprises cyclosporin A, a polyacrylic acid, and caraway oil.
Another embodiment comprises cyclosporin A, a polyacrylic acid, and rosemary oil.
Another embodiment comprises cyclosporin A, a polyacrylic acid, and peanut oil.
Another embodiment comprises cyclosporin A, a polyacrylic acid, and peppermint oil.
Another embodiment comprises cyclosporin A, a polyacrylic acid, and sunflower oil.
Another embodiment comprises cyclosporin A, a polyacrylic acid, and eucalpytus oil.
Another embodiment comprises cyclosporin A, a polyacrylic acid, and sesame oil.
Another embodiment comprises cyclosporin A, a polyacrylic acid, and an oil having a specific gravity below 0.9.
Another embodiment comprises cyclosporin A, a polyacrylic acid, and mineral oil.
Another embodiment comprises cyclosporin A, a polyacrylic acid, and coriander oil.
Another embodiment comprises cyclosporin A, a polyacrylic acid, and lavender oil.
Another embodiment comprises cyclosporin A, a polyacrylic acid, and citronella oil.
Another embodiment comprises cyclosporin A, a polyacrylic acid, and juniper oil.
Another embodiment comprises cyclosporin A, a polyacrylic acid, and lemon oil.
Another embodiment comprises cyclosporin A, a polyacrylic acid, and orange oil.
Another embodiment comprises cyclosporin A, a polyacrylic acid, and clary sage oil.
Another embodiment comprises cyclosporin A, a polyacrylic acid, and nutmeg oil.
Another embodiment comprises cyclosporin A, a polyacrylic acid, and tea tree oil.
Another embodiment comprises cyclosporin A, a Carbomer, and an oil having a specific gravity between 0.90 and 0.95.
Another embodiment comprises cyclosporin A, a Carbomer, and almond oil.
Another embodiment comprises cyclosporin A, a Carbomer, and corn oil.
Another embodiment comprises cyclosporin A, a Carbomer, and arachis oil.
Another embodiment comprises cyclosporin A, a Carbomer, and cottonseed oil.
Another embodiment comprises cyclosporin A, a Carbomer, and safflower oil.
Another embodiment comprises cyclosporin A, a Carbomer, and maize oil.
Another embodiment comprises cyclosporin A, a Carbomer, and linseed oil.
Another embodiment comprises cyclosporin A, a Carbomer, and rapeseed oil.
Another embodiment comprises cyclosporin A, a Carbomer, and soybean oil.
Another embodiment comprises cyclosporin A, a Carbomer, and olive oil.
Another embodiment comprises cyclosporin A, a Carbomer, and caraway oil.
Another embodiment comprises cyclosporin A, a Carbomer, and rosemary oil.
Another embodiment comprises cyclosporin A, a Carbomer, and peanut oil.
Another embodiment comprises cyclosporin A, a Carbomer, and peppermint oil.
Another embodiment comprises cyclosporin A, a Carbomer, and sunflower oil.
Another embodiment comprises cyclosporin A, a Carbomer, and eucalpytus oil.
Another embodiment comprises cyclosporin A, a Carbomer, and sesame oil.
Another embodiment comprises cyclosporin A, a Carbomer, and an oil having a specific gravity below 0.9.
Another embodiment comprises cyclosporin A, a Carbomer, and mineral oil.
Another embodiment comprises cyclosporin A, a Carbomer, and coriander oil.
Another embodiment comprises cyclosporin A, a Carbomer, and lavender oil.
Another embodiment comprises cyclosporin A, a Carbomer, and citronella oil.
Another embodiment comprises cyclosporin A, a Carbomer, and juniper oil.
Another embodiment comprises cyclosporin A, a Carbomer, and lemon oil.
Another embodiment comprises cyclosporin A, a Carbomer, and orange oil.
Another embodiment comprises cyclosporin A, a Carbomer, and clary sage oil.
Another embodiment comprises cyclosporin A, a Carbomer, and nutmeg oil.
Another embodiment comprises cyclosporin A, a Carbomer, and tea tree oil.
Another embodiment comprises cyclosporin A, a phosphalipid, and an oil having a specific gravity between 0.90 and 0.95.
Another embodiment comprises cyclosporin A, a phosphalipid, and almond oil.
Another embodiment comprises cyclosporin A, a phosphalipid, and corn oil.
Another embodiment comprises cyclosporin A, a phosphalipid, and arachis oil.
Another embodiment comprises cyclosporin A, a phosphalipid, and cottonseed oil.
Another embodiment comprises cyclosporin A, a phosphalipid, and safflower oil.
Another embodiment comprises cyclosporin A, a phosphalipid, and maize oil.
Another embodiment comprises cyclosporin A, a phosphalipid, and linseed oil.
Another embodiment comprises cyclosporin A, a phosphalipid, and rapeseed oil.
Another embodiment comprises cyclosporin A, a phosphalipid, and soybean oil.
Another embodiment comprises cyclosporin A, a phosphalipid, and olive oil.
Another embodiment comprises cyclosporin A, a phosphalipid, and caraway oil.

Another embodiment comprises cyclosporin A, a phosphalipid, and rosemary oil.

Another embodiment comprises cyclosporin A, a phosphalipid, and peanut oil.

Another embodiment comprises cyclosporin A, a phosphalipid, and peppermint oil.

Another embodiment comprises cyclosporin A, a phosphalipid, and sunflower oil.

Another embodiment comprises cyclosporin A, a phosphalipid, and eucalpytus oil.

Another embodiment comprises cyclosporin A, a phosphalipid, and sesame oil.

Another embodiment comprises cyclosporin A, a phosphalipid, and an oil having a specific gravity below 0.9.

Another embodiment comprises cyclosporin A, a phosphalipid, and mineral oil.

Another embodiment comprises cyclosporin A, a phosphalipid, and coriander oil.

Another embodiment comprises cyclosporin A, a phosphalipid, and lavender oil.

Another embodiment comprises cyclosporin A, a phosphalipid, and citronella oil.

Another embodiment comprises cyclosporin A, a phosphalipid, and juniper oil.

Another embodiment comprises cyclosporin A, a phosphalipid, and lemon oil.

Another embodiment comprises cyclosporin A, a phosphalipid, and orange oil.

Another embodiment comprises cyclosporin A, a phosphalipid, and clary sage oil.

Another embodiment comprises cyclosporin A, a phosphalipid, and nutmeg oil.

Another embodiment comprises cyclosporin A, a phosphalipid, and tea tree oil.

Another embodiment comprises cyclosporin A, phosphatidyl chloline, and an oil having a specific gravity between 0.90 and 0.95.

Another embodiment comprises cyclosporin A, phosphatidyl chlorine, and almond oil.

Another embodiment comprises cyclosporin A, phosphatidyl chlorine, and corn oil.

Another embodiment comprises cyclosporin A, phosphatidyl chlorine, and arachis oil.

Another embodiment comprises cyclosporin A, phosphatidyl chloline, and cottonseed oil.

Another embodiment comprises cyclosporin A, phosphatidyl chloline, and safflower oil.

Another embodiment comprises cyclosporin A, phosphatidyl chloline, and maize oil.

Another embodiment comprises cyclosporin A, phosphatidyl chloline, and linseed oil.

Another embodiment comprises cyclosporin A, phosphatidyl chloline, and rapeseed oil.

Another embodiment comprises cyclosporin A, phosphatidyl chlorine, and soybean oil.

Another embodiment comprises cyclosporin A, phosphatidyl chloline, and olive oil.

Another embodiment comprises cyclosporin A, phosphatidyl chloline, and caraway oil.

Another embodiment comprises cyclosporin A, phosphatidyl chloline, and rosemary oil.

Another embodiment comprises cyclosporin A, phosphatidyl chloline, and peanut oil.

Another embodiment comprises cyclosporin A, phosphatidyl chloline, and peppermint oil.

Another embodiment comprises cyclosporin A, phosphatidyl chloline, and sunflower oil.

Another embodiment comprises cyclosporin A, phosphatidyl chloline, and eucalpytus oil.

Another embodiment comprises cyclosporin A, phosphatidyl chloline, and sesame oil.

Another embodiment comprises cyclosporin A, phosphatidyl chloline, and an oil having a specific gravity below 0.9.

Another embodiment comprises cyclosporin A, phosphatidyl chloline, and mineral oil.

Another embodiment comprises cyclosporin A, phosphatidyl chloline, and coriander oil.

Another embodiment comprises cyclosporin A, phosphatidyl chloline, and lavender oil.

Another embodiment comprises cyclosporin A, phosphatidyl chloline, and citronella oil.

Another embodiment comprises cyclosporin A, phosphatidyl chloline, and juniper oil.

Another embodiment comprises cyclosporin A, phosphatidyl chlorine, and lemon oil.

Another embodiment comprises cyclosporin A, phosphatidyl chloline, and orange oil.

Another embodiment comprises cyclosporin A, phosphatidyl chlorine, and clary sage oil.

Another embodiment comprises cyclosporin A, phosphatidyl chlorine, and nutmeg oil.

Another embodiment comprises cyclosporin A, phosphatidyl chloline, and tea tree oil.

Another embodiment comprises cyclosporin A, phosphatidyl serine, and an oil having a specific gravity between 0.90 and 0.95.

Another embodiment comprises cyclosporin A, phosphatidyl serine, and almond oil.

Another embodiment comprises cyclosporin A, phosphatidyl serine, and corn oil.

Another embodiment comprises cyclosporin A, phosphatidyl serine, and arachis oil.

Another embodiment comprises cyclosporin A, phosphatidyl serine, and cottonseed oil.

Another embodiment comprises cyclosporin A, phosphatidyl serine, and safflower oil.

Another embodiment comprises cyclosporin A, phosphatidyl serine, and maize oil.

Another embodiment comprises cyclosporin A, phosphatidyl serine, and linseed oil.

Another embodiment comprises cyclosporin A, phosphatidyl serine, and rapeseed oil.

Another embodiment comprises cyclosporin A, phosphatidyl serine, and soybean oil.

Another embodiment comprises cyclosporin A, phosphatidyl serine, and olive oil.

Another embodiment comprises cyclosporin A, phosphatidyl serine, and caraway oil.

Another embodiment comprises cyclosporin A, phosphatidyl serine, and rosemary oil.

Another embodiment comprises cyclosporin A, phosphatidyl serine, and peanut oil.

Another embodiment comprises cyclosporin A, phosphatidyl serine, and peppermint oil.

Another embodiment comprises cyclosporin A, phosphatidyl serine, and sunflower oil.

Another embodiment comprises cyclosporin A, phosphatidyl serine, and eucalpytus oil.

Another embodiment comprises cyclosporin A, phosphatidyl serine, and sesame oil.

Another embodiment comprises cyclosporin A, phosphatidyl serine, and an oil having a specific gravity below 0.9.

Another embodiment comprises cyclosporin A, phosphatidyl serine, and mineral oil.

Another embodiment comprises cyclosporin A, phosphatidyl serine, and coriander oil.

Another embodiment comprises cyclosporin A, phosphatidyl serine, and lavender oil.

Another embodiment comprises cyclosporin A, phosphatidyl serine, and citronella oil.

Another embodiment comprises cyclosporin A, phosphatidyl serine, and juniper oil.

Another embodiment comprises cyclosporin A, phosphatidyl serine, and lemon oil.

Another embodiment comprises cyclosporin A, phosphatidyl serine, and orange oil.

Another embodiment comprises cyclosporin A, phosphatidyl serine, and clary sage oil.

Another embodiment comprises cyclosporin A, phosphatidyl serine, and nutmeg oil.

Another embodiment comprises cyclosporin A, phosphatidyl serine, and tea tree oil.

Another embodiment comprises from about 0.005% to about 0.05% cyclosporin A, a sorbitan ester, and an oil having a specific gravity between 0.90 and 0.95.

Another embodiment comprises from about 0.005% to about 0.05% cyclosporin A, a sorbitan ester, and almond oil.

Another embodiment comprises from about 0.005% to about 0.05% cyclosporin A, a sorbitan ester, and corn oil.

Another embodiment comprises from about 0.005% to about 0.05% cyclosporin A, a sorbitan ester, and arachis oil.

Another embodiment comprises from about 0.005% to about 0.05% cyclosporin A, a sorbitan ester, and cottonseed oil.

Another embodiment comprises from about 0.005% to about 0.05% cyclosporin A, a sorbitan ester, and safflower oil.

Another embodiment comprises from about 0.005% to about 0.05% cyclosporin A, a sorbitan ester, and maize oil.

Another embodiment comprises from about 0.005% to about 0.05% cyclosporin A, a sorbitan ester, and linseed oil.

Another embodiment comprises from about 0.005% to about 0.05% cyclosporin A, a sorbitan ester, and rapeseed oil.

Another embodiment comprises from about 0.005% to about 0.05% cyclosporin A, a sorbitan ester, and soybean oil.

Another embodiment comprises from about 0.005% to about 0.05% cyclosporin A, a sorbitan ester, and olive oil.

Another embodiment comprises from about 0.005% to about 0.05% cyclosporin A, a sorbitan ester, and caraway oil.

Another embodiment comprises from about 0.005% to about 0.05% cyclosporin A, a sorbitan ester, and rosemary oil.

Another embodiment comprises from about 0.005% to about 0.05% cyclosporin A, a sorbitan ester, and peanut oil.

Another embodiment comprises from about 0.005% to about 0.05% cyclosporin A, a sorbitan ester, and peppermint oil.

Another embodiment comprises from about 0.005% to about 0.05% cyclosporin A, a sorbitan ester, and sunflower oil.

Another embodiment comprises from about 0.005% to about 0.05% cyclosporin A, a sorbitan ester, and eucalpytus oil.

Another embodiment comprises from about 0.005% to about 0.05% cyclosporin A, a sorbitan ester, and sesame oil.

Another embodiment comprises from about 0.005% to about 0.05% cyclosporin A, a sorbitan ester, and an oil having a specific gravity below 0.9.

Another embodiment comprises from about 0.005% to about 0.05% cyclosporin A, a sorbitan ester, and mineral oil.

Another embodiment comprises from about 0.005% to about 0.05% cyclosporin A, a sorbitan ester, and coriander oil.

Another embodiment comprises from about 0.005% to about 0.05% cyclosporin A, a sorbitan ester, and lavender oil.

Another embodiment comprises from about 0.005% to about 0.05% cyclosporin A, a sorbitan ester, and citronella oil.

Another embodiment comprises from about 0.005% to about 0.05% cyclosporin A, a sorbitan ester, and juniper oil.

Another embodiment comprises from about 0.005% to about 0.05% cyclosporin A, a sorbitan ester, and lemon oil.

Another embodiment comprises from about 0.005% to about 0.05% cyclosporin A, a sorbitan ester, and orange oil.

Another embodiment comprises from about 0.005% to about 0.05% cyclosporin A, a sorbitan ester, and clary sage oil.

Another embodiment comprises from about 0.005% to about 0.05% cyclosporin A, a sorbitan ester, and nutmeg oil.

Another embodiment comprises from about 0.005% to about 0.05% cyclosporin A, a sorbitan ester, and tea tree oil.

Another embodiment comprises from about 0.005% to about 0.05% cyclosporin A, Polysorbate 20, and an oil having a specific gravity between 0.90 and 0.95.

Another embodiment comprises from about 0.005% to about 0.05% cyclosporin A, Polysorbate 20, and almond oil.

Another embodiment comprises from about 0.005% to about 0.05% cyclosporin A, Polysorbate 20, and corn oil.

Another embodiment comprises from about 0.005% to about 0.05% cyclosporin A, Polysorbate 20, and arachis oil.

Another embodiment comprises from about 0.005% to about 0.05% cyclosporin A, Polysorbate 20, and cottonseed oil.

Another embodiment comprises from about 0.005% to about 0.05% cyclosporin A, Polysorbate 20, and safflower oil.

Another embodiment comprises from about 0.005% to about 0.05% cyclosporin A, Polysorbate 20, and maize oil.

Another embodiment comprises from about 0.005% to about 0.05% cyclosporin A, Polysorbate 20, and linseed oil.

Another embodiment comprises from about 0.005% to about 0.05% cyclosporin A, Polysorbate 20, and rapeseed oil.

Another embodiment comprises from about 0.005% to about 0.05% cyclosporin A, Polysorbate 20, and soybean oil.

Another embodiment comprises from about 0.005% to about 0.05% cyclosporin A, Polysorbate 20, and olive oil.

Another embodiment comprises from about 0.005% to about 0.05% cyclosporin A, Polysorbate 20, and caraway oil.

Another embodiment comprises from about 0.005% to about 0.05% cyclosporin A, Polysorbate 20, and rosemary oil.

Another embodiment comprises from about 0.005% to about 0.05% cyclosporin A, Polysorbate 20, and peanut oil.

Another embodiment comprises from about 0.005% to about 0.05% cyclosporin A, Polysorbate 20, and peppermint oil.

Another embodiment comprises from about 0.005% to about 0.05% cyclosporin A, Polysorbate 20, and sunflower oil.

Another embodiment comprises from about 0.005% to about 0.05% cyclosporin A, Polysorbate 20, and eucalpytus oil.

Another embodiment comprises from about 0.005% to about 0.05% cyclosporin A, Polysorbate 20, and sesame oil.

Another embodiment comprises from about 0.005% to about 0.05% cyclosporin A, Polysorbate 20, and an oil having a specific gravity below 0.9.

Another embodiment comprises from about 0.005% to about 0.05% cyclosporin A, Polysorbate 20, and mineral oil.

Another embodiment comprises from about 0.005% to about 0.05% cyclosporin A, Polysorbate 20, and coriander oil.

Another embodiment comprises from about 0.005% to about 0.05% cyclosporin A, Polysorbate 20, and lavender oil.

Another embodiment comprises from about 0.005% to about 0.05% cyclosporin A, Polysorbate 20, and citronella oil.

Another embodiment comprises from about 0.005% to about 0.05% cyclosporin A, Polysorbate 20, and juniper oil.

Another embodiment comprises from about 0.005% to about 0.05% cyclosporin A, Polysorbate 20, and lemon oil.

Another embodiment comprises from about 0.005% to about 0.05% cyclosporin A, Polysorbate 20, and orange oil.

Another embodiment comprises from about 0.005% to about 0.05% cyclosporin A, Polysorbate 20, and clary sage oil.

Another embodiment comprises from about 0.005% to about 0.05% cyclosporin A, Polysorbate 20, and nutmeg oil.

Another embodiment comprises from about 0.005% to about 0.05% cyclosporin A, Polysorbate 20, and tea tree oil.

Another embodiment comprises from about 0.005% to about 0.05% cyclosporin A, Polysorbate 40, and an oil having a specific gravity between 0.90 and 0.95.

Another embodiment comprises from about 0.005% to about 0.05% cyclosporin A, Polysorbate 40, and almond oil.

Another embodiment comprises from about 0.005% to about 0.05% cyclosporin A, Polysorbate 40, and corn oil.

Another embodiment comprises from about 0.005% to about 0.05% cyclosporin A, Polysorbate 40, and arachis oil.

Another embodiment comprises from about 0.005% to about 0.05% cyclosporin A, Polysorbate 40, and cottonseed oil.

Another embodiment comprises from about 0.005% to about 0.05% cyclosporin A, Polysorbate 40, and safflower oil.

Another embodiment comprises from about 0.005% to about 0.05% cyclosporin A, Polysorbate 40, and maize oil.

Another embodiment comprises from about 0.005% to about 0.05% cyclosporin A, Polysorbate 40, and linseed oil.

Another embodiment comprises from about 0.005% to about 0.05% cyclosporin A, Polysorbate 40, and rapeseed oil.

Another embodiment comprises from about 0.005% to about 0.05% cyclosporin A, Polysorbate 40, and soybean oil.

Another embodiment comprises from about 0.005% to about 0.05% cyclosporin A, Polysorbate 40, and olive oil.

Another embodiment comprises from about 0.005% to about 0.05% cyclosporin A, Polysorbate 40, and caraway oil.

Another embodiment comprises from about 0.005% to about 0.05% cyclosporin A, Polysorbate 40, and rosemary oil.

Another embodiment comprises from about 0.005% to about 0.05% cyclosporin A, Polysorbate 40, and peanut oil.

Another embodiment comprises from about 0.005% to about 0.05% cyclosporin A, Polysorbate 40, and peppermint oil.

Another embodiment comprises from about 0.005% to about 0.05% cyclosporin A, Polysorbate 40, and sunflower oil.

Another embodiment comprises from about 0.005% to about 0.05% cyclosporin A, Polysorbate 40, and eucalpytus oil.

Another embodiment comprises from about 0.005% to about 0.05% cyclosporin A, Polysorbate 40, and sesame oil.

Another embodiment comprises from about 0.005% to about 0.05% cyclosporin A, Polysorbate 40, and an oil having a specific gravity below 0.9.

Another embodiment comprises from about 0.005% to about 0.05% cyclosporin A, Polysorbate 40, and mineral oil.

Another embodiment comprises from about 0.005% to about 0.05% cyclosporin A, Polysorbate 40, and coriander oil.

Another embodiment comprises from about 0.005% to about 0.05% cyclosporin A, Polysorbate 40, and lavender oil.

Another embodiment comprises from about 0.005% to about 0.05% cyclosporin A, Polysorbate 40, and citronella oil.

Another embodiment comprises from about 0.005% to about 0.05% cyclosporin A, Polysorbate 40, and juniper oil.

Another embodiment comprises from about 0.005% to about 0.05% cyclosporin A, Polysorbate 40, and lemon oil.

Another embodiment comprises from about 0.005% to about 0.05% cyclosporin A, Polysorbate 40, and orange oil.

Another embodiment comprises from about 0.005% to about 0.05% cyclosporin A, Polysorbate 40, and clary sage oil.

Another embodiment comprises from about 0.005% to about 0.05% cyclosporin A, Polysorbate 40, and nutmeg oil.

Another embodiment comprises from about 0.005% to about 0.05% cyclosporin A, Polysorbate 40, and tea tree oil.

Another embodiment comprises from about 0.005% to about 0.05% cyclosporin A, Polysorbate 60, and an oil having a specific gravity between 0.90 and 0.95.

Another embodiment comprises from about 0.005% to about 0.05% cyclosporin A, Polysorbate 60, and almond oil.

Another embodiment comprises from about 0.005% to about 0.05% cyclosporin A, Polysorbate 60, and corn oil.

Another embodiment comprises from about 0.005% to about 0.05% cyclosporin A, Polysorbate 60, and arachis oil.

Another embodiment comprises from about 0.005% to about 0.05% cyclosporin A, Polysorbate 60, and cottonseed oil.

Another embodiment comprises from about 0.005% to about 0.05% cyclosporin A, Polysorbate 60, and safflower oil.

Another embodiment comprises from about 0.005% to about 0.05% cyclosporin A, Polysorbate 60, and maize oil.

Another embodiment comprises from about 0.005% to about 0.05% cyclosporin A, Polysorbate 60, and linseed oil.

Another embodiment comprises from about 0.005% to about 0.05% cyclosporin A, Polysorbate 60, and rapeseed oil.

Another embodiment comprises from about 0.005% to about 0.05% cyclosporin A, Polysorbate 60, and soybean oil.

Another embodiment comprises from about 0.005% to about 0.05% cyclosporin A, Polysorbate 60, and olive oil.

Another embodiment comprises from about 0.005% to about 0.05% cyclosporin A, Polysorbate 60, and caraway oil.

Another embodiment comprises from about 0.005% to about 0.05% cyclosporin A, Polysorbate 60, and rosemary oil.

Another embodiment comprises from about 0.005% to about 0.05% cyclosporin A, Polysorbate 60, and peanut oil.

Another embodiment comprises from about 0.005% to about 0.05% cyclosporin A, Polysorbate 60, and peppermint oil.

Another embodiment comprises from about 0.005% to about 0.05% cyclosporin A, Polysorbate 60, and sunflower oil.

Another embodiment comprises from about 0.005% to about 0.05% cyclosporin A, Polysorbate 60, and eucalpytus oil.

Another embodiment comprises from about 0.005% to about 0.05% cyclosporin A, Polysorbate 60, and sesame oil.

Another embodiment comprises from about 0.005% to about 0.05% cyclosporin A, Polysorbate 60, and an oil having a specific gravity below 0.9.

Another embodiment comprises from about 0.005% to about 0.05% cyclosporin A, Polysorbate 60, and mineral oil.

Another embodiment comprises from about 0.005% to about 0.05% cyclosporin A, Polysorbate 60, and coriander oil.

Another embodiment comprises from about 0.005% to about 0.05% cyclosporin A, Polysorbate 60, and lavender oil.

Another embodiment comprises from about 0.005% to about 0.05% cyclosporin A, Polysorbate 60, and citronella oil.

Another embodiment comprises from about 0.005% to about 0.05% cyclosporin A, Polysorbate 60, and juniper oil.

Another embodiment comprises from about 0.005% to about 0.05% cyclosporin A, Polysorbate 60, and lemon oil.

Another embodiment comprises from about 0.005% to about 0.05% cyclosporin A, Polysorbate 60, and orange oil.

Another embodiment comprises from about 0.005% to about 0.05% cyclosporin A, Polysorbate 60, and clary sage oil.

Another embodiment comprises from about 0.005% to about 0.05% cyclosporin A, Polysorbate 60, and nutmeg oil.

Another embodiment comprises from about 0.005% to about 0.05% cyclosporin A, Polysorbate 60, and tea tree oil.

Another embodiment comprises from about 0.005% to about 0.05% cyclosporin A, Polysorbate 80, and an oil having a specific gravity between 0.90 and 0.95.

Another embodiment comprises from about 0.005% to about 0.05% cyclosporin A, Polysorbate 80, and almond oil.

Another embodiment comprises from about 0.005% to about 0.05% cyclosporin A, Polysorbate 80, and corn oil.

Another embodiment comprises from about 0.005% to about 0.05% cyclosporin A, Polysorbate 80, and arachis oil.

Another embodiment comprises from about 0.005% to about 0.05% cyclosporin A, Polysorbate 80, and cottonseed oil.

Another embodiment comprises from about 0.005% to about 0.05% cyclosporin A, Polysorbate 80, and safflower oil.

Another embodiment comprises from about 0.005% to about 0.05% cyclosporin A, Polysorbate 80, and maize oil.

Another embodiment comprises from about 0.005% to about 0.05% cyclosporin A, Polysorbate 80, and linseed oil.

Another embodiment comprises from about 0.005% to about 0.05% cyclosporin A, Polysorbate 80, and rapeseed oil.

Another embodiment comprises from about 0.005% to about 0.05% cyclosporin A, Polysorbate 80, and soybean oil.

Another embodiment comprises from about 0.005% to about 0.05% cyclosporin A, Polysorbate 80, and olive oil.

Another embodiment comprises from about 0.005% to about 0.05% cyclosporin A, Polysorbate 80, and caraway oil.

Another embodiment comprises from about 0.005% to about 0.05% cyclosporin A, Polysorbate 80, and rosemary oil.

Another embodiment comprises from about 0.005% to about 0.05% cyclosporin A, Polysorbate 80, and peanut oil.

Another embodiment comprises from about 0.005% to about 0.05% cyclosporin A, Polysorbate 80, and peppermint oil.

Another embodiment comprises from about 0.005% to about 0.05% cyclosporin A, Polysorbate 80, and sunflower oil.

Another embodiment comprises from about 0.005% to about 0.05% cyclosporin A, Polysorbate 80, and eucalpytus oil.

Another embodiment comprises from about 0.005% to about 0.05% cyclosporin A, Polysorbate 80, and sesame oil.

Another embodiment comprises from about 0.005% to about 0.05% cyclosporin A, Polysorbate 80, and an oil having a specific gravity below 0.9.

Another embodiment comprises from about 0.005% to about 0.05% cyclosporin A, Polysorbate 80, and mineral oil.

Another embodiment comprises from about 0.005% to about 0.05% cyclosporin A, Polysorbate 80, and coriander oil.

Another embodiment comprises from about 0.005% to about 0.05% cyclosporin A, Polysorbate 80, and lavender oil.

Another embodiment comprises from about 0.005% to about 0.05% cyclosporin A, Polysorbate 80, and citronella oil.

Another embodiment comprises from about 0.005% to about 0.05% cyclosporin A, Polysorbate 80, and juniper oil.

Another embodiment comprises from about 0.005% to about 0.05% cyclosporin A, Polysorbate 80, and lemon oil.

Another embodiment comprises from about 0.005% to about 0.05% cyclosporin A, Polysorbate 80, and orange oil.

Another embodiment comprises from about 0.005% to about 0.05% cyclosporin A, Polysorbate 80, and clary sage oil.

Another embodiment comprises from about 0.005% to about 0.05% cyclosporin A, Polysorbate 80, and nutmeg oil.

Another embodiment comprises from about 0.005% to about 0.05% cyclosporin A, Polysorbate 80, and tea tree oil.

Another embodiment comprises from about 0.005% to about 0.05% cyclosporin A, a stearate, and an oil having a specific gravity between 0.90 and 0.95.

Another embodiment comprises from about 0.005% to about 0.05% cyclosporin A, a stearate, and almond oil.

Another embodiment comprises from about 0.005% to about 0.05% cyclosporin A, a stearate, and corn oil.

Another embodiment comprises from about 0.005% to about 0.05% cyclosporin A, a stearate, and arachis oil.

Another embodiment comprises from about 0.005% to about 0.05% cyclosporin A, a stearate, and cottonseed oil.

Another embodiment comprises from about 0.005% to about 0.05% cyclosporin A, a stearate, and safflower oil.

Another embodiment comprises from about 0.005% to about 0.05% cyclosporin A, a stearate, and maize oil.

Another embodiment comprises from about 0.005% to about 0.05% cyclosporin A, a stearate, and linseed oil.

Another embodiment comprises from about 0.005% to about 0.05% cyclosporin A, a stearate, and rapeseed oil.

Another embodiment comprises from about 0.005% to about 0.05% cyclosporin A, a stearate, and soybean oil.

Another embodiment comprises from about 0.005% to about 0.05% cyclosporin A, a stearate, and olive oil.

Another embodiment comprises from about 0.005% to about 0.05% cyclosporin A, a stearate, and caraway oil.

Another embodiment comprises from about 0.005% to about 0.05% cyclosporin A, a stearate, and rosemary oil.

Another embodiment comprises from about 0.005% to about 0.05% cyclosporin A, a stearate, and peanut oil.

Another embodiment comprises from about 0.005% to about 0.05% cyclosporin A, a stearate, and peppermint oil.

Another embodiment comprises from about 0.005% to about 0.05% cyclosporin A, a stearate, and sunflower oil.

Another embodiment comprises from about 0.005% to about 0.05% cyclosporin A, a stearate, and eucalpytus oil.

Another embodiment comprises from about 0.005% to about 0.05% cyclosporin A, a stearate, and sesame oil.

Another embodiment comprises from about 0.005% to about 0.05% cyclosporin A, a stearate, and an oil having a specific gravity below 0.9.

Another embodiment comprises from about 0.005% to about 0.05% cyclosporin A, a stearate, and mineral oil.

Another embodiment comprises from about 0.005% to about 0.05% cyclosporin A, a stearate, and coriander oil.

Another embodiment comprises from about 0.005% to about 0.05% cyclosporin A, a stearate, and lavender oil.

Another embodiment comprises from about 0.005% to about 0.05% cyclosporin A, a stearate, and citronella oil.

Another embodiment comprises from about 0.005% to about 0.05% cyclosporin A, a stearate, and juniper oil.

Another embodiment comprises from about 0.005% to about 0.05% cyclosporin A, a stearate, and lemon oil.

Another embodiment comprises from about 0.005% to about 0.05% cyclosporin A, a stearate, and orange oil.

Another embodiment comprises from about 0.005% to about 0.05% cyclosporin A, a stearate, and clary sage oil.

Another embodiment comprises from about 0.005% to about 0.05% cyclosporin A, a stearate, and nutmeg oil.

Another embodiment comprises from about 0.005% to about 0.05% cyclosporin A, a stearate, and tea tree oil.

Another embodiment comprises from about 0.005% to about 0.05% cyclosporin A, glyceryl stearate, and an oil having a specific gravity between 0.90 and 0.95.

Another embodiment comprises from about 0.005% to about 0.05% cyclosporin A, glyceryl stearate, and almond oil.

Another embodiment comprises from about 0.005% to about 0.05% cyclosporin A, glyceryl stearate, and corn oil.

Another embodiment comprises from about 0.005% to about 0.05% cyclosporin A, glyceryl stearate, and arachis oil.

Another embodiment comprises from about 0.005% to about 0.05% cyclosporin A, glyceryl stearate, and cottonseed oil.

Another embodiment comprises from about 0.005% to about 0.05% cyclosporin A, glyceryl stearate, and safflower oil.

Another embodiment comprises from about 0.005% to about 0.05% cyclosporin A, glyceryl stearate, and maize oil.

Another embodiment comprises from about 0.005% to about 0.05% cyclosporin A, glyceryl stearate, and linseed oil.

Another embodiment comprises from about 0.005% to about 0.05% cyclosporin A, glyceryl stearate, and rapeseed oil.

Another embodiment comprises from about 0.005% to about 0.05% cyclosporin A, glyceryl stearate, and soybean oil.

Another embodiment comprises from about 0.005% to about 0.05% cyclosporin A, glyceryl stearate, and olive oil.

Another embodiment comprises from about 0.005% to about 0.05% cyclosporin A, glyceryl stearate, and caraway oil.

Another embodiment comprises from about 0.005% to about 0.05% cyclosporin A, glyceryl stearate, and rosemary oil.

Another embodiment comprises from about 0.005% to about 0.05% cyclosporin A, glyceryl stearate, and peanut oil.

Another embodiment comprises from about 0.005% to about 0.05% cyclosporin A, glyceryl stearate, and peppermint oil.

Another embodiment comprises from about 0.005% to about 0.05% cyclosporin A, glyceryl stearate, and sunflower oil.

Another embodiment comprises from about 0.005% to about 0.05% cyclosporin A, glyceryl stearate, and eucalpytus oil.

Another embodiment comprises from about 0.005% to about 0.05% cyclosporin A, glyceryl stearate, and sesame oil.

Another embodiment comprises from about 0.005% to about 0.05% cyclosporin A, glyceryl stearate, and an oil having a specific gravity below 0.9.

Another embodiment comprises from about 0.005% to about 0.05% cyclosporin A, glyceryl stearate, and mineral oil.

Another embodiment comprises from about 0.005% to about 0.05% cyclosporin A, glyceryl stearate, and coriander oil.

Another embodiment comprises from about 0.005% to about 0.05% cyclosporin A, glyceryl stearate, and lavender oil.

Another embodiment comprises from about 0.005% to about 0.05% cyclosporin A, glyceryl stearate, and citronella oil.

Another embodiment comprises from about 0.005% to about 0.05% cyclosporin A, glyceryl stearate, and juniper oil.

Another embodiment comprises from about 0.005% to about 0.05% cyclosporin A, glyceryl stearate, and lemon oil.

Another embodiment comprises from about 0.005% to about 0.05% cyclosporin A, glyceryl stearate, and orange oil.

Another embodiment comprises from about 0.005% to about 0.05% cyclosporin A, glyceryl stearate, and clary sage oil.

Another embodiment comprises from about 0.005% to about 0.05% cyclosporin A, glyceryl stearate, and nutmeg oil.

Another embodiment comprises from about 0.005% to about 0.05% cyclosporin A, glyceryl stearate, and tea tree oil.

Another embodiment comprises from about 0.005% to about 0.05% cyclosporin A, isopropyl stearate, and an oil having a specific gravity between 0.90 and 0.95.

Another embodiment comprises from about 0.005% to about 0.05% cyclosporin A, isopropyl stearate, and almond oil.

Another embodiment comprises from about 0.005% to about 0.05% cyclosporin A, isopropyl stearate, and corn oil.

Another embodiment comprises from about 0.005% to about 0.05% cyclosporin A, isopropyl stearate, and arachis oil.

Another embodiment comprises from about 0.005% to about 0.05% cyclosporin A, isopropyl stearate, and cottonseed oil.

Another embodiment comprises from about 0.005% to about 0.05% cyclosporin A, isopropyl stearate, and safflower oil.

Another embodiment comprises from about 0.005% to about 0.05% cyclosporin A, isopropyl stearate, and maize oil.

Another embodiment comprises from about 0.005% to about 0.05% cyclosporin A, isopropyl stearate, and linseed oil.

Another embodiment comprises from about 0.005% to about 0.05% cyclosporin A, isopropyl stearate, and rapeseed oil.

Another embodiment comprises from about 0.005% to about 0.05% cyclosporin A, isopropyl stearate, and soybean oil.

Another embodiment comprises from about 0.005% to about 0.05% cyclosporin A, isopropyl stearate, and olive oil.

Another embodiment comprises from about 0.005% to about 0.05% cyclosporin A, isopropyl stearate, and caraway oil.

Another embodiment comprises from about 0.005% to about 0.05% cyclosporin A, isopropyl stearate, and rosemary oil.

Another embodiment comprises from about 0.005% to about 0.05% cyclosporin A, isopropyl stearate, and peanut oil.

Another embodiment comprises from about 0.005% to about 0.05% cyclosporin A, isopropyl stearate, and peppermint oil.

Another embodiment comprises from about 0.005% to about 0.05% cyclosporin A, isopropyl stearate, and sunflower oil.

Another embodiment comprises from about 0.005% to about 0.05% cyclosporin A, isopropyl stearate, and eucalpytus oil.

Another embodiment comprises from about 0.005% to about 0.05% cyclosporin A, isopropyl stearate, and sesame oil.

Another embodiment comprises from about 0.005% to about 0.05% cyclosporin A, isopropyl stearate, and an oil having a specific gravity below 0.9.

Another embodiment comprises from about 0.005% to about 0.05% cyclosporin A, isopropyl stearate, and mineral oil.

Another embodiment comprises from about 0.005% to about 0.05% cyclosporin A, isopropyl stearate, and coriander oil.

Another embodiment comprises from about 0.005% to about 0.05% cyclosporin A, isopropyl stearate, and lavender oil.

Another embodiment comprises from about 0.005% to about 0.05% cyclosporin A, isopropyl stearate, and citronella oil.

Another embodiment comprises from about 0.005% to about 0.05% cyclosporin A, isopropyl stearate, and juniper oil.

Another embodiment comprises from about 0.005% to about 0.05% cyclosporin A, isopropyl stearate, and lemon oil.

Another embodiment comprises from about 0.005% to about 0.05% cyclosporin A, isopropyl stearate, and orange oil.

Another embodiment comprises from about 0.005% to about 0.05% cyclosporin A, isopropyl stearate, and clary sage oil.

Another embodiment comprises from about 0.005% to about 0.05% cyclosporin A, isopropyl stearate, and nutmeg oil.

Another embodiment comprises from about 0.005% to about 0.05% cyclosporin A, isopropyl stearate, and tea tree oil.

Another embodiment comprises from about 0.005% to about 0.05% cyclosporin A, polyoxyl stearate, and an oil having a specific gravity between 0.90 and 0.95.

Another embodiment comprises from about 0.005% to about 0.05% cyclosporin A, polyoxyl stearate, and almond oil.

Another embodiment comprises from about 0.005% to about 0.05% cyclosporin A, polyoxyl stearate, and corn oil.

Another embodiment comprises from about 0.005% to about 0.05% cyclosporin A, polyoxyl stearate, and arachis oil.

Another embodiment comprises from about 0.005% to about 0.05% cyclosporin A, polyoxyl stearate, and cottonseed oil.

Another embodiment comprises from about 0.005% to about 0.05% cyclosporin A, polyoxyl stearate, and safflower oil.

Another embodiment comprises from about 0.005% to about 0.05% cyclosporin A, polyoxyl stearate, and maize oil.

Another embodiment comprises from about 0.005% to about 0.05% cyclosporin A, polyoxyl stearate, and linseed oil.

Another embodiment comprises from about 0.005% to about 0.05% cyclosporin A, polyoxyl stearate, and rapeseed oil.

Another embodiment comprises from about 0.005% to about 0.05% cyclosporin A, polyoxyl stearate, and soybean oil.

Another embodiment comprises from about 0.005% to about 0.05% cyclosporin A, polyoxyl stearate, and olive oil.

Another embodiment comprises from about 0.005% to about 0.05% cyclosporin A, polyoxyl stearate, and caraway oil.

Another embodiment comprises from about 0.005% to about 0.05% cyclosporin A, polyoxyl stearate, and rosemary oil.

Another embodiment comprises from about 0.005% to about 0.05% cyclosporin A, polyoxyl stearate, and peanut oil.

Another embodiment comprises from about 0.005% to about 0.05% cyclosporin A, polyoxyl stearate, and peppermint oil.

Another embodiment comprises from about 0.005% to about 0.05% cyclosporin A, polyoxyl stearate, and sunflower oil.

Another embodiment comprises from about 0.005% to about 0.05% cyclosporin A, polyoxyl stearate, and eucalpytus oil.

Another embodiment comprises from about 0.005% to about 0.05% cyclosporin A, polyoxyl stearate, and sesame oil.

Another embodiment comprises from about 0.005% to about 0.05% cyclosporin A, polyoxyl stearate, and an oil having a specific gravity below 0.9.

Another embodiment comprises from about 0.005% to about 0.05% cyclosporin A, polyoxyl stearate, and mineral oil.

Another embodiment comprises from about 0.005% to about 0.05% cyclosporin A, polyoxyl stearate, and coriander oil.

Another embodiment comprises from about 0.005% to about 0.05% cyclosporin A, polyoxyl stearate, and lavender oil.

Another embodiment comprises from about 0.005% to about 0.05% cyclosporin A, polyoxyl stearate, and citronella oil.

Another embodiment comprises from about 0.005% to about 0.05% cyclosporin A, polyoxyl stearate, and juniper oil.

Another embodiment comprises from about 0.005% to about 0.05% cyclosporin A, polyoxyl stearate, and lemon oil.

Another embodiment comprises from about 0.005% to about 0.05% cyclosporin A, polyoxyl stearate, and orange oil.

Another embodiment comprises from about 0.005% to about 0.05% cyclosporin A, polyoxyl stearate, and clary sage oil.

Another embodiment comprises from about 0.005% to about 0.05% cyclosporin A, polyoxyl stearate, and nutmeg oil.

Another embodiment comprises from about 0.005% to about 0.05% cyclosporin A, polyoxyl stearate, and tea tree oil.

Another embodiment comprises from about 0.005% to about 0.05% cyclosporin A, propylene glycol stearate, and an oil having a specific gravity between 0.90 and 0.95.

Another embodiment comprises from about 0.005% to about 0.05% cyclosporin A, propylene glycol stearate, and almond oil.

Another embodiment comprises from about 0.005% to about 0.05% cyclosporin A, propylene glycol stearate, and corn oil.

Another embodiment comprises from about 0.005% to about 0.05% cyclosporin A, propylene glycol stearate, and arachis oil.

Another embodiment comprises from about 0.005% to about 0.05% cyclosporin A, propylene glycol stearate, and cottonseed oil.

Another embodiment comprises from about 0.005% to about 0.05% cyclosporin A, propylene glycol stearate, and safflower oil.

Another embodiment comprises from about 0.005% to about 0.05% cyclosporin A, propylene glycol stearate, and maize oil.

Another embodiment comprises from about 0.005% to about 0.05% cyclosporin A, propylene glycol stearate, and linseed oil.

Another embodiment comprises from about 0.005% to about 0.05% cyclosporin A, propylene glycol stearate, and rapeseed oil.

Another embodiment comprises from about 0.005% to about 0.05% cyclosporin A, propylene glycol stearate, and soybean oil.

Another embodiment comprises from about 0.005% to about 0.05% cyclosporin A, propylene glycol stearate, and olive oil.

Another embodiment comprises from about 0.005% to about 0.05% cyclosporin A, propylene glycol stearate, and caraway oil.

Another embodiment comprises from about 0.005% to about 0.05% cyclosporin A, propylene glycol stearate, and rosemary oil.

Another embodiment comprises from about 0.005% to about 0.05% cyclosporin A, propylene glycol stearate, and peanut oil.

Another embodiment comprises from about 0.005% to about 0.05% cyclosporin A, propylene glycol stearate, and peppermint oil.

Another embodiment comprises from about 0.005% to about 0.05% cyclosporin A, propylene glycol stearate, and sunflower oil.

Another embodiment comprises from about 0.005% to about 0.05% cyclosporin A, propylene glycol stearate, and eucalpytus oil.

Another embodiment comprises from about 0.005% to about 0.05% cyclosporin A, propylene glycol stearate, and sesame oil.

Another embodiment comprises from about 0.005% to about 0.05% cyclosporin A, propylene glycol stearate, and an oil having a specific gravity below 0.9.

Another embodiment comprises from about 0.005% to about 0.05% cyclosporin A, propylene glycol stearate, and mineral oil.

Another embodiment comprises from about 0.005% to about 0.05% cyclosporin A, propylene glycol stearate, and coriander oil.

Another embodiment comprises from about 0.005% to about 0.05% cyclosporin A, propylene glycol stearate, and lavender oil.

Another embodiment comprises from about 0.005% to about 0.05% cyclosporin A, propylene glycol stearate, and citronella oil.

Another embodiment comprises from about 0.005% to about 0.05% cyclosporin A, propylene glycol stearate, and juniper oil.

Another embodiment comprises from about 0.005% to about 0.05% cyclosporin A, propylene glycol stearate, and lemon oil.

Another embodiment comprises from about 0.005% to about 0.05% cyclosporin A, propylene glycol stearate, and orange oil.

Another embodiment comprises from about 0.005% to about 0.05% cyclosporin A, propylene glycol stearate, and clary sage oil.

Another embodiment comprises from about 0.005% to about 0.05% cyclosporin A, propylene glycol stearate, and nutmeg oil.

Another embodiment comprises from about 0.005% to about 0.05% cyclosporin A, propylene glycol stearate, and tea tree oil.

Another embodiment comprises from about 0.005% to about 0.05% cyclosporin A, sucrose stearate, and an oil having a specific gravity between 0.90 and 0.95.

Another embodiment comprises from about 0.005% to about 0.05% cyclosporin A, sucrose stearate, and almond oil.

Another embodiment comprises from about 0.005% to about 0.05% cyclosporin A, sucrose stearate, and corn oil.

Another embodiment comprises from about 0.005% to about 0.05% cyclosporin A, sucrose stearate, and arachis oil.

Another embodiment comprises from about 0.005% to about 0.05% cyclosporin A, sucrose stearate, and cottonseed oil.

Another embodiment comprises from about 0.005% to about 0.05% cyclosporin A, sucrose stearate, and safflower oil.

Another embodiment comprises from about 0.005% to about 0.05% cyclosporin A, sucrose stearate, and maize oil.

Another embodiment comprises from about 0.005% to about 0.05% cyclosporin A, sucrose stearate, and linseed oil.

Another embodiment comprises from about 0.005% to about 0.05% cyclosporin A, sucrose stearate, and rapeseed oil.

Another embodiment comprises from about 0.005% to about 0.05% cyclosporin A, sucrose stearate, and soybean oil.

Another embodiment comprises from about 0.005% to about 0.05% cyclosporin A, sucrose stearate, and olive oil.

Another embodiment comprises from about 0.005% to about 0.05% cyclosporin A, sucrose stearate, and caraway oil.

Another embodiment comprises from about 0.005% to about 0.05% cyclosporin A, sucrose stearate, and rosemary oil.

Another embodiment comprises from about 0.005% to about 0.05% cyclosporin A, sucrose stearate, and peanut oil.

Another embodiment comprises from about 0.005% to about 0.05% cyclosporin A, sucrose stearate, and peppermint oil.

Another embodiment comprises from about 0.005% to about 0.05% cyclosporin A, sucrose stearate, and sunflower oil.

Another embodiment comprises from about 0.005% to about 0.05% cyclosporin A, sucrose stearate, and eucalpytus oil.

Another embodiment comprises from about 0.005% to about 0.05% cyclosporin A, sucrose stearate, and sesame oil.

Another embodiment comprises from about 0.005% to about 0.05% cyclosporin A, sucrose stearate, and an oil having a specific gravity below 0.9.

Another embodiment comprises from about 0.005% to about 0.05% cyclosporin A, sucrose stearate, and mineral oil.

Another embodiment comprises from about 0.005% to about 0.05% cyclosporin A, sucrose stearate, and coriander oil.

Another embodiment comprises from about 0.005% to about 0.05% cyclosporin A, sucrose stearate, and lavender oil.

Another embodiment comprises from about 0.005% to about 0.05% cyclosporin A, sucrose stearate, and citronella oil.

Another embodiment comprises from about 0.005% to about 0.05% cyclosporin A, sucrose stearate, and juniper oil.

Another embodiment comprises from about 0.005% to about 0.05% cyclosporin A, sucrose stearate, and lemon oil.

Another embodiment comprises from about 0.005% to about 0.05% cyclosporin A, sucrose stearate, and orange oil.

Another embodiment comprises from about 0.005% to about 0.05% cyclosporin A, sucrose stearate, and clary sage oil.

Another embodiment comprises from about 0.005% to about 0.05% cyclosporin A, sucrose stearate, and nutmeg oil.

Another embodiment comprises from about 0.005% to about 0.05% cyclosporin A, sucrose stearate, and tea tree oil.

Another embodiment comprises from about 0.005% to about 0.05% cyclosporin A, polyethylene glycol, and an oil having a specific gravity between 0.90 and 0.95.

Another embodiment comprises from about 0.005% to about 0.05% cyclosporin A, polyethylene glycol, and almond oil.

Another embodiment comprises from about 0.005% to about 0.05% cyclosporin A, polyethylene glycol, and corn oil.

Another embodiment comprises from about 0.005% to about 0.05% cyclosporin A, polyethylene glycol, and arachis oil.

Another embodiment comprises from about 0.005% to about 0.05% cyclosporin A, polyethylene glycol, and cottonseed oil.

Another embodiment comprises from about 0.005% to about 0.05% cyclosporin A, polyethylene glycol, and safflower oil.

Another embodiment comprises from about 0.005% to about 0.05% cyclosporin A, polyethylene glycol, and maize oil.

Another embodiment comprises from about 0.005% to about 0.05% cyclosporin A, polyethylene glycol, and linseed oil.

Another embodiment comprises from about 0.005% to about 0.05% cyclosporin A, polyethylene glycol, and rapeseed oil.

Another embodiment comprises from about 0.005% to about 0.05% cyclosporin A, polyethylene glycol, and soybean oil.

Another embodiment comprises from about 0.005% to about 0.05% cyclosporin A, polyethylene glycol, and olive oil.

Another embodiment comprises from about 0.005% to about 0.05% cyclosporin A, polyethylene glycol, and caraway oil.

Another embodiment comprises from about 0.005% to about 0.05% cyclosporin A, polyethylene glycol, and rosemary oil.

Another embodiment comprises from about 0.005% to about 0.05% cyclosporin A, polyethylene glycol, and peanut oil.

Another embodiment comprises from about 0.005% to about 0.05% cyclosporin A, polyethylene glycol, and peppermint oil.

Another embodiment comprises from about 0.005% to about 0.05% cyclosporin A, polyethylene glycol, and sunflower oil.

Another embodiment comprises from about 0.005% to about 0.05% cyclosporin A, polyethylene glycol, and eucalpytus oil.

Another embodiment comprises from about 0.005% to about 0.05% cyclosporin A, polyethylene glycol, and sesame oil.

Another embodiment comprises from about 0.005% to about 0.05% cyclosporin A, polyethylene glycol, and an oil having a specific gravity below 0.9.

Another embodiment comprises from about 0.005% to about 0.05% cyclosporin A, polyethylene glycol, and mineral oil.

Another embodiment comprises from about 0.005% to about 0.05% cyclosporin A, polyethylene glycol, and coriander oil.

Another embodiment comprises from about 0.005% to about 0.05% cyclosporin A, polyethylene glycol, and lavender oil.

Another embodiment comprises from about 0.005% to about 0.05% cyclosporin A, polyethylene glycol, and citronella oil.

Another embodiment comprises from about 0.005% to about 0.05% cyclosporin A, polyethylene glycol, and juniper oil.

Another embodiment comprises from about 0.005% to about 0.05% cyclosporin A, polyethylene glycol, and lemon oil.

Another embodiment comprises from about 0.005% to about 0.05% cyclosporin A, polyethylene glycol, and orange oil.

Another embodiment comprises from about 0.005% to about 0.05% cyclosporin A, polyethylene glycol, and clary sage oil.

Another embodiment comprises from about 0.005% to about 0.05% cyclosporin A, polyethylene glycol, and nutmeg oil.

Another embodiment comprises from about 0.005% to about 0.05% cyclosporin A, polyethylene glycol, and tea tree oil.

Another embodiment comprises from about 0.005% to about 0.05% cyclosporin A, polyethylene oxide, and an oil having a specific gravity between 0.90 and 0.95.

Another embodiment comprises from about 0.005% to about 0.05% cyclosporin A, polyethylene oxide, and almond oil.

Another embodiment comprises from about 0.005% to about 0.05% cyclosporin A, polyethylene oxide, and corn oil.

Another embodiment comprises from about 0.005% to about 0.05% cyclosporin A, polyethylene oxide, and arachis oil.

Another embodiment comprises from about 0.005% to about 0.05% cyclosporin A, polyethylene oxide, and cottonseed oil.

Another embodiment comprises from about 0.005% to about 0.05% cyclosporin A, polyethylene oxide, and safflower oil.

Another embodiment comprises from about 0.005% to about 0.05% cyclosporin A, polyethylene oxide, and maize oil.

Another embodiment comprises from about 0.005% to about 0.05% cyclosporin A, polyethylene oxide, and linseed oil.

Another embodiment comprises from about 0.005% to about 0.05% cyclosporin A, polyethylene oxide, and rapeseed oil.

Another embodiment comprises from about 0.005% to about 0.05% cyclosporin A, polyethylene oxide, and soybean oil.

Another embodiment comprises from about 0.005% to about 0.05% cyclosporin A, polyethylene oxide, and olive oil.

Another embodiment comprises from about 0.005% to about 0.05% cyclosporin A, polyethylene oxide, and caraway oil.

Another embodiment comprises from about 0.005% to about 0.05% cyclosporin A, polyethylene oxide, and rosemary oil.

Another embodiment comprises from about 0.005% to about 0.05% cyclosporin A, polyethylene oxide, and peanut oil.

Another embodiment comprises from about 0.005% to about 0.05% cyclosporin A, polyethylene oxide, and peppermint oil.

Another embodiment comprises from about 0.005% to about 0.05% cyclosporin A, polyethylene oxide, and sunflower oil.

Another embodiment comprises from about 0.005% to about 0.05% cyclosporin A, polyethylene oxide, and eucalpytus oil.

Another embodiment comprises from about 0.005% to about 0.05% cyclosporin A, polyethylene oxide, and sesame oil.

Another embodiment comprises from about 0.005% to about 0.05% cyclosporin A, polyethylene oxide, and an oil having a specific gravity below 0.9.

Another embodiment comprises from about 0.005% to about 0.05% cyclosporin A, polyethylene oxide, and mineral oil.

Another embodiment comprises from about 0.005% to about 0.05% cyclosporin A, polyethylene oxide, and coriander oil.

Another embodiment comprises from about 0.005% to about 0.05% cyclosporin A, polyethylene oxide, and lavender oil.

Another embodiment comprises from about 0.005% to about 0.05% cyclosporin A, polyethylene oxide, and citronella oil.

Another embodiment comprises from about 0.005% to about 0.05% cyclosporin A, polyethylene oxide, and juniper oil.

Another embodiment comprises from about 0.005% to about 0.05% cyclosporin A, polyethylene oxide, and lemon oil.

Another embodiment comprises from about 0.005% to about 0.05% cyclosporin A, polyethylene oxide, and orange oil.

Another embodiment comprises from about 0.005% to about 0.05% cyclosporin A, polyethylene oxide, and clary sage oil.

Another embodiment comprises from about 0.005% to about 0.05% cyclosporin A, polyethylene oxide, and nutmeg oil.

Another embodiment comprises from about 0.005% to about 0.05% cyclosporin A, polyethylene oxide, and tea tree oil.

Another embodiment comprises from about 0.005% to about 0.05% cyclosporin A, polypropylene oxide, and an oil having a specific gravity between 0.90 and 0.95.

Another embodiment comprises from about 0.005% to about 0.05% cyclosporin A, polypropylene oxide, and almond oil.

Another embodiment comprises from about 0.005% to about 0.05% cyclosporin A, polypropylene oxide, and corn oil.

Another embodiment comprises from about 0.005% to about 0.05% cyclosporin A, polypropylene oxide, and arachis oil.

Another embodiment comprises from about 0.005% to about 0.05% cyclosporin A, polypropylene oxide, and cottonseed oil.

Another embodiment comprises from about 0.005% to about 0.05% cyclosporin A, polypropylene oxide, and safflower oil.

Another embodiment comprises from about 0.005% to about 0.05% cyclosporin A, polypropylene oxide, and maize oil.

Another embodiment comprises from about 0.005% to about 0.05% cyclosporin A, polypropylene oxide, and linseed oil.

Another embodiment comprises from about 0.005% to about 0.05% cyclosporin A, polypropylene oxide, and rapeseed oil.

Another embodiment comprises from about 0.005% to about 0.05% cyclosporin A, polypropylene oxide, and soybean oil.

Another embodiment comprises from about 0.005% to about 0.05% cyclosporin A, polypropylene oxide, and olive oil.

Another embodiment comprises from about 0.005% to about 0.05% cyclosporin A, polypropylene oxide, and caraway oil.

Another embodiment comprises from about 0.005% to about 0.05% cyclosporin A, polypropylene oxide, and rosemary oil.

Another embodiment comprises from about 0.005% to about 0.05% cyclosporin A, polypropylene oxide, and peanut oil.

Another embodiment comprises from about 0.005% to about 0.05% cyclosporin A, polypropylene oxide, and peppermint oil.

Another embodiment comprises from about 0.005% to about 0.05% cyclosporin A, polypropylene oxide, and sunflower oil.

Another embodiment comprises from about 0.005% to about 0.05% cyclosporin A, polypropylene oxide, and eucalpytus oil.

Another embodiment comprises from about 0.005% to about 0.05% cyclosporin A, polypropylene oxide, and sesame oil.

Another embodiment comprises from about 0.005% to about 0.05% cyclosporin A, polypropylene oxide, and an oil having a specific gravity below 0.9.

Another embodiment comprises from about 0.005% to about 0.05% cyclosporin A, polypropylene oxide, and mineral oil.

Another embodiment comprises from about 0.005% to about 0.05% cyclosporin A, polypropylene oxide, and coriander oil.

Another embodiment comprises from about 0.005% to about 0.05% cyclosporin A, polypropylene oxide, and lavender oil.

Another embodiment comprises from about 0.005% to about 0.05% cyclosporin A, polypropylene oxide, and citronella oil.

Another embodiment comprises from about 0.005% to about 0.05% cyclosporin A, polypropylene oxide, and juniper oil.

Another embodiment comprises from about 0.005% to about 0.05% cyclosporin A, polypropylene oxide, and lemon oil.

Another embodiment comprises from about 0.005% to about 0.05% cyclosporin A, polypropylene oxide, and orange oil.

Another embodiment comprises from about 0.005% to about 0.05% cyclosporin A, polypropylene oxide, and clary sage oil.

Another embodiment comprises from about 0.005% to about 0.05% cyclosporin A, polypropylene oxide, and nutmeg oil.

Another embodiment comprises from about 0.005% to about 0.05% cyclosporin A, polypropylene oxide, and tea tree oil.

Another embodiment comprises from about 0.005% to about 0.05% cyclosporin A, a polyethylene oxide-polypropylene oxide copolymer, and an oil having a specific gravity between 0.90 and 0.95.

Another embodiment comprises from about 0.005% to about 0.05% cyclosporin A, a polyethylene oxide-polypropylene oxide copolymer, and almond oil.

Another embodiment comprises from about 0.005% to about 0.05% cyclosporin A, a polyethylene oxide-polypropylene oxide copolymer, and corn oil.

Another embodiment comprises from about 0.005% to about 0.05% cyclosporin A, a polyethylene oxide-polypropylene oxide copolymer, and arachis oil.

Another embodiment comprises from about 0.005% to about 0.05% cyclosporin A, a polyethylene oxide-polypropylene oxide copolymer, and cottonseed oil.

Another embodiment comprises from about 0.005% to about 0.05% cyclosporin A, a polyethylene oxide-polypropylene oxide copolymer, and safflower oil.

Another embodiment comprises from about 0.005% to about 0.05% cyclosporin A, a polyethylene oxide-polypropylene oxide copolymer, and maize oil.

Another embodiment comprises from about 0.005% to about 0.05% cyclosporin A, a polyethylene oxide-polypropylene oxide copolymer, and linseed oil.

Another embodiment comprises from about 0.005% to about 0.05% cyclosporin A, a polyethylene oxide-polypropylene oxide copolymer, and rapeseed oil.

Another embodiment comprises from about 0.005% to about 0.05% cyclosporin A, a polyethylene oxide-polypropylene oxide copolymer, and soybean oil.

Another embodiment comprises from about 0.005% to about 0.05% cyclosporin A, a polyethylene oxide-polypropylene oxide copolymer, and olive oil.

Another embodiment comprises from about 0.005% to about 0.05% cyclosporin A, a polyethylene oxide-polypropylene oxide copolymer, and caraway oil.

Another embodiment comprises from about 0.005% to about 0.05% cyclosporin A, a polyethylene oxide-polypropylene oxide copolymer, and rosemary oil.

Another embodiment comprises from about 0.005% to about 0.05% cyclosporin A, a polyethylene oxide-polypropylene oxide copolymer, and peanut oil.

Another embodiment comprises from about 0.005% to about 0.05% cyclosporin A, a polyethylene oxide-polypropylene oxide copolymer, and peppermint oil.

Another embodiment comprises from about 0.005% to about 0.05% cyclosporin A, a polyethylene oxide-polypropylene oxide copolymer, and sunflower oil.

Another embodiment comprises from about 0.005% to about 0.05% cyclosporin A, a polyethylene oxide-polypropylene oxide copolymer, and eucalpytus oil.

Another embodiment comprises from about 0.005% to about 0.05% cyclosporin A, a polyethylene oxide-polypropylene oxide copolymer, and sesame oil.

Another embodiment comprises from about 0.005% to about 0.05% cyclosporin A, a polyethylene oxide-polypropylene oxide copolymer, and an oil having a specific gravity below 0.9.

Another embodiment comprises from about 0.005% to about 0.05% cyclosporin A, a polyethylene oxide-polypropylene oxide copolymer, and mineral oil.

Another embodiment comprises from about 0.005% to about 0.05% cyclosporin A, a polyethylene oxide-polypropylene oxide copolymer, and coriander oil.

Another embodiment comprises from about 0.005% to about 0.05% cyclosporin A, a polyethylene oxide-polypropylene oxide copolymer, and lavender oil.

Another embodiment comprises from about 0.005% to about 0.05% cyclosporin A, a polyethylene oxide-polypropylene oxide copolymer, and citronella oil.

Another embodiment comprises from about 0.005% to about 0.05% cyclosporin A, a polyethylene oxide-polypropylene oxide copolymer, and juniper oil.

Another embodiment comprises from about 0.005% to about 0.05% cyclosporin A, a polyethylene oxide-polypropylene oxide copolymer, and lemon oil.

Another embodiment comprises from about 0.005% to about 0.05% cyclosporin A, a polyethylene oxide-polypropylene oxide copolymer, and orange oil.

Another embodiment comprises from about 0.005% to about 0.05% cyclosporin A, a polyethylene oxide-polypropylene oxide copolymer, and clary sage oil.

Another embodiment comprises from about 0.005% to about 0.05% cyclosporin A, a polyethylene oxide-polypropylene oxide copolymer, and nutmeg oil.

Another embodiment comprises from about 0.005% to about 0.05% cyclosporin A, a polyethylene oxide-polypropylene oxide copolymer, and tea tree oil.

Another embodiment comprises from about 0.005% to about 0.05% cyclosporin A, an alcohol ethoxylate, and an oil having a specific gravity between 0.90 and 0.95.

Another embodiment comprises from about 0.005% to about 0.05% cyclosporin A, an alcohol ethoxylate, and almond oil.

Another embodiment comprises from about 0.005% to about 0.05% cyclosporin A, an alcohol ethoxylate, and corn oil.

Another embodiment comprises from about 0.005% to about 0.05% cyclosporin A, an alcohol ethoxylate, and arachis oil.

Another embodiment comprises from about 0.005% to about 0.05% cyclosporin A, an alcohol ethoxylate, and cottonseed oil.

Another embodiment comprises from about 0.005% to about 0.05% cyclosporin A, an alcohol ethoxylate, and safflower oil.

Another embodiment comprises from about 0.005% to about 0.05% cyclosporin A, an alcohol ethoxylate, and maize oil.

Another embodiment comprises from about 0.005% to about 0.05% cyclosporin A, an alcohol ethoxylate, and linseed oil.

Another embodiment comprises from about 0.005% to about 0.05% cyclosporin A, an alcohol ethoxylate, and rapeseed oil.

Another embodiment comprises from about 0.005% to about 0.05% cyclosporin A, an alcohol ethoxylate, and soybean oil.

Another embodiment comprises from about 0.005% to about 0.05% cyclosporin A, an alcohol ethoxylate, and olive oil.

Another embodiment comprises from about 0.005% to about 0.05% cyclosporin A, an alcohol ethoxylate, and caraway oil.

Another embodiment comprises from about 0.005% to about 0.05% cyclosporin A, an alcohol ethoxylate, and rosemary oil.

Another embodiment comprises from about 0.005% to about 0.05% cyclosporin A, an alcohol ethoxylate, and peanut oil.

Another embodiment comprises from about 0.005% to about 0.05% cyclosporin A, an alcohol ethoxylate, and peppermint oil.

Another embodiment comprises from about 0.005% to about 0.05% cyclosporin A, an alcohol ethoxylate, and sunflower oil.

Another embodiment comprises from about 0.005% to about 0.05% cyclosporin A, an alcohol ethoxylate, and eucalpytus oil.

Another embodiment comprises from about 0.005% to about 0.05% cyclosporin A, an alcohol ethoxylate, and sesame oil.

Another embodiment comprises from about 0.005% to about 0.05% cyclosporin A, an alcohol ethoxylate, and an oil having a specific gravity below 0.9.

Another embodiment comprises from about 0.005% to about 0.05% cyclosporin A, an alcohol ethoxylate, and mineral oil.

Another embodiment comprises from about 0.005% to about 0.05% cyclosporin A, an alcohol ethoxylate, and coriander oil.

Another embodiment comprises from about 0.005% to about 0.05% cyclosporin A, an alcohol ethoxylate, and lavender oil.

Another embodiment comprises from about 0.005% to about 0.05% cyclosporin A, an alcohol ethoxylate, and citronella oil.

Another embodiment comprises from about 0.005% to about 0.05% cyclosporin A, an alcohol ethoxylate, and juniper oil.

Another embodiment comprises from about 0.005% to about 0.05% cyclosporin A, an alcohol ethoxylate, and lemon oil.

Another embodiment comprises from about 0.005% to about 0.05% cyclosporin A, an alcohol ethoxylate, and orange oil.

Another embodiment comprises from about 0.005% to about 0.05% cyclosporin A, an alcohol ethoxylate, and clary sage oil.

Another embodiment comprises from about 0.005% to about 0.05% cyclosporin A, an alcohol ethoxylate, and nutmeg oil.

Another embodiment comprises from about 0.005% to about 0.05% cyclosporin A, an alcohol ethoxylate, and tea tree oil.

Another embodiment comprises from about 0.005% to about 0.05% cyclosporin A, an alkylphenol ethoxylate, and an oil having a specific gravity between 0.90 and 0.95.

Another embodiment comprises from about 0.005% to about 0.05% cyclosporin A, an alkylphenol ethoxylate, and almond oil.

Another embodiment comprises from about 0.005% to about 0.05% cyclosporin A, an alkylphenol ethoxylate, and corn oil.

Another embodiment comprises from about 0.005% to about 0.05% cyclosporin A, an alkylphenol ethoxylate, and arachis oil.

Another embodiment comprises from about 0.005% to about 0.05% cyclosporin A, an alkylphenol ethoxylate, and cottonseed oil.

Another embodiment comprises from about 0.005% to about 0.05% cyclosporin A, an alkylphenol ethoxylate, and safflower oil.

Another embodiment comprises from about 0.005% to about 0.05% cyclosporin A, an alkylphenol ethoxylate, and maize oil.

Another embodiment comprises from about 0.005% to about 0.05% cyclosporin A, an alkylphenol ethoxylate, and linseed oil.

Another embodiment comprises from about 0.005% to about 0.05% cyclosporin A, an alkylphenol ethoxylate, and rapeseed oil.

Another embodiment comprises from about 0.005% to about 0.05% cyclosporin A, an alkylphenol ethoxylate, and soybean oil.

Another embodiment comprises from about 0.005% to about 0.05% cyclosporin A, an alkylphenol ethoxylate, and olive oil.

Another embodiment comprises from about 0.005% to about 0.05% cyclosporin A, an alkylphenol ethoxylate, and caraway oil.

Another embodiment comprises from about 0.005% to about 0.05% cyclosporin A, an alkylphenol ethoxylate, and rosemary oil.

Another embodiment comprises from about 0.005% to about 0.05% cyclosporin A, an alkylphenol ethoxylate, and peanut oil.

Another embodiment comprises from about 0.005% to about 0.05% cyclosporin A, an alkylphenol ethoxylate, and peppermint oil.

Another embodiment comprises from about 0.005% to about 0.05% cyclosporin A, an alkylphenol ethoxylate, and sunflower oil.

Another embodiment comprises from about 0.005% to about 0.05% cyclosporin A, an alkylphenol ethoxylate, and eucalpytus oil.

Another embodiment comprises from about 0.005% to about 0.05% cyclosporin A, an alkylphenol ethoxylate, and sesame oil.

Another embodiment comprises from about 0.005% to about 0.05% cyclosporin A, an alkylphenol ethoxylate, and an oil having a specific gravity below 0.9.

Another embodiment comprises from about 0.005% to about 0.05% cyclosporin A, an alkylphenol ethoxylate, and mineral oil.

Another embodiment comprises from about 0.005% to about 0.05% cyclosporin A, an alkylphenol ethoxylate, and coriander oil.

Another embodiment comprises from about 0.005% to about 0.05% cyclosporin A, an alkylphenol ethoxylate, and lavender oil.

Another embodiment comprises from about 0.005% to about 0.05% cyclosporin A, an alkylphenol ethoxylate, and citronella oil.

Another embodiment comprises from about 0.005% to about 0.05% cyclosporin A, an alkylphenol ethoxylate, and juniper oil.

Another embodiment comprises from about 0.005% to about 0.05% cyclosporin A, an alkylphenol ethoxylate, and lemon oil.

Another embodiment comprises from about 0.005% to about 0.05% cyclosporin A, an alkylphenol ethoxylate, and orange oil.

Another embodiment comprises from about 0.005% to about 0.05% cyclosporin A, an alkylphenol ethoxylate, and clary sage oil.

Another embodiment comprises from about 0.005% to about 0.05% cyclosporin A, an alkylphenol ethoxylate, and nutmeg oil.

Another embodiment comprises from about 0.005% to about 0.05% cyclosporin A, an alkylphenol ethoxylate, and tea tree oil.

Another embodiment comprises from about 0.005% to about 0.05% cyclosporin A, an alkyl glycoside, and an oil having a specific gravity between 0.90 and 0.95.

Another embodiment comprises from about 0.005% to about 0.05% cyclosporin A, an alkyl glycoside, and almond oil.

Another embodiment comprises from about 0.005% to about 0.05% cyclosporin A, an alkyl glycoside, and corn oil.

Another embodiment comprises from about 0.005% to about 0.05% cyclosporin A, an alkyl glycoside, and arachis oil.

Another embodiment comprises from about 0.005% to about 0.05% cyclosporin A, an alkyl glycoside, and cottonseed oil.

Another embodiment comprises from about 0.005% to about 0.05% cyclosporin A, an alkyl glycoside, and safflower oil.

Another embodiment comprises from about 0.005% to about 0.05% cyclosporin A, an alkyl glycoside, and maize oil.

Another embodiment comprises from about 0.005% to about 0.05% cyclosporin A, an alkyl glycoside, and linseed oil.

Another embodiment comprises from about 0.005% to about 0.05% cyclosporin A, an alkyl glycoside, and rapeseed oil.

Another embodiment comprises from about 0.005% to about 0.05% cyclosporin A, an alkyl glycoside, and soybean oil.

Another embodiment comprises from about 0.005% to about 0.05% cyclosporin A, an alkyl glycoside, and olive oil.

Another embodiment comprises from about 0.005% to about 0.05% cyclosporin A, an alkyl glycoside, and caraway oil.

Another embodiment comprises from about 0.005% to about 0.05% cyclosporin A, an alkyl glycoside, and rosemary oil.

Another embodiment comprises from about 0.005% to about 0.05% cyclosporin A, an alkyl glycoside, and peanut oil.

Another embodiment comprises from about 0.005% to about 0.05% cyclosporin A, an alkyl glycoside, and peppermint oil.

Another embodiment comprises from about 0.005% to about 0.05% cyclosporin A, an alkyl glycoside, and sunflower oil.

Another embodiment comprises from about 0.005% to about 0.05% cyclosporin A, an alkyl glycoside, and eucalpytus oil.

Another embodiment comprises from about 0.005% to about 0.05% cyclosporin A, an alkyl glycoside, and sesame oil.

Another embodiment comprises from about 0.005% to about 0.05% cyclosporin A, an alkyl glycoside, and an oil having a specific gravity below 0.9.

Another embodiment comprises from about 0.005% to about 0.05% cyclosporin A, an alkyl glycoside, and mineral oil.

Another embodiment comprises from about 0.005% to about 0.05% cyclosporin A, an alkyl glycoside, and coriander oil.

Another embodiment comprises from about 0.005% to about 0.05% cyclosporin A, an alkyl glycoside, and lavender oil.

Another embodiment comprises from about 0.005% to about 0.05% cyclosporin A, an alkyl glycoside, and citronella oil.

Another embodiment comprises from about 0.005% to about 0.05% cyclosporin A, an alkyl glycoside, and juniper oil.

Another embodiment comprises from about 0.005% to about 0.05% cyclosporin A, an alkyl glycoside, and lemon oil.

Another embodiment comprises from about 0.005% to about 0.05% cyclosporin A, an alkyl glycoside, and orange oil.

Another embodiment comprises from about 0.005% to about 0.05% cyclosporin A, an alkyl glycoside, and clary sage oil.

Another embodiment comprises from about 0.005% to about 0.05% cyclosporin A, an alkyl glycoside, and nutmeg oil.

Another embodiment comprises from about 0.005% to about 0.05% cyclosporin A, an alkyl glycoside, and tea tree oil.

Another embodiment comprises from about 0.005% to about 0.05% cyclosporin A, alkyl polyglycoside, and an oil having a specific gravity between 0.90 and 0.95.

Another embodiment comprises from about 0.005% to about 0.05% cyclosporin A, alkyl polyglycoside, and almond oil.

Another embodiment comprises from about 0.005% to about 0.05% cyclosporin A, alkyl polyglycoside, and corn oil.

Another embodiment comprises from about 0.005% to about 0.05% cyclosporin A, alkyl polyglycoside, and arachis oil.

Another embodiment comprises from about 0.005% to about 0.05% cyclosporin A, alkyl polyglycoside, and cottonseed oil.

Another embodiment comprises from about 0.005% to about 0.05% cyclosporin A, alkyl polyglycoside, and safflower oil.

Another embodiment comprises from about 0.005% to about 0.05% cyclosporin A, alkyl polyglycoside, and maize oil.

Another embodiment comprises from about 0.005% to about 0.05% cyclosporin A, alkyl polyglycoside, and linseed oil.

Another embodiment comprises from about 0.005% to about 0.05% cyclosporin A, alkyl polyglycoside, and rapeseed oil.

Another embodiment comprises from about 0.005% to about 0.05% cyclosporin A, alkyl polyglycoside, and soybean oil.

Another embodiment comprises from about 0.005% to about 0.05% cyclosporin A, alkyl polyglycoside, and olive oil.

Another embodiment comprises from about 0.005% to about 0.05% cyclosporin A, alkyl polyglycoside, and caraway oil.

Another embodiment comprises from about 0.005% to about 0.05% cyclosporin A, alkyl polyglycoside, and rosemary oil.

Another embodiment comprises from about 0.005% to about 0.05% cyclosporin A, alkyl polyglycoside, and peanut oil.

Another embodiment comprises from about 0.005% to about 0.05% cyclosporin A, alkyl polyglycoside, and peppermint oil.

Another embodiment comprises from about 0.005% to about 0.05% cyclosporin A, alkyl polyglycoside, and sunflower oil.

Another embodiment comprises from about 0.005% to about 0.05% cyclosporin A, alkyl polyglycoside, and eucalpytus oil.

Another embodiment comprises from about 0.005% to about 0.05% cyclosporin A, alkyl polyglycoside, and sesame oil.

Another embodiment comprises from about 0.005% to about 0.05% cyclosporin A, alkyl polyglycoside, and an oil having a specific gravity below 0.9.

Another embodiment comprises from about 0.005% to about 0.05% cyclosporin A, alkyl polyglycoside, and mineral oil.

Another embodiment comprises from about 0.005% to about 0.05% cyclosporin A, alkyl polyglycoside, and coriander oil.

Another embodiment comprises from about 0.005% to about 0.05% cyclosporin A, alkyl polyglycoside, and lavender oil.

Another embodiment comprises from about 0.005% to about 0.05% cyclosporin A, alkyl polyglycoside, and citronella oil.

Another embodiment comprises from about 0.005% to about 0.05% cyclosporin A, alkyl polyglycoside, and juniper oil.

Another embodiment comprises from about 0.005% to about 0.05% cyclosporin A, alkyl polyglycoside, and lemon oil.

Another embodiment comprises from about 0.005% to about 0.05% cyclosporin A, alkyl polyglycoside, and orange oil.

Another embodiment comprises from about 0.005% to about 0.05% cyclosporin A, alkyl polyglycoside, and clary sage oil.

Another embodiment comprises from about 0.005% to about 0.05% cyclosporin A, alkyl polyglycoside, and nutmeg oil.

Another embodiment comprises from about 0.005% to about 0.05% cyclosporin A, alkyl polyglycoside, and tea tree oil.

Another embodiment comprises from about 0.005% to about 0.05% cyclosporin A, a fatty alcohol, and an oil having a specific gravity between 0.90 and 0.95.

Another embodiment comprises from about 0.005% to about 0.05% cyclosporin A, a fatty alcohol, and almond oil.

Another embodiment comprises from about 0.005% to about 0.05% cyclosporin A, a fatty alcohol, and corn oil.

Another embodiment comprises from about 0.005% to about 0.05% cyclosporin A, a fatty alcohol, and arachis oil.

Another embodiment comprises from about 0.005% to about 0.05% cyclosporin A, a fatty alcohol, and cottonseed oil.

Another embodiment comprises from about 0.005% to about 0.05% cyclosporin A, a fatty alcohol, and safflower oil.

Another embodiment comprises from about 0.005% to about 0.05% cyclosporin A, a fatty alcohol, and maize oil.

Another embodiment comprises from about 0.005% to about 0.05% cyclosporin A, a fatty alcohol, and linseed oil.

Another embodiment comprises from about 0.005% to about 0.05% cyclosporin A, a fatty alcohol, and rapeseed oil.

Another embodiment comprises from about 0.005% to about 0.05% cyclosporin A, a fatty alcohol, and soybean oil.

Another embodiment comprises from about 0.005% to about 0.05% cyclosporin A, a fatty alcohol, and olive oil.

Another embodiment comprises from about 0.005% to about 0.05% cyclosporin A, a fatty alcohol, and caraway oil.

Another embodiment comprises from about 0.005% to about 0.05% cyclosporin A, a fatty alcohol, and rosemary oil.

Another embodiment comprises from about 0.005% to about 0.05% cyclosporin A, a fatty alcohol, and peanut oil.

Another embodiment comprises from about 0.005% to about 0.05% cyclosporin A, a fatty alcohol, and peppermint oil.

Another embodiment comprises from about 0.005% to about 0.05% cyclosporin A, a fatty alcohol, and sunflower oil.

Another embodiment comprises from about 0.005% to about 0.05% cyclosporin A, a fatty alcohol, and eucalyptus oil.

Another embodiment comprises from about 0.005% to about 0.05% cyclosporin A, a fatty alcohol, and sesame oil.

Another embodiment comprises from about 0.005% to about 0.05% cyclosporin A, a fatty alcohol, and an oil having a specific gravity below 0.9.

Another embodiment comprises from about 0.005% to about 0.05% cyclosporin A, a fatty alcohol, and mineral oil.

Another embodiment comprises from about 0.005% to about 0.05% cyclosporin A, a fatty alcohol, and coriander oil.

Another embodiment comprises from about 0.005% to about 0.05% cyclosporin A, a fatty alcohol, and lavender oil.

Another embodiment comprises from about 0.005% to about 0.05% cyclosporin A, a fatty alcohol, and citronella oil.

Another embodiment comprises from about 0.005% to about 0.05% cyclosporin A, a fatty alcohol, and juniper oil.

Another embodiment comprises from about 0.005% to about 0.05% cyclosporin A, a fatty alcohol, and lemon oil.

Another embodiment comprises from about 0.005% to about 0.05% cyclosporin A, a fatty alcohol, and orange oil.

Another embodiment comprises from about 0.005% to about 0.05% cyclosporin A, a fatty alcohol, and clary sage oil.

Another embodiment comprises from about 0.005% to about 0.05% cyclosporin A, a fatty alcohol, and nutmeg oil.

Another embodiment comprises from about 0.005% to about 0.05% cyclosporin A, a fatty alcohol, and tea tree oil.

Another embodiment comprises from about 0.005% to about 0.05% cyclosporin A, hydroxypropylmethyl cellulose, and an oil having a specific gravity between 0.90 and 0.95.

Another embodiment comprises from about 0.005% to about 0.05% cyclosporin A, hydroxypropylmethyl cellulose, and almond oil.

Another embodiment comprises from about 0.005% to about 0.05% cyclosporin A, hydroxypropylmethyl cellulose, and corn oil.

Another embodiment comprises from about 0.005% to about 0.05% cyclosporin A, hydroxypropylmethyl cellulose, and arachis oil.

Another embodiment comprises from about 0.005% to about 0.05% cyclosporin A, hydroxypropylmethyl cellulose, and cottonseed oil.

Another embodiment comprises from about 0.005% to about 0.05% cyclosporin A, hydroxypropylmethyl cellulose, and safflower oil.

Another embodiment comprises from about 0.005% to about 0.05% cyclosporin A, hydroxypropylmethyl cellulose, and maize oil.

Another embodiment comprises from about 0.005% to about 0.05% cyclosporin A, hydroxypropylmethyl cellulose, and linseed oil.

Another embodiment comprises from about 0.005% to about 0.05% cyclosporin A, hydroxypropylmethyl cellulose, and rapeseed oil.

Another embodiment comprises from about 0.005% to about 0.05% cyclosporin A, hydroxypropylmethyl cellulose, and soybean oil.

Another embodiment comprises from about 0.005% to about 0.05% cyclosporin A, hydroxypropylmethyl cellulose, and olive oil.

Another embodiment comprises from about 0.005% to about 0.05% cyclosporin A, hydroxypropylmethyl cellulose, and caraway oil.

Another embodiment comprises from about 0.005% to about 0.05% cyclosporin A, hydroxypropylmethyl cellulose, and rosemary oil.

Another embodiment comprises from about 0.005% to about 0.05% cyclosporin A, hydroxypropylmethyl cellulose, and peanut oil.

Another embodiment comprises from about 0.005% to about 0.05% cyclosporin A, hydroxypropylmethyl cellulose, and peppermint oil.

Another embodiment comprises from about 0.005% to about 0.05% cyclosporin A, hydroxypropylmethyl cellulose, and sunflower oil.

Another embodiment comprises from about 0.005% to about 0.05% cyclosporin A, hydroxypropylmethyl cellulose, and eucalyptus oil.

Another embodiment comprises from about 0.005% to about 0.05% cyclosporin A, hydroxypropylmethyl cellulose, and sesame oil.

Another embodiment comprises from about 0.005% to about 0.05% cyclosporin A, hydroxypropylmethyl cellulose, and an oil having a specific gravity below 0.9.

Another embodiment comprises from about 0.005% to about 0.05% cyclosporin A, hydroxypropylmethyl cellulose, and mineral oil.

Another embodiment comprises from about 0.005% to about 0.05% cyclosporin A, hydroxypropylmethyl cellulose, and coriander oil.

Another embodiment comprises from about 0.005% to about 0.05% cyclosporin A, hydroxypropylmethyl cellulose, and lavender oil.

Another embodiment comprises from about 0.005% to about 0.05% cyclosporin A, hydroxypropylmethyl cellulose, and citronella oil.

Another embodiment comprises from about 0.005% to about 0.05% cyclosporin A, hydroxypropylmethyl cellulose, and juniper oil.

Another embodiment comprises from about 0.005% to about 0.05% cyclosporin A, hydroxypropylmethyl cellulose, and lemon oil.

Another embodiment comprises from about 0.005% to about 0.05% cyclosporin A, hydroxypropylmethyl cellulose, and orange oil.

Another embodiment comprises from about 0.005% to about 0.05% cyclosporin A, hydroxypropylmethyl cellulose, and clary sage oil.

Another embodiment comprises from about 0.005% to about 0.05% cyclosporin A, hydroxypropylmethyl cellulose, and nutmeg oil.

Another embodiment comprises from about 0.005% to about 0.05% cyclosporin A, hydroxypropylmethyl cellulose, and tea tree oil.

Another embodiment comprises from about 0.005% to about 0.05% cyclosporin A, carboxymethyl cellulose, and an oil having a specific gravity between 0.90 and 0.95.

Another embodiment comprises from about 0.005% to about 0.05% cyclosporin A, carboxymethyl cellulose, and almond oil.

Another embodiment comprises from about 0.005% to about 0.05% cyclosporin A, carboxymethyl cellulose, and corn oil.

Another embodiment comprises from about 0.005% to about 0.05% cyclosporin A, carboxymethyl cellulose, and arachis oil.

Another embodiment comprises from about 0.005% to about 0.05% cyclosporin A, carboxymethyl cellulose, and cottonseed oil.

Another embodiment comprises from about 0.005% to about 0.05% cyclosporin A, carboxymethyl cellulose, and safflower oil.

Another embodiment comprises from about 0.005% to about 0.05% cyclosporin A, carboxymethyl cellulose, and maize oil.

Another embodiment comprises from about 0.005% to about 0.05% cyclosporin A, carboxymethyl cellulose, and linseed oil.

Another embodiment comprises from about 0.005% to about 0.05% cyclosporin A, carboxymethyl cellulose, and rapeseed oil.

Another embodiment comprises from about 0.005% to about 0.05% cyclosporin A, carboxymethyl cellulose, and soybean oil.

Another embodiment comprises from about 0.005% to about 0.05% cyclosporin A, carboxymethyl cellulose, and olive oil.

Another embodiment comprises from about 0.005% to about 0.05% cyclosporin A, carboxymethyl cellulose, and caraway oil.

Another embodiment comprises from about 0.005% to about 0.05% cyclosporin A, carboxymethyl cellulose, and rosemary oil.

Another embodiment comprises from about 0.005% to about 0.05% cyclosporin A, carboxymethyl cellulose, and peanut oil.

Another embodiment comprises from about 0.005% to about 0.05% cyclosporin A, carboxymethyl cellulose, and peppermint oil.

Another embodiment comprises from about 0.005% to about 0.05% cyclosporin A, carboxymethyl cellulose, and sunflower oil.

Another embodiment comprises from about 0.005% to about 0.05% cyclosporin A, carboxymethyl cellulose, and eucalpytus oil.

Another embodiment comprises from about 0.005% to about 0.05% cyclosporin A, carboxymethyl cellulose, and sesame oil.

Another embodiment comprises from about 0.005% to about 0.05% cyclosporin A, carboxymethyl cellulose, and an oil having a specific gravity below 0.9.

Another embodiment comprises from about 0.005% to about 0.05% cyclosporin A, carboxymethyl cellulose, and mineral oil.

Another embodiment comprises from about 0.005% to about 0.05% cyclosporin A, carboxymethyl cellulose, and coriander oil.

Another embodiment comprises from about 0.005% to about 0.05% cyclosporin A, carboxymethyl cellulose, and lavender oil.

Another embodiment comprises from about 0.005% to about 0.05% cyclosporin A, carboxymethyl cellulose, and citronella oil.

Another embodiment comprises from about 0.005% to about 0.05% cyclosporin A, carboxymethyl cellulose, and juniper oil.

Another embodiment comprises from about 0.005% to about 0.05% cyclosporin A, carboxymethyl cellulose, and lemon oil.

Another embodiment comprises from about 0.005% to about 0.05% cyclosporin A, carboxymethyl cellulose, and orange oil.

Another embodiment comprises from about 0.005% to about 0.05% cyclosporin A, carboxymethyl cellulose, and clary sage oil.

Another embodiment comprises from about 0.005% to about 0.05% cyclosporin A, carboxymethyl cellulose, and nutmeg oil.

Another embodiment comprises from about 0.005% to about 0.05% cyclosporin A, carboxymethyl cellulose, and tea tree oil.

Another embodiment comprises from about 0.005% to about 0.05% cyclosporin A, a polyacrylic acid, and an oil having a specific gravity between 0.90 and 0.95.

Another embodiment comprises from about 0.005% to about 0.05% cyclosporin A, a polyacrylic acid, and almond oil.

Another embodiment comprises from about 0.005% to about 0.05% cyclosporin A, a polyacrylic acid, and corn oil.

Another embodiment comprises from about 0.005% to about 0.05% cyclosporin A, a polyacrylic acid, and arachis oil.

Another embodiment comprises from about 0.005% to about 0.05% cyclosporin A, a polyacrylic acid, and cottonseed oil.

Another embodiment comprises from about 0.005% to about 0.05% cyclosporin A, a polyacrylic acid, and safflower oil.

Another embodiment comprises from about 0.005% to about 0.05% cyclosporin A, a polyacrylic acid, and maize oil.

Another embodiment comprises from about 0.005% to about 0.05% cyclosporin A, a polyacrylic acid, and linseed oil.

Another embodiment comprises from about 0.005% to about 0.05% cyclosporin A, a polyacrylic acid, and rapeseed oil.

Another embodiment comprises from about 0.005% to about 0.05% cyclosporin A, a polyacrylic acid, and soybean oil.

Another embodiment comprises from about 0.005% to about 0.05% cyclosporin A, a polyacrylic acid, and olive oil.

Another embodiment comprises from about 0.005% to about 0.05% cyclosporin A, a polyacrylic acid, and caraway oil.

Another embodiment comprises from about 0.005% to about 0.05% cyclosporin A, a polyacrylic acid, and rosemary oil.

Another embodiment comprises from about 0.005% to about 0.05% cyclosporin A, a polyacrylic acid, and peanut oil.

Another embodiment comprises from about 0.005% to about 0.05% cyclosporin A, a polyacrylic acid, and peppermint oil.

Another embodiment comprises from about 0.005% to about 0.05% cyclosporin A, a polyacrylic acid, and sunflower oil.

Another embodiment comprises from about 0.005% to about 0.05% cyclosporin A, a polyacrylic acid, and eucalpytus oil.

Another embodiment comprises from about 0.005% to about 0.05% cyclosporin A, a polyacrylic acid, and sesame oil.

Another embodiment comprises from about 0.005% to about 0.05% cyclosporin A, a polyacrylic acid, and an oil having a specific gravity below 0.9.

Another embodiment comprises from about 0.005% to about 0.05% cyclosporin A, a polyacrylic acid, and mineral oil.

Another embodiment comprises from about 0.005% to about 0.05% cyclosporin A, a polyacrylic acid, and coriander oil.

Another embodiment comprises from about 0.005% to about 0.05% cyclosporin A, a polyacrylic acid, and lavender oil.

Another embodiment comprises from about 0.005% to about 0.05% cyclosporin A, a polyacrylic acid, and citronella oil.

Another embodiment comprises from about 0.005% to about 0.05% cyclosporin A, a polyacrylic acid, and juniper oil.

Another embodiment comprises from about 0.005% to about 0.05% cyclosporin A, a polyacrylic acid, and lemon oil.

Another embodiment comprises from about 0.005% to about 0.05% cyclosporin A, a polyacrylic acid, and orange oil.

Another embodiment comprises from about 0.005% to about 0.05% cyclosporin A, a polyacrylic acid, and clary sage oil.

Another embodiment comprises from about 0.005% to about 0.05% cyclosporin A, a polyacrylic acid, and nutmeg oil.

Another embodiment comprises from about 0.005% to about 0.05% cyclosporin A, a polyacrylic acid, and tea tree oil.

Another embodiment comprises from about 0.005% to about 0.05% cyclosporin A, a Carbomer, and an oil having a specific gravity between 0.90 and 0.95.

Another embodiment comprises from about 0.005% to about 0.05% cyclosporin A, a Carbomer, and almond oil.

Another embodiment comprises from about 0.005% to about 0.05% cyclosporin A, a Carbomer, and corn oil.

Another embodiment comprises from about 0.005% to about 0.05% cyclosporin A, a Carbomer, and arachis oil.

Another embodiment comprises from about 0.005% to about 0.05% cyclosporin A, a Carbomer, and cottonseed oil.

Another embodiment comprises from about 0.005% to about 0.05% cyclosporin A, a Carbomer, and safflower oil.

Another embodiment comprises from about 0.005% to about 0.05% cyclosporin A, a Carbomer, and maize oil.

Another embodiment comprises from about 0.005% to about 0.05% cyclosporin A, a Carbomer, and linseed oil.

Another embodiment comprises from about 0.005% to about 0.05% cyclosporin A, a Carbomer, and rapeseed oil.

Another embodiment comprises from about 0.005% to about 0.05% cyclosporin A, a Carbomer, and soybean oil.

Another embodiment comprises from about 0.005% to about 0.05% cyclosporin A, a Carbomer, and olive oil.

Another embodiment comprises from about 0.005% to about 0.05% cyclosporin A, a Carbomer, and caraway oil.

Another embodiment comprises from about 0.005% to about 0.05% cyclosporin A, a Carbomer, and rosemary oil.

Another embodiment comprises from about 0.005% to about 0.05% cyclosporin A, a Carbomer, and peanut oil.

Another embodiment comprises from about 0.005% to about 0.05% cyclosporin A, a Carbomer, and peppermint oil.

Another embodiment comprises from about 0.005% to about 0.05% cyclosporin A, a Carbomer, and sunflower oil.

Another embodiment comprises from about 0.005% to about 0.05% cyclosporin A, a Carbomer, and eucalpytus oil.

Another embodiment comprises from about 0.005% to about 0.05% cyclosporin A, a Carbomer, and sesame oil.

Another embodiment comprises from about 0.005% to about 0.05% cyclosporin A, a Carbomer, and an oil having a specific gravity below 0.9.

Another embodiment comprises from about 0.005% to about 0.05% cyclosporin A, a Carbomer, and mineral oil.

Another embodiment comprises from about 0.005% to about 0.05% cyclosporin A, a Carbomer, and coriander oil.

Another embodiment comprises from about 0.005% to about 0.05% cyclosporin A, a Carbomer, and lavender oil.

Another embodiment comprises from about 0.005% to about 0.05% cyclosporin A, a Carbomer, and citronella oil.

Another embodiment comprises from about 0.005% to about 0.05% cyclosporin A, a Carbomer, and juniper oil.

Another embodiment comprises from about 0.005% to about 0.05% cyclosporin A, a Carbomer, and lemon oil.

Another embodiment comprises from about 0.005% to about 0.05% cyclosporin A, a Carbomer, and orange oil.

Another embodiment comprises from about 0.005% to about 0.05% cyclosporin A, a Carbomer, and clary sage oil.

Another embodiment comprises from about 0.005% to about 0.05% cyclosporin A, a Carbomer, and nutmeg oil.

Another embodiment comprises from about 0.005% to about 0.05% cyclosporin A, a Carbomer, and tea tree oil.

Another embodiment comprises from about 0.005% to about 0.05% cyclosporin A, a phosphalipid, and an oil having a specific gravity between 0.90 and 0.95.

Another embodiment comprises from about 0.005% to about 0.05% cyclosporin A, a phosphalipid, and almond oil.

Another embodiment comprises from about 0.005% to about 0.05% cyclosporin A, a phosphalipid, and corn oil.

Another embodiment comprises from about 0.005% to about 0.05% cyclosporin A, a phosphalipid, and arachis oil.

Another embodiment comprises from about 0.005% to about 0.05% cyclosporin A, a phosphalipid, and cottonseed oil.

Another embodiment comprises from about 0.005% to about 0.05% cyclosporin A, a phosphalipid, and safflower oil.

Another embodiment comprises from about 0.005% to about 0.05% cyclosporin A, a phosphalipid, and maize oil.

Another embodiment comprises from about 0.005% to about 0.05% cyclosporin A, a phosphalipid, and linseed oil.

Another embodiment comprises from about 0.005% to about 0.05% cyclosporin A, a phosphalipid, and rapeseed oil.

Another embodiment comprises from about 0.005% to about 0.05% cyclosporin A, a phosphalipid, and soybean oil.

Another embodiment comprises from about 0.005% to about 0.05% cyclosporin A, a phosphalipid, and olive oil.

Another embodiment comprises from about 0.005% to about 0.05% cyclosporin A, a phosphalipid, and caraway oil.

Another embodiment comprises from about 0.005% to about 0.05% cyclosporin A, a phosphalipid, and rosemary oil.

Another embodiment comprises from about 0.005% to about 0.05% cyclosporin A, a phosphalipid, and peanut oil.

Another embodiment comprises from about 0.005% to about 0.05% cyclosporin A, a phosphalipid, and peppermint oil.

Another embodiment comprises from about 0.005% to about 0.05% cyclosporin A, a phosphalipid, and sunflower oil.

Another embodiment comprises from about 0.005% to about 0.05% cyclosporin A, a phosphalipid, and eucalpytus oil.

Another embodiment comprises from about 0.005% to about 0.05% cyclosporin A, a phosphalipid, and sesame oil.

Another embodiment comprises from about 0.005% to about 0.05% cyclosporin A, a phosphalipid, and an oil having a specific gravity below 0.9.

Another embodiment comprises from about 0.005% to about 0.05% cyclosporin A, a phosphalipid, and mineral oil.

Another embodiment comprises from about 0.005% to about 0.05% cyclosporin A, a phosphalipid, and coriander oil.

Another embodiment comprises from about 0.005% to about 0.05% cyclosporin A, a phosphalipid, and lavender oil.

Another embodiment comprises from about 0.005% to about 0.05% cyclosporin A, a phosphalipid, and citronella oil.

Another embodiment comprises from about 0.005% to about 0.05% cyclosporin A, a phospalipid, and juniper oil.

Another embodiment comprises from about 0.005% to about 0.05% cyclosporin A, a phospalipid, and lemon oil.

Another embodiment comprises from about 0.005% to about 0.05% cyclosporin A, a phospalipid, and orange oil.

Another embodiment comprises from about 0.005% to about 0.05% cyclosporin A, a phospalipid, and clary sage oil.

Another embodiment comprises from about 0.005% to about 0.05% cyclosporin A, a phospalipid, and nutmeg oil.

Another embodiment comprises from about 0.005% to about 0.05% cyclosporin A, a phospalipid, and tea tree oil.

Another embodiment comprises from about 0.005% to about 0.05% cyclosporin A, phosphatidyl chlorine, and an oil having a specific gravity between 0.90 and 0.95.

Another embodiment comprises from about 0.005% to about 0.05% cyclosporin A, phosphatidyl chloline, and almond oil.

Another embodiment comprises from about 0.005% to about 0.05% cyclosporin A, phosphatidyl chlorine, and corn oil.

Another embodiment comprises from about 0.005% to about 0.05% cyclosporin A, phosphatidyl chlorine, and arachis oil.

Another embodiment comprises from about 0.005% to about 0.05% cyclosporin A, phosphatidyl chloline, and cottonseed oil.

Another embodiment comprises from about 0.005% to about 0.05% cyclosporin A, phosphatidyl chlorine, and safflower oil.

Another embodiment comprises from about 0.005% to about 0.05% cyclosporin A, phosphatidyl chlorine, and maize oil.

Another embodiment comprises from about 0.005% to about 0.05% cyclosporin A, phosphatidyl chlorine, and linseed oil.

Another embodiment comprises from about 0.005% to about 0.05% cyclosporin A, phosphatidyl chloline, and rapeseed oil.

Another embodiment comprises from about 0.005% to about 0.05% cyclosporin A, phosphatidyl chloline, and soybean oil.

Another embodiment comprises from about 0.005% to about 0.05% cyclosporin A, phosphatidyl chlorine, and olive oil.

Another embodiment comprises from about 0.005% to about 0.05% cyclosporin A, phosphatidyl chloline, and caraway oil.

Another embodiment comprises from about 0.005% to about 0.05% cyclosporin A, phosphatidyl chlorine, and rosemary oil.

Another embodiment comprises from about 0.005% to about 0.05% cyclosporin A, phosphatidyl chloline, and peanut oil.

Another embodiment comprises from about 0.005% to about 0.05% cyclosporin A, phosphatidyl chlorine, and peppermint oil.

Another embodiment comprises from about 0.005% to about 0.05% cyclosporin A, phosphatidyl chloline, and sunflower oil.

Another embodiment comprises from about 0.005% to about 0.05% cyclosporin A, phosphatidyl chloline, and eucalpytus oil.

Another embodiment comprises from about 0.005% to about 0.05% cyclosporin A, phosphatidyl chlorine, and sesame oil.

Another embodiment comprises from about 0.005% to about 0.05% cyclosporin A, phosphatidyl chlorine, and an oil having a specific gravity below 0.9.

Another embodiment comprises from about 0.005% to about 0.05% cyclosporin A, phosphatidyl chlorine, and mineral oil.

Another embodiment comprises from about 0.005% to about 0.05% cyclosporin A, phosphatidyl chlorine, and coriander oil.

Another embodiment comprises from about 0.005% to about 0.05% cyclosporin A, phosphatidyl chlorine, and lavender oil.

Another embodiment comprises from about 0.005% to about 0.05% cyclosporin A, phosphatidyl chlorine, and citronella oil.

Another embodiment comprises from about 0.005% to about 0.05% cyclosporin A, phosphatidyl chloline, and juniper oil.

Another embodiment comprises from about 0.005% to about 0.05% cyclosporin A, phosphatidyl chloline, and lemon oil.

Another embodiment comprises from about 0.005% to about 0.05% cyclosporin A, phosphatidyl chloline, and orange oil.

Another embodiment comprises from about 0.005% to about 0.05% cyclosporin A, phosphatidyl chloline, and clary sage oil.

Another embodiment comprises from about 0.005% to about 0.05% cyclosporin A, phosphatidyl chloline, and nutmeg oil.

Another embodiment comprises from about 0.005% to about 0.05% cyclosporin A, phosphatidyl chloline, and tea tree oil.

Another embodiment comprises from about 0.005% to about 0.05% cyclosporin A, phosphatidyl serine, and an oil having a specific gravity between 0.90 and 0.95.

Another embodiment comprises from about 0.005% to about 0.05% cyclosporin A, phosphatidyl serine, and almond oil.

Another embodiment comprises from about 0.005% to about 0.05% cyclosporin A, phosphatidyl serine, and corn oil.

Another embodiment comprises from about 0.005% to about 0.05% cyclosporin A, phosphatidyl serine, and arachis oil.

Another embodiment comprises from about 0.005% to about 0.05% cyclosporin A, phosphatidyl serine, and cottonseed oil.

Another embodiment comprises from about 0.005% to about 0.05% cyclosporin A, phosphatidyl serine, and safflower oil.

Another embodiment comprises from about 0.005% to about 0.05% cyclosporin A, phosphatidyl serine, and maize oil.

Another embodiment comprises from about 0.005% to about 0.05% cyclosporin A, phosphatidyl serine, and linseed oil.

Another embodiment comprises from about 0.005% to about 0.05% cyclosporin A, phosphatidyl serine, and rapeseed oil.

Another embodiment comprises from about 0.005% to about 0.05% cyclosporin A, phosphatidyl serine, and soybean oil.

Another embodiment comprises from about 0.005% to about 0.05% cyclosporin A, phosphatidyl serine, and olive oil.

Another embodiment comprises from about 0.005% to about 0.05% cyclosporin A, phosphatidyl serine, and caraway oil.

Another embodiment comprises from about 0.005% to about 0.05% cyclosporin A, phosphatidyl serine, and rosemary oil.

Another embodiment comprises from about 0.005% to about 0.05% cyclosporin A, phosphatidyl serine, and peanut oil.

Another embodiment comprises from about 0.005% to about 0.05% cyclosporin A, phosphatidyl serine, and peppermint oil.

Another embodiment comprises from about 0.005% to about 0.05% cyclosporin A, phosphatidyl serine, and sunflower oil.

Another embodiment comprises from about 0.005% to about 0.05% cyclosporin A, phosphatidyl serine, and eucalpytus oil.

Another embodiment comprises from about 0.005% to about 0.05% cyclosporin A, phosphatidyl serine, and sesame oil.

Another embodiment comprises from about 0.005% to about 0.05% cyclosporin A, phosphatidyl serine, and an oil having a specific gravity below 0.9.

Another embodiment comprises from about 0.005% to about 0.05% cyclosporin A, phosphatidyl serine, and mineral oil.

Another embodiment comprises from about 0.005% to about 0.05% cyclosporin A, phosphatidyl serine, and coriander oil.

Another embodiment comprises from about 0.005% to about 0.05% cyclosporin A, phosphatidyl serine, and lavender oil.

Another embodiment comprises from about 0.005% to about 0.05% cyclosporin A, phosphatidyl serine, and citronella oil.

Another embodiment comprises from about 0.005% to about 0.05% cyclosporin A, phosphatidyl serine, and juniper oil.

Another embodiment comprises from about 0.005% to about 0.05% cyclosporin A, phosphatidyl serine, and lemon oil.

Another embodiment comprises from about 0.005% to about 0.05% cyclosporin A, phosphatidyl serine, and orange oil.

Another embodiment comprises from about 0.005% to about 0.05% cyclosporin A, phosphatidyl serine, and clary sage oil.

Another embodiment comprises from about 0.005% to about 0.05% cyclosporin A, phosphatidyl serine, and nutmeg oil.

Another embodiment comprises from about 0.005% to about 0.05% cyclosporin A, phosphatidyl serine, and tea tree oil.

Another embodiment comprises about 0.05% cyclosporin A, a sorbitan ester, and an oil having a specific gravity between 0.90 and 0.95.

Another embodiment comprises about 0.05% cyclosporin A, a sorbitan ester, and almond oil.

Another embodiment comprises about 0.05% cyclosporin A, a sorbitan ester, and corn oil.

Another embodiment comprises about 0.05% cyclosporin A, a sorbitan ester, and arachis oil.

Another embodiment comprises about 0.05% cyclosporin A, a sorbitan ester, and cottonseed oil.

Another embodiment comprises about 0.05% cyclosporin A, a sorbitan ester, and safflower oil.

Another embodiment comprises about 0.05% cyclosporin A, a sorbitan ester, and maize oil.

Another embodiment comprises about 0.05% cyclosporin A, a sorbitan ester, and linseed oil.

Another embodiment comprises about 0.05% cyclosporin A, a sorbitan ester, and rapeseed oil.

Another embodiment comprises about 0.05% cyclosporin A, a sorbitan ester, and soybean oil.

Another embodiment comprises about 0.05% cyclosporin A, a sorbitan ester, and olive oil.

Another embodiment comprises about 0.05% cyclosporin A, a sorbitan ester, and caraway oil.

Another embodiment comprises about 0.05% cyclosporin A, a sorbitan ester, and rosemary oil.

Another embodiment comprises about 0.05% cyclosporin A, a sorbitan ester, and peanut oil.

Another embodiment comprises about 0.05% cyclosporin A, a sorbitan ester, and peppermint oil.

Another embodiment comprises about 0.05% cyclosporin A, a sorbitan ester, and sunflower oil.

Another embodiment comprises about 0.05% cyclosporin A, a sorbitan ester, and eucalpytus oil.

Another embodiment comprises about 0.05% cyclosporin A, a sorbitan ester, and sesame oil.

Another embodiment comprises about 0.05% cyclosporin A, a sorbitan ester, and an oil having a specific gravity below 0.9.

Another embodiment comprises about 0.05% cyclosporin A, a sorbitan ester, and mineral oil.

Another embodiment comprises about 0.05% cyclosporin A, a sorbitan ester, and coriander oil.

Another embodiment comprises about 0.05% cyclosporin A, a sorbitan ester, and lavender oil.

Another embodiment comprises about 0.05% cyclosporin A, a sorbitan ester, and citronella oil.

Another embodiment comprises about 0.05% cyclosporin A, a sorbitan ester, and juniper oil.

Another embodiment comprises about 0.05% cyclosporin A, a sorbitan ester, and lemon oil.

Another embodiment comprises about 0.05% cyclosporin A, a sorbitan ester, and orange oil.

Another embodiment comprises about 0.05% cyclosporin A, a sorbitan ester, and clary sage oil.

Another embodiment comprises about 0.05% cyclosporin A, a sorbitan ester, and nutmeg oil.

Another embodiment comprises about 0.05% cyclosporin A, a sorbitan ester, and tea tree oil.

Another embodiment comprises about 0.05% cyclosporin A, Polysorbate 20, and an oil having a specific gravity between 0.90 and 0.95.

Another embodiment comprises about 0.05% cyclosporin A, Polysorbate 20, and almond oil.

Another embodiment comprises about 0.05% cyclosporin A, Polysorbate 20, and corn oil.

Another embodiment comprises about 0.05% cyclosporin A, Polysorbate 20, and arachis oil.
Another embodiment comprises about 0.05% cyclosporin A, Polysorbate 20, and cottonseed oil.
Another embodiment comprises about 0.05% cyclosporin A, Polysorbate 20, and safflower oil.
Another embodiment comprises about 0.05% cyclosporin A, Polysorbate 20, and maize oil.
Another embodiment comprises about 0.05% cyclosporin A, Polysorbate 20, and linseed oil.
Another embodiment comprises about 0.05% cyclosporin A, Polysorbate 20, and rapeseed oil.
Another embodiment comprises about 0.05% cyclosporin A, Polysorbate 20, and soybean oil.
Another embodiment comprises about 0.05% cyclosporin A, Polysorbate 20, and olive oil.
Another embodiment comprises about 0.05% cyclosporin A, Polysorbate 20, and caraway oil.
Another embodiment comprises about 0.05% cyclosporin A, Polysorbate 20, and rosemary oil.
Another embodiment comprises about 0.05% cyclosporin A, Polysorbate 20, and peanut oil.
Another embodiment comprises about 0.05% cyclosporin A, Polysorbate 20, and peppermint oil.
Another embodiment comprises about 0.05% cyclosporin A, Polysorbate 20, and sunflower oil.
Another embodiment comprises about 0.05% cyclosporin A, Polysorbate 20, and eucalpytus oil.
Another embodiment comprises about 0.05% cyclosporin A, Polysorbate 20, and sesame oil.
Another embodiment comprises about 0.05% cyclosporin A, Polysorbate 20, and an oil having a specific gravity below 0.9.
Another embodiment comprises about 0.05% cyclosporin A, Polysorbate 20, and mineral oil.
Another embodiment comprises about 0.05% cyclosporin A, Polysorbate 20, and coriander oil.
Another embodiment comprises about 0.05% cyclosporin A, Polysorbate 20, and lavender oil.
Another embodiment comprises about 0.05% cyclosporin A, Polysorbate 20, and citronella oil.
Another embodiment comprises about 0.05% cyclosporin A, Polysorbate 20, and juniper oil.
Another embodiment comprises about 0.05% cyclosporin A, Polysorbate 20, and lemon oil.
Another embodiment comprises about 0.05% cyclosporin A, Polysorbate 20, and orange oil.
Another embodiment comprises about 0.05% cyclosporin A, Polysorbate 20, and clary sage oil.
Another embodiment comprises about 0.05% cyclosporin A, Polysorbate 20, and nutmeg oil.
Another embodiment comprises about 0.05% cyclosporin A, Polysorbate 20, and tea tree oil.
Another embodiment comprises about 0.05% cyclosporin A, Polysorbate 40, and an oil having a specific gravity between 0.90 and 0.95.
Another embodiment comprises about 0.05% cyclosporin A, Polysorbate 40, and almond oil.
Another embodiment comprises about 0.05% cyclosporin A, Polysorbate 40, and corn oil.
Another embodiment comprises about 0.05% cyclosporin A, Polysorbate 40, and arachis oil.
Another embodiment comprises about 0.05% cyclosporin A, Polysorbate 40, and cottonseed oil.
Another embodiment comprises about 0.05% cyclosporin A, Polysorbate 40, and safflower oil.
Another embodiment comprises about 0.05% cyclosporin A, Polysorbate 40, and maize oil.
Another embodiment comprises about 0.05% cyclosporin A, Polysorbate 40, and linseed oil.
Another embodiment comprises about 0.05% cyclosporin A, Polysorbate 40, and rapeseed oil.
Another embodiment comprises about 0.05% cyclosporin A, Polysorbate 40, and soybean oil.
Another embodiment comprises about 0.05% cyclosporin A, Polysorbate 40, and olive oil.
Another embodiment comprises about 0.05% cyclosporin A, Polysorbate 40, and caraway oil.
Another embodiment comprises about 0.05% cyclosporin A, Polysorbate 40, and rosemary oil.
Another embodiment comprises about 0.05% cyclosporin A, Polysorbate 40, and peanut oil.
Another embodiment comprises about 0.05% cyclosporin A, Polysorbate 40, and peppermint oil.
Another embodiment comprises about 0.05% cyclosporin A, Polysorbate 40, and sunflower oil.
Another embodiment comprises about 0.05% cyclosporin A, Polysorbate 40, and eucalpytus oil.
Another embodiment comprises about 0.05% cyclosporin A, Polysorbate 40, and sesame oil.
Another embodiment comprises about 0.05% cyclosporin A, Polysorbate 40, and an oil having a specific gravity below 0.9.
Another embodiment comprises about 0.05% cyclosporin A, Polysorbate 40, and mineral oil.
Another embodiment comprises about 0.05% cyclosporin A, Polysorbate 40, and coriander oil.
Another embodiment comprises about 0.05% cyclosporin A, Polysorbate 40, and lavender oil.
Another embodiment comprises about 0.05% cyclosporin A, Polysorbate 40, and citronella oil.
Another embodiment comprises about 0.05% cyclosporin A, Polysorbate 40, and juniper oil.
Another embodiment comprises about 0.05% cyclosporin A, Polysorbate 40, and lemon oil.
Another embodiment comprises about 0.05% cyclosporin A, Polysorbate 40, and orange oil.
Another embodiment comprises about 0.05% cyclosporin A, Polysorbate 40, and clary sage oil.
Another embodiment comprises about 0.05% cyclosporin A, Polysorbate 40, and nutmeg oil.
Another embodiment comprises about 0.05% cyclosporin A, Polysorbate 40, and tea tree oil.
Another embodiment comprises about 0.05% cyclosporin A, Polysorbate 60, and an oil having a specific gravity between 0.90 and 0.95.
Another embodiment comprises about 0.05% cyclosporin A, Polysorbate 60, and almond oil.
Another embodiment comprises about 0.05% cyclosporin A, Polysorbate 60, and corn oil.
Another embodiment comprises about 0.05% cyclosporin A, Polysorbate 60, and arachis oil.
Another embodiment comprises about 0.05% cyclosporin A, Polysorbate 60, and cottonseed oil.
Another embodiment comprises about 0.05% cyclosporin A, Polysorbate 60, and safflower oil.
Another embodiment comprises about 0.05% cyclosporin A, Polysorbate 60, and maize oil.
Another embodiment comprises about 0.05% cyclosporin A, Polysorbate 60, and linseed oil.
Another embodiment comprises about 0.05% cyclosporin A, Polysorbate 60, and rapeseed oil.

Another embodiment comprises about 0.05% cyclosporin A, Polysorbate 60, and soybean oil.

Another embodiment comprises about 0.05% cyclosporin A, Polysorbate 60, and olive oil.

Another embodiment comprises about 0.05% cyclosporin A, Polysorbate 60, and caraway oil.

Another embodiment comprises about 0.05% cyclosporin A, Polysorbate 60, and rosemary oil.

Another embodiment comprises about 0.05% cyclosporin A, Polysorbate 60, and peanut oil.

Another embodiment comprises about 0.05% cyclosporin A, Polysorbate 60, and peppermint oil.

Another embodiment comprises about 0.05% cyclosporin A, Polysorbate 60, and sunflower oil.

Another embodiment comprises about 0.05% cyclosporin A, Polysorbate 60, and eucalpytus oil.

Another embodiment comprises about 0.05% cyclosporin A, Polysorbate 60, and sesame oil.

Another embodiment comprises about 0.05% cyclosporin A, Polysorbate 60, and an oil having a specific gravity below 0.9.

Another embodiment comprises about 0.05% cyclosporin A, Polysorbate 60, and mineral oil.

Another embodiment comprises about 0.05% cyclosporin A, Polysorbate 60, and coriander oil.

Another embodiment comprises about 0.05% cyclosporin A, Polysorbate 60, and lavender oil.

Another embodiment comprises about 0.05% cyclosporin A, Polysorbate 60, and citronella oil.

Another embodiment comprises about 0.05% cyclosporin A, Polysorbate 60, and juniper oil.

Another embodiment comprises about 0.05% cyclosporin A, Polysorbate 60, and lemon oil.

Another embodiment comprises about 0.05% cyclosporin A, Polysorbate 60, and orange oil.

Another embodiment comprises about 0.05% cyclosporin A, Polysorbate 60, and clary sage oil.

Another embodiment comprises about 0.05% cyclosporin A, Polysorbate 60, and nutmeg oil.

Another embodiment comprises about 0.05% cyclosporin A, Polysorbate 60, and tea tree oil.

Another embodiment comprises about 0.05% cyclosporin A, Polysorbate 80, and an oil having a specific gravity between 0.90 and 0.95.

Another embodiment comprises about 0.05% cyclosporin A, Polysorbate 80, and almond oil.

Another embodiment comprises about 0.05% cyclosporin A, Polysorbate 80, and corn oil.

Another embodiment comprises about 0.05% cyclosporin A, Polysorbate 80, and arachis oil.

Another embodiment comprises about 0.05% cyclosporin A, Polysorbate 80, and cottonseed oil.

Another embodiment comprises about 0.05% cyclosporin A, Polysorbate 80, and safflower oil.

Another embodiment comprises about 0.05% cyclosporin A, Polysorbate 80, and maize oil.

Another embodiment comprises about 0.05% cyclosporin A, Polysorbate 80, and linseed oil.

Another embodiment comprises about 0.05% cyclosporin A, Polysorbate 80, and rapeseed oil.

Another embodiment comprises about 0.05% cyclosporin A, Polysorbate 80, and soybean oil.

Another embodiment comprises about 0.05% cyclosporin A, Polysorbate 80, and olive oil.

Another embodiment comprises about 0.05% cyclosporin A, Polysorbate 80, and caraway oil.

Another embodiment comprises about 0.05% cyclosporin A, Polysorbate 80, and rosemary oil.

Another embodiment comprises about 0.05% cyclosporin A, Polysorbate 80, and peanut oil.

Another embodiment comprises about 0.05% cyclosporin A, Polysorbate 80, and peppermint oil.

Another embodiment comprises about 0.05% cyclosporin A, Polysorbate 80, and sunflower oil.

Another embodiment comprises about 0.05% cyclosporin A, Polysorbate 80, and eucalpytus oil.

Another embodiment comprises about 0.05% cyclosporin A, Polysorbate 80, and sesame oil.

Another embodiment comprises about 0.05% cyclosporin A, Polysorbate 80, and an oil having a specific gravity below 0.9.

Another embodiment comprises about 0.05% cyclosporin A, Polysorbate 80, and mineral oil.

Another embodiment comprises about 0.05% cyclosporin A, Polysorbate 80, and coriander oil.

Another embodiment comprises about 0.05% cyclosporin A, Polysorbate 80, and lavender oil.

Another embodiment comprises about 0.05% cyclosporin A, Polysorbate 80, and citronella oil.

Another embodiment comprises about 0.05% cyclosporin A, Polysorbate 80, and juniper oil.

Another embodiment comprises about 0.05% cyclosporin A, Polysorbate 80, and lemon oil.

Another embodiment comprises about 0.05% cyclosporin A, Polysorbate 80, and orange oil.

Another embodiment comprises about 0.05% cyclosporin A, Polysorbate 80, and clary sage oil.

Another embodiment comprises about 0.05% cyclosporin A, Polysorbate 80, and nutmeg oil.

Another embodiment comprises about 0.05% cyclosporin A, Polysorbate 80, and tea tree oil.

Another embodiment comprises about 0.05% cyclosporin A, a stearate, and an oil having a specific gravity between 0.90 and 0.95.

Another embodiment comprises about 0.05% cyclosporin A, a stearate, and almond oil.

Another embodiment comprises about 0.05% cyclosporin A, a stearate, and corn oil.

Another embodiment comprises about 0.05% cyclosporin A, a stearate, and arachis oil.

Another embodiment comprises about 0.05% cyclosporin A, a stearate, and cottonseed oil.

Another embodiment comprises about 0.05% cyclosporin A, a stearate, and safflower oil.

Another embodiment comprises about 0.05% cyclosporin A, a stearate, and maize oil.

Another embodiment comprises about 0.05% cyclosporin A, a stearate, and linseed oil.

Another embodiment comprises about 0.05% cyclosporin A, a stearate, and rapeseed oil.

Another embodiment comprises about 0.05% cyclosporin A, a stearate, and soybean oil.

Another embodiment comprises about 0.05% cyclosporin A, a stearate, and olive oil.

Another embodiment comprises about 0.05% cyclosporin A, a stearate, and caraway oil.

Another embodiment comprises about 0.05% cyclosporin A, a stearate, and rosemary oil.

Another embodiment comprises about 0.05% cyclosporin A, a stearate, and peanut oil.

Another embodiment comprises about 0.05% cyclosporin A, a stearate, and peppermint oil.

Another embodiment comprises about 0.05% cyclosporin A, a stearate, and sunflower oil.

Another embodiment comprises about 0.05% cyclosporin A, a stearate, and eucalpytus oil.

Another embodiment comprises about 0.05% cyclosporin A, a stearate, and sesame oil.

Another embodiment comprises about 0.05% cyclosporin A, a stearate, and an oil having a specific gravity below 0.9.

Another embodiment comprises about 0.05% cyclosporin A, a stearate, and mineral oil.

Another embodiment comprises about 0.05% cyclosporin A, a stearate, and coriander oil.

Another embodiment comprises about 0.05% cyclosporin A, a stearate, and lavender oil.

Another embodiment comprises about 0.05% cyclosporin A, a stearate, and citronella oil.

Another embodiment comprises about 0.05% cyclosporin A, a stearate, and juniper oil.

Another embodiment comprises about 0.05% cyclosporin A, a stearate, and lemon oil.

Another embodiment comprises about 0.05% cyclosporin A, a stearate, and orange oil.

Another embodiment comprises about 0.05% cyclosporin A, a stearate, and clary sage oil.

Another embodiment comprises about 0.05% cyclosporin A, a stearate, and nutmeg oil.

Another embodiment comprises about 0.05% cyclosporin A, a stearate, and tea tree oil.

Another embodiment comprises about 0.05% cyclosporin A, glyceryl stearate, and an oil having a specific gravity between 0.90 and 0.95.

Another embodiment comprises about 0.05% cyclosporin A, glyceryl stearate, and almond oil.

Another embodiment comprises about 0.05% cyclosporin A, glyceryl stearate, and corn oil.

Another embodiment comprises about 0.05% cyclosporin A, glyceryl stearate, and arachis oil.

Another embodiment comprises about 0.05% cyclosporin A, glyceryl stearate, and cottonseed oil.

Another embodiment comprises about 0.05% cyclosporin A, glyceryl stearate, and safflower oil.

Another embodiment comprises about 0.05% cyclosporin A, glyceryl stearate, and maize oil.

Another embodiment comprises about 0.05% cyclosporin A, glyceryl stearate, and linseed oil.

Another embodiment comprises about 0.05% cyclosporin A, glyceryl stearate, and rapeseed oil.

Another embodiment comprises about 0.05% cyclosporin A, glyceryl stearate, and soybean oil.

Another embodiment comprises about 0.05% cyclosporin A, glyceryl stearate, and olive oil.

Another embodiment comprises about 0.05% cyclosporin A, glyceryl stearate, and caraway oil.

Another embodiment comprises about 0.05% cyclosporin A, glyceryl stearate, and rosemary oil.

Another embodiment comprises about 0.05% cyclosporin A, glyceryl stearate, and peanut oil.

Another embodiment comprises about 0.05% cyclosporin A, glyceryl stearate, and peppermint oil.

Another embodiment comprises about 0.05% cyclosporin A, glyceryl stearate, and sunflower oil.

Another embodiment comprises about 0.05% cyclosporin A, glyceryl stearate, and eucalpytus oil.

Another embodiment comprises about 0.05% cyclosporin A, glyceryl stearate, and sesame oil.

Another embodiment comprises about 0.05% cyclosporin A, glyceryl stearate, and an oil having a specific gravity below 0.9.

Another embodiment comprises about 0.05% cyclosporin A, glyceryl stearate, and mineral oil.

Another embodiment comprises about 0.05% cyclosporin A, glyceryl stearate, and coriander oil.

Another embodiment comprises about 0.05% cyclosporin A, glyceryl stearate, and lavender oil.

Another embodiment comprises about 0.05% cyclosporin A, glyceryl stearate, and citronella oil.

Another embodiment comprises about 0.05% cyclosporin A, glyceryl stearate, and juniper oil.

Another embodiment comprises about 0.05% cyclosporin A, glyceryl stearate, and lemon oil.

Another embodiment comprises about 0.05% cyclosporin A, glyceryl stearate, and orange oil.

Another embodiment comprises about 0.05% cyclosporin A, glyceryl stearate, and clary sage oil.

Another embodiment comprises about 0.05% cyclosporin A, glyceryl stearate, and nutmeg oil.

Another embodiment comprises about 0.05% cyclosporin A, glyceryl stearate, and tea tree oil.

Another embodiment comprises about 0.05% cyclosporin A, isopropyl stearate, and an oil having a specific gravity between 0.90 and 0.95.

Another embodiment comprises about 0.05% cyclosporin A, isopropyl stearate, and almond oil.

Another embodiment comprises about 0.05% cyclosporin A, isopropyl stearate, and corn oil.

Another embodiment comprises about 0.05% cyclosporin A, isopropyl stearate, and arachis oil.

Another embodiment comprises about 0.05% cyclosporin A, isopropyl stearate, and cottonseed oil.

Another embodiment comprises about 0.05% cyclosporin A, isopropyl stearate, and safflower oil.

Another embodiment comprises about 0.05% cyclosporin A, isopropyl stearate, and maize oil.

Another embodiment comprises about 0.05% cyclosporin A, isopropyl stearate, and linseed oil.

Another embodiment comprises about 0.05% cyclosporin A, isopropyl stearate, and rapeseed oil.

Another embodiment comprises about 0.05% cyclosporin A, isopropyl stearate, and soybean oil.

Another embodiment comprises about 0.05% cyclosporin A, isopropyl stearate, and olive oil.

Another embodiment comprises about 0.05% cyclosporin A, isopropyl stearate, and caraway oil.

Another embodiment comprises about 0.05% cyclosporin A, isopropyl stearate, and rosemary oil.

Another embodiment comprises about 0.05% cyclosporin A, isopropyl stearate, and peanut oil.

Another embodiment comprises about 0.05% cyclosporin A, isopropyl stearate, and peppermint oil.

Another embodiment comprises about 0.05% cyclosporin A, isopropyl stearate, and sunflower oil.

Another embodiment comprises about 0.05% cyclosporin A, isopropyl stearate, and eucalpytus oil.

Another embodiment comprises about 0.05% cyclosporin A, isopropyl stearate, and sesame oil.

Another embodiment comprises about 0.05% cyclosporin A, isopropyl stearate, and an oil having a specific gravity below 0.9.

Another embodiment comprises about 0.05% cyclosporin A, isopropyl stearate, and mineral oil.

Another embodiment comprises about 0.05% cyclosporin A, isopropyl stearate, and coriander oil.

Another embodiment comprises about 0.05% cyclosporin A, isopropyl stearate, and lavender oil.

Another embodiment comprises about 0.05% cyclosporin A, isopropyl stearate, and citronella oil.

Another embodiment comprises about 0.05% cyclosporin A, isopropyl stearate, and juniper oil.

Another embodiment comprises about 0.05% cyclosporin A, isopropyl stearate, and lemon oil.

Another embodiment comprises about 0.05% cyclosporin A, isopropyl stearate, and orange oil.

Another embodiment comprises about 0.05% cyclosporin A, isopropyl stearate, and clary sage oil.

Another embodiment comprises about 0.05% cyclosporin A, isopropyl stearate, and nutmeg oil.

Another embodiment comprises about 0.05% cyclosporin A, isopropyl stearate, and tea tree oil.

Another embodiment comprises about 0.05% cyclosporin A, polyoxyl stearate, and an oil having a specific gravity between 0.90 and 0.95.

Another embodiment comprises about 0.05% cyclosporin A, polyoxyl stearate, and almond oil.

Another embodiment comprises about 0.05% cyclosporin A, polyoxyl stearate, and corn oil.

Another embodiment comprises about 0.05% cyclosporin A, polyoxyl stearate, and arachis oil.

Another embodiment comprises about 0.05% cyclosporin A, polyoxyl stearate, and cottonseed oil.

Another embodiment comprises about 0.05% cyclosporin A, polyoxyl stearate, and safflower oil.

Another embodiment comprises about 0.05% cyclosporin A, polyoxyl stearate, and maize oil.

Another embodiment comprises about 0.05% cyclosporin A, polyoxyl stearate, and linseed oil.

Another embodiment comprises about 0.05% cyclosporin A, polyoxyl stearate, and rapeseed oil.

Another embodiment comprises about 0.05% cyclosporin A, polyoxyl stearate, and soybean oil.

Another embodiment comprises about 0.05% cyclosporin A, polyoxyl stearate, and olive oil.

Another embodiment comprises about 0.05% cyclosporin A, polyoxyl stearate, and caraway oil.

Another embodiment comprises about 0.05% cyclosporin A, polyoxyl stearate, and rosemary oil.

Another embodiment comprises about 0.05% cyclosporin A, polyoxyl stearate, and peanut oil.

Another embodiment comprises about 0.05% cyclosporin A, polyoxyl stearate, and peppermint oil.

Another embodiment comprises about 0.05% cyclosporin A, polyoxyl stearate, and sunflower oil.

Another embodiment comprises about 0.05% cyclosporin A, polyoxyl stearate, and eucalpytus oil.

Another embodiment comprises about 0.05% cyclosporin A, polyoxyl stearate, and sesame oil.

Another embodiment comprises about 0.05% cyclosporin A, polyoxyl stearate, and an oil having a specific gravity below 0.9.

Another embodiment comprises about 0.05% cyclosporin A, polyoxyl stearate, and mineral oil.

Another embodiment comprises about 0.05% cyclosporin A, polyoxyl stearate, and coriander oil.

Another embodiment comprises about 0.05% cyclosporin A, polyoxyl stearate, and lavender oil.

Another embodiment comprises about 0.05% cyclosporin A, polyoxyl stearate, and citronella oil.

Another embodiment comprises about 0.05% cyclosporin A, polyoxyl stearate, and juniper oil.

Another embodiment comprises about 0.05% cyclosporin A, polyoxyl stearate, and lemon oil.

Another embodiment comprises about 0.05% cyclosporin A, polyoxyl stearate, and orange oil.

Another embodiment comprises about 0.05% cyclosporin A, polyoxyl stearate, and clary sage oil.

Another embodiment comprises about 0.05% cyclosporin A, polyoxyl stearate, and nutmeg oil.

Another embodiment comprises about 0.05% cyclosporin A, polyoxyl stearate, and tea tree oil.

Another embodiment comprises about 0.05% cyclosporin A, propylene glycol stearate, and an oil having a specific gravity between 0.90 and 0.95.

Another embodiment comprises about 0.05% cyclosporin A, propylene glycol stearate, and almond oil.

Another embodiment comprises about 0.05% cyclosporin A, propylene glycol stearate, and corn oil.

Another embodiment comprises about 0.05% cyclosporin A, propylene glycol stearate, and arachis oil.

Another embodiment comprises about 0.05% cyclosporin A, propylene glycol stearate, and cottonseed oil.

Another embodiment comprises about 0.05% cyclosporin A, propylene glycol stearate, and safflower oil.

Another embodiment comprises about 0.05% cyclosporin A, propylene glycol stearate, and maize oil.

Another embodiment comprises about 0.05% cyclosporin A, propylene glycol stearate, and linseed oil.

Another embodiment comprises about 0.05% cyclosporin A, propylene glycol stearate, and rapeseed oil.

Another embodiment comprises about 0.05% cyclosporin A, propylene glycol stearate, and soybean oil.

Another embodiment comprises about 0.05% cyclosporin A, propylene glycol stearate, and olive oil.

Another embodiment comprises about 0.05% cyclosporin A, propylene glycol stearate, and caraway oil.

Another embodiment comprises about 0.05% cyclosporin A, propylene glycol stearate, and rosemary oil.

Another embodiment comprises about 0.05% cyclosporin A, propylene glycol stearate, and peanut oil.

Another embodiment comprises about 0.05% cyclosporin A, propylene glycol stearate, and peppermint oil.

Another embodiment comprises about 0.05% cyclosporin A, propylene glycol stearate, and sunflower oil.

Another embodiment comprises about 0.05% cyclosporin A, propylene glycol stearate, and eucalpytus oil.

Another embodiment comprises about 0.05% cyclosporin A, propylene glycol stearate, and sesame oil.

Another embodiment comprises about 0.05% cyclosporin A, propylene glycol stearate, and an oil having a specific gravity below 0.9.

Another embodiment comprises about 0.05% cyclosporin A, propylene glycol stearate, and mineral oil.

Another embodiment comprises about 0.05% cyclosporin A, propylene glycol stearate, and coriander oil.

Another embodiment comprises about 0.05% cyclosporin A, propylene glycol stearate, and lavender oil.

Another embodiment comprises about 0.05% cyclosporin A, propylene glycol stearate, and citronella oil.

Another embodiment comprises about 0.05% cyclosporin A, propylene glycol stearate, and juniper oil.

Another embodiment comprises about 0.05% cyclosporin A, propylene glycol stearate, and lemon oil.

Another embodiment comprises about 0.05% cyclosporin A, propylene glycol stearate, and orange oil.

Another embodiment comprises about 0.05% cyclosporin A, propylene glycol stearate, and clary sage oil.

Another embodiment comprises about 0.05% cyclosporin A, propylene glycol stearate, and nutmeg oil.
Another embodiment comprises about 0.05% cyclosporin A, propylene glycol stearate, and tea tree oil.
Another embodiment comprises about 0.05% cyclosporin A, sucrose stearate, and an oil having a specific gravity between 0.90 and 0.95.
Another embodiment comprises about 0.05% cyclosporin A, sucrose stearate, and almond oil.
Another embodiment comprises about 0.05% cyclosporin A, sucrose stearate, and corn oil.
Another embodiment comprises about 0.05% cyclosporin A, sucrose stearate, and arachis oil.
Another embodiment comprises about 0.05% cyclosporin A, sucrose stearate, and cottonseed oil.
Another embodiment comprises about 0.05% cyclosporin A, sucrose stearate, and safflower oil.
Another embodiment comprises about 0.05% cyclosporin A, sucrose stearate, and maize oil.
Another embodiment comprises about 0.05% cyclosporin A, sucrose stearate, and linseed oil.
Another embodiment comprises about 0.05% cyclosporin A, sucrose stearate, and rapeseed oil.
Another embodiment comprises about 0.05% cyclosporin A, sucrose stearate, and soybean oil.
Another embodiment comprises about 0.05% cyclosporin A, sucrose stearate, and olive oil.
Another embodiment comprises about 0.05% cyclosporin A, sucrose stearate, and caraway oil.
Another embodiment comprises about 0.05% cyclosporin A, sucrose stearate, and rosemary oil.
Another embodiment comprises about 0.05% cyclosporin A, sucrose stearate, and peanut oil.
Another embodiment comprises about 0.05% cyclosporin A, sucrose stearate, and peppermint oil.
Another embodiment comprises about 0.05% cyclosporin A, sucrose stearate, and sunflower oil.
Another embodiment comprises about 0.05% cyclosporin A, sucrose stearate, and eucalpytus oil.
Another embodiment comprises about 0.05% cyclosporin A, sucrose stearate, and sesame oil.
Another embodiment comprises about 0.05% cyclosporin A, sucrose stearate, and an oil having a specific gravity below 0.9.
Another embodiment comprises about 0.05% cyclosporin A, sucrose stearate, and mineral oil.
Another embodiment comprises about 0.05% cyclosporin A, sucrose stearate, and coriander oil.
Another embodiment comprises about 0.05% cyclosporin A, sucrose stearate, and lavender oil.
Another embodiment comprises about 0.05% cyclosporin A, sucrose stearate, and citronella oil.
Another embodiment comprises about 0.05% cyclosporin A, sucrose stearate, and juniper oil.
Another embodiment comprises about 0.05% cyclosporin A, sucrose stearate, and lemon oil.
Another embodiment comprises about 0.05% cyclosporin A, sucrose stearate, and orange oil.
Another embodiment comprises about 0.05% cyclosporin A, sucrose stearate, and clary sage oil.
Another embodiment comprises about 0.05% cyclosporin A, sucrose stearate, and nutmeg oil.
Another embodiment comprises about 0.05% cyclosporin A, sucrose stearate, and tea tree oil.
Another embodiment comprises about 0.05% cyclosporin A, polyethylene glycol, and an oil having a specific gravity between 0.90 and 0.95.
Another embodiment comprises about 0.05% cyclosporin A, polyethylene glycol, and almond oil.
Another embodiment comprises about 0.05% cyclosporin A, polyethylene glycol, and corn oil.
Another embodiment comprises about 0.05% cyclosporin A, polyethylene glycol, and arachis oil.
Another embodiment comprises about 0.05% cyclosporin A, polyethylene glycol, and cottonseed oil.
Another embodiment comprises about 0.05% cyclosporin A, polyethylene glycol, and safflower oil.
Another embodiment comprises about 0.05% cyclosporin A, polyethylene glycol, and maize oil.
Another embodiment comprises about 0.05% cyclosporin A, polyethylene glycol, and linseed oil.
Another embodiment comprises about 0.05% cyclosporin A, polyethylene glycol, and rapeseed oil.
Another embodiment comprises about 0.05% cyclosporin A, polyethylene glycol, and soybean oil.
Another embodiment comprises about 0.05% cyclosporin A, polyethylene glycol, and olive oil.
Another embodiment comprises about 0.05% cyclosporin A, polyethylene glycol, and caraway oil.
Another embodiment comprises about 0.05% cyclosporin A, polyethylene glycol, and rosemary oil.
Another embodiment comprises about 0.05% cyclosporin A, polyethylene glycol, and peanut oil.
Another embodiment comprises about 0.05% cyclosporin A, polyethylene glycol, and peppermint oil.
Another embodiment comprises about 0.05% cyclosporin A, polyethylene glycol, and sunflower oil.
Another embodiment comprises about 0.05% cyclosporin A, polyethylene glycol, and eucalpytus oil.
Another embodiment comprises about 0.05% cyclosporin A, polyethylene glycol, and sesame oil.
Another embodiment comprises about 0.05% cyclosporin A, polyethylene glycol, and an oil having a specific gravity below 0.9.
Another embodiment comprises about 0.05% cyclosporin A, polyethylene glycol, and mineral oil.
Another embodiment comprises about 0.05% cyclosporin A, polyethylene glycol, and coriander oil.
Another embodiment comprises about 0.05% cyclosporin A, polyethylene glycol, and lavender oil.
Another embodiment comprises about 0.05% cyclosporin A, polyethylene glycol, and citronella oil.
Another embodiment comprises about 0.05% cyclosporin A, polyethylene glycol, and juniper oil.
Another embodiment comprises about 0.05% cyclosporin A, polyethylene glycol, and lemon oil.
Another embodiment comprises about 0.05% cyclosporin A, polyethylene glycol, and orange oil.
Another embodiment comprises about 0.05% cyclosporin A, polyethylene glycol, and clary sage oil.
Another embodiment comprises about 0.05% cyclosporin A, polyethylene glycol, and nutmeg oil.
Another embodiment comprises about 0.05% cyclosporin A, polyethylene glycol, and tea tree oil.
Another embodiment comprises about 0.05% cyclosporin A, polyethylene oxide, and an oil having a specific gravity between 0.90 and 0.95.
Another embodiment comprises about 0.05% cyclosporin A, polyethylene oxide, and almond oil.
Another embodiment comprises about 0.05% cyclosporin A, polyethylene oxide, and corn oil.
Another embodiment comprises about 0.05% cyclosporin A, polyethylene oxide, and arachis oil.

Another embodiment comprises about 0.05% cyclosporin A, polyethylene oxide, and cottonseed oil.

Another embodiment comprises about 0.05% cyclosporin A, polyethylene oxide, and safflower oil.

Another embodiment comprises about 0.05% cyclosporin A, polyethylene oxide, and maize oil.

Another embodiment comprises about 0.05% cyclosporin A, polyethylene oxide, and linseed oil.

Another embodiment comprises about 0.05% cyclosporin A, polyethylene oxide, and rapeseed oil.

Another embodiment comprises about 0.05% cyclosporin A, polyethylene oxide, and soybean oil.

Another embodiment comprises about 0.05% cyclosporin A, polyethylene oxide, and olive oil.

Another embodiment comprises about 0.05% cyclosporin A, polyethylene oxide, and caraway oil.

Another embodiment comprises about 0.05% cyclosporin A, polyethylene oxide, and rosemary oil.

Another embodiment comprises about 0.05% cyclosporin A, polyethylene oxide, and peanut oil.

Another embodiment comprises about 0.05% cyclosporin A, polyethylene oxide, and peppermint oil.

Another embodiment comprises about 0.05% cyclosporin A, polyethylene oxide, and sunflower oil.

Another embodiment comprises about 0.05% cyclosporin A, polyethylene oxide, and eucalpytus oil.

Another embodiment comprises about 0.05% cyclosporin A, polyethylene oxide, and sesame oil.

Another embodiment comprises about 0.05% cyclosporin A, polyethylene oxide, and an oil having a specific gravity below 0.9.

Another embodiment comprises about 0.05% cyclosporin A, polyethylene oxide, and mineral oil.

Another embodiment comprises about 0.05% cyclosporin A, polyethylene oxide, and coriander oil.

Another embodiment comprises about 0.05% cyclosporin A, polyethylene oxide, and lavender oil.

Another embodiment comprises about 0.05% cyclosporin A, polyethylene oxide, and citronella oil.

Another embodiment comprises about 0.05% cyclosporin A, polyethylene oxide, and juniper oil.

Another embodiment comprises about 0.05% cyclosporin A, polyethylene oxide, and lemon oil.

Another embodiment comprises about 0.05% cyclosporin A, polyethylene oxide, and orange oil.

Another embodiment comprises about 0.05% cyclosporin A, polyethylene oxide, and clary sage oil.

Another embodiment comprises about 0.05% cyclosporin A, polyethylene oxide, and nutmeg oil.

Another embodiment comprises about 0.05% cyclosporin A, polyethylene oxide, and tea tree oil.

Another embodiment comprises about 0.05% cyclosporin A, polypropylene oxide, and an oil having a specific gravity between 0.90 and 0.95.

Another embodiment comprises about 0.05% cyclosporin A, polypropylene oxide, and almond oil.

Another embodiment comprises about 0.05% cyclosporin A, polypropylene oxide, and corn oil.

Another embodiment comprises about 0.05% cyclosporin A, polypropylene oxide, and arachis oil.

Another embodiment comprises about 0.05% cyclosporin A, polypropylene oxide, and cottonseed oil.

Another embodiment comprises about 0.05% cyclosporin A, polypropylene oxide, and safflower oil.

Another embodiment comprises about 0.05% cyclosporin A, polypropylene oxide, and maize oil.

Another embodiment comprises about 0.05% cyclosporin A, polypropylene oxide, and linseed oil.

Another embodiment comprises about 0.05% cyclosporin A, polypropylene oxide, and rapeseed oil.

Another embodiment comprises about 0.05% cyclosporin A, polypropylene oxide, and soybean oil.

Another embodiment comprises about 0.05% cyclosporin A, polypropylene oxide, and olive oil.

Another embodiment comprises about 0.05% cyclosporin A, polypropylene oxide, and caraway oil.

Another embodiment comprises about 0.05% cyclosporin A, polypropylene oxide, and rosemary oil.

Another embodiment comprises about 0.05% cyclosporin A, polypropylene oxide, and peanut oil.

Another embodiment comprises about 0.05% cyclosporin A, polypropylene oxide, and peppermint oil.

Another embodiment comprises about 0.05% cyclosporin A, polypropylene oxide, and sunflower oil.

Another embodiment comprises about 0.05% cyclosporin A, polypropylene oxide, and eucalpytus oil.

Another embodiment comprises about 0.05% cyclosporin A, polypropylene oxide, and sesame oil.

Another embodiment comprises about 0.05% cyclosporin A, polypropylene oxide, and an oil having a specific gravity below 0.9.

Another embodiment comprises about 0.05% cyclosporin A, polypropylene oxide, and mineral oil.

Another embodiment comprises about 0.05% cyclosporin A, polypropylene oxide, and coriander oil.

Another embodiment comprises about 0.05% cyclosporin A, polypropylene oxide, and lavender oil.

Another embodiment comprises about 0.05% cyclosporin A, polypropylene oxide, and citronella oil.

Another embodiment comprises about 0.05% cyclosporin A, polypropylene oxide, and juniper oil.

Another embodiment comprises about 0.05% cyclosporin A, polypropylene oxide, and lemon oil.

Another embodiment comprises about 0.05% cyclosporin A, polypropylene oxide, and orange oil.

Another embodiment comprises about 0.05% cyclosporin A, polypropylene oxide, and clary sage oil.

Another embodiment comprises about 0.05% cyclosporin A, polypropylene oxide, and nutmeg oil.

Another embodiment comprises about 0.05% cyclosporin A, polypropylene oxide, and tea tree oil.

Another embodiment comprises about 0.05% cyclosporin A, a polyethylene oxide-polypropylene oxide copolymer, and an oil having a specific gravity between 0.90 and 0.95.

Another embodiment comprises about 0.05% cyclosporin A, a polyethylene oxide-polypropylene oxide copolymer, and almond oil.

Another embodiment comprises about 0.05% cyclosporin A, a polyethylene oxide-polypropylene oxide copolymer, and corn oil.

Another embodiment comprises about 0.05% cyclosporin A, a polyethylene oxide-polypropylene oxide copolymer, and arachis oil.

Another embodiment comprises about 0.05% cyclosporin A, a polyethylene oxide-polypropylene oxide copolymer, and cottonseed oil.

Another embodiment comprises about 0.05% cyclosporin A, a polyethylene oxide-polypropylene oxide copolymer, and safflower oil.

Another embodiment comprises about 0.05% cyclosporin A, a polyethylene oxide-polypropylene oxide copolymer, and maize oil.

Another embodiment comprises about 0.05% cyclosporin A, a polyethylene oxide-polypropylene oxide copolymer, and linseed oil.

Another embodiment comprises about 0.05% cyclosporin A, a polyethylene oxide-polypropylene oxide copolymer, and rapeseed oil.

Another embodiment comprises about 0.05% cyclosporin A, a polyethylene oxide-polypropylene oxide copolymer, and soybean oil.

Another embodiment comprises about 0.05% cyclosporin A, a polyethylene oxide-polypropylene oxide copolymer, and olive oil.

Another embodiment comprises about 0.05% cyclosporin A, a polyethylene oxide-polypropylene oxide copolymer, and caraway oil.

Another embodiment comprises about 0.05% cyclosporin A, a polyethylene oxide-polypropylene oxide copolymer, and rosemary oil.

Another embodiment comprises about 0.05% cyclosporin A, a polyethylene oxide-polypropylene oxide copolymer, and peanut oil.

Another embodiment comprises about 0.05% cyclosporin A, a polyethylene oxide-polypropylene oxide copolymer, and peppermint oil.

Another embodiment comprises about 0.05% cyclosporin A, a polyethylene oxide-polypropylene oxide copolymer, and sunflower oil.

Another embodiment comprises about 0.05% cyclosporin A, a polyethylene oxide-polypropylene oxide copolymer, and eucalpytus oil.

Another embodiment comprises about 0.05% cyclosporin A, a polyethylene oxide-polypropylene oxide copolymer, and sesame oil.

Another embodiment comprises about 0.05% cyclosporin A, a polyethylene oxide-polypropylene oxide copolymer, and an oil having a specific gravity below 0.9.

Another embodiment comprises about 0.05% cyclosporin A, a polyethylene oxide-polypropylene oxide copolymer, and mineral oil.

Another embodiment comprises about 0.05% cyclosporin A, a polyethylene oxide-polypropylene oxide copolymer, and coriander oil.

Another embodiment comprises about 0.05% cyclosporin A, a polyethylene oxide-polypropylene oxide copolymer, and lavender oil.

Another embodiment comprises about 0.05% cyclosporin A, a polyethylene oxide-polypropylene oxide copolymer, and citronella oil.

Another embodiment comprises about 0.05% cyclosporin A, a polyethylene oxide-polypropylene oxide copolymer, and juniper oil.

Another embodiment comprises about 0.05% cyclosporin A, a polyethylene oxide-polypropylene oxide copolymer, and lemon oil.

Another embodiment comprises about 0.05% cyclosporin A, a polyethylene oxide-polypropylene oxide copolymer, and orange oil.

Another embodiment comprises about 0.05% cyclosporin A, a polyethylene oxide-polypropylene oxide copolymer, and clary sage oil.

Another embodiment comprises about 0.05% cyclosporin A, a polyethylene oxide-polypropylene oxide copolymer, and nutmeg oil.

Another embodiment comprises about 0.05% cyclosporin A, a polyethylene oxide-polypropylene oxide copolymer, and tea tree oil.

Another embodiment comprises about 0.05% cyclosporin A, an alcohol ethoxylate, and an oil having a specific gravity between 0.90 and 0.95.

Another embodiment comprises about 0.05% cyclosporin A, an alcohol ethoxylate, and almond oil.

Another embodiment comprises about 0.05% cyclosporin A, an alcohol ethoxylate, and corn oil.

Another embodiment comprises about 0.05% cyclosporin A, an alcohol ethoxylate, and arachis oil.

Another embodiment comprises about 0.05% cyclosporin A, an alcohol ethoxylate, and cottonseed oil.

Another embodiment comprises about 0.05% cyclosporin A, an alcohol ethoxylate, and safflower oil.

Another embodiment comprises about 0.05% cyclosporin A, an alcohol ethoxylate, and maize oil.

Another embodiment comprises about 0.05% cyclosporin A, an alcohol ethoxylate, and linseed oil.

Another embodiment comprises about 0.05% cyclosporin A, an alcohol ethoxylate, and rapeseed oil.

Another embodiment comprises about 0.05% cyclosporin A, an alcohol ethoxylate, and soybean oil.

Another embodiment comprises about 0.05% cyclosporin A, an alcohol ethoxylate, and olive oil.

Another embodiment comprises about 0.05% cyclosporin A, an alcohol ethoxylate, and caraway oil.

Another embodiment comprises about 0.05% cyclosporin A, an alcohol ethoxylate, and rosemary oil.

Another embodiment comprises about 0.05% cyclosporin A, an alcohol ethoxylate, and peanut oil.

Another embodiment comprises about 0.05% cyclosporin A, an alcohol ethoxylate, and peppermint oil.

Another embodiment comprises about 0.05% cyclosporin A, an alcohol ethoxylate, and sunflower oil.

Another embodiment comprises about 0.05% cyclosporin A, an alcohol ethoxylate, and eucalpytus oil.

Another embodiment comprises about 0.05% cyclosporin A, an alcohol ethoxylate, and sesame oil.

Another embodiment comprises about 0.05% cyclosporin A, an alcohol ethoxylate, and an oil having a specific gravity below 0.9.

Another embodiment comprises about 0.05% cyclosporin A, an alcohol ethoxylate, and mineral oil.

Another embodiment comprises about 0.05% cyclosporin A, an alcohol ethoxylate, and coriander oil.

Another embodiment comprises about 0.05% cyclosporin A, an alcohol ethoxylate, and lavender oil.

Another embodiment comprises about 0.05% cyclosporin A, an alcohol ethoxylate, and citronella oil.

Another embodiment comprises about 0.05% cyclosporin A, an alcohol ethoxylate, and juniper oil.

Another embodiment comprises about 0.05% cyclosporin A, an alcohol ethoxylate, and lemon oil.

Another embodiment comprises about 0.05% cyclosporin A, an alcohol ethoxylate, and orange oil.

Another embodiment comprises about 0.05% cyclosporin A, an alcohol ethoxylate, and clary sage oil.

Another embodiment comprises about 0.05% cyclosporin A, an alcohol ethoxylate, and nutmeg oil.

Another embodiment comprises about 0.05% cyclosporin A, an alcohol ethoxylate, and tea tree oil.

Another embodiment comprises about 0.05% cyclosporin A, an alkylphenol ethoxylate, and an oil having a specific gravity between 0.90 and 0.95.

Another embodiment comprises about 0.05% cyclosporin A, an alkylphenol ethoxylate, and almond oil.

Another embodiment comprises about 0.05% cyclosporin A, an alkylphenol ethoxylate, and corn oil.

Another embodiment comprises about 0.05% cyclosporin A, an alkylphenol ethoxylate, and arachis oil.

Another embodiment comprises about 0.05% cyclosporin A, an alkylphenol ethoxylate, and cottonseed oil.

Another embodiment comprises about 0.05% cyclosporin A, an alkylphenol ethoxylate, and safflower oil.

Another embodiment comprises about 0.05% cyclosporin A, an alkylphenol ethoxylate, and maize oil.

Another embodiment comprises about 0.05% cyclosporin A, an alkylphenol ethoxylate, and linseed oil.

Another embodiment comprises about 0.05% cyclosporin A, an alkylphenol ethoxylate, and rapeseed oil.

Another embodiment comprises about 0.05% cyclosporin A, an alkylphenol ethoxylate, and soybean oil.

Another embodiment comprises about 0.05% cyclosporin A, an alkylphenol ethoxylate, and olive oil.

Another embodiment comprises about 0.05% cyclosporin A, an alkylphenol ethoxylate, and caraway oil.

Another embodiment comprises about 0.05% cyclosporin A, an alkylphenol ethoxylate, and rosemary oil.

Another embodiment comprises about 0.05% cyclosporin A, an alkylphenol ethoxylate, and peanut oil.

Another embodiment comprises about 0.05% cyclosporin A, an alkylphenol ethoxylate, and peppermint oil.

Another embodiment comprises about 0.05% cyclosporin A, an alkylphenol ethoxylate, and sunflower oil.

Another embodiment comprises about 0.05% cyclosporin A, an alkylphenol ethoxylate, and eucalpytus oil.

Another embodiment comprises about 0.05% cyclosporin A, an alkylphenol ethoxylate, and sesame oil.

Another embodiment comprises about 0.05% cyclosporin A, an alkylphenol ethoxylate, and an oil having a specific gravity below 0.9.

Another embodiment comprises about 0.05% cyclosporin A, an alkylphenol ethoxylate, and mineral oil.

Another embodiment comprises about 0.05% cyclosporin A, an alkylphenol ethoxylate, and coriander oil.

Another embodiment comprises about 0.05% cyclosporin A, an alkylphenol ethoxylate, and lavender oil.

Another embodiment comprises about 0.05% cyclosporin A, an alkylphenol ethoxylate, and citronella oil.

Another embodiment comprises about 0.05% cyclosporin A, an alkylphenol ethoxylate, and juniper oil.

Another embodiment comprises about 0.05% cyclosporin A, an alkylphenol ethoxylate, and lemon oil.

Another embodiment comprises about 0.05% cyclosporin A, an alkylphenol ethoxylate, and orange oil.

Another embodiment comprises about 0.05% cyclosporin A, an alkylphenol ethoxylate, and clary sage oil.

Another embodiment comprises about 0.05% cyclosporin A, an alkylphenol ethoxylate, and nutmeg oil.

Another embodiment comprises about 0.05% cyclosporin A, an alkylphenol ethoxylate, and tea tree oil.

Another embodiment comprises about 0.05% cyclosporin A, an alkyl glycoside, and an oil having a specific gravity between 0.90 and 0.95.

Another embodiment comprises about 0.05% cyclosporin A, an alkyl glycoside, and almond oil.

Another embodiment comprises about 0.05% cyclosporin A, an alkyl glycoside, and corn oil.

Another embodiment comprises about 0.05% cyclosporin A, an alkyl glycoside, and arachis oil.

Another embodiment comprises about 0.05% cyclosporin A, an alkyl glycoside, and cottonseed oil.

Another embodiment comprises about 0.05% cyclosporin A, an alkyl glycoside, and safflower oil.

Another embodiment comprises about 0.05% cyclosporin A, an alkyl glycoside, and maize oil.

Another embodiment comprises about 0.05% cyclosporin A, an alkyl glycoside, and linseed oil.

Another embodiment comprises about 0.05% cyclosporin A, an alkyl glycoside, and rapeseed oil.

Another embodiment comprises about 0.05% cyclosporin A, an alkyl glycoside, and soybean oil.

Another embodiment comprises about 0.05% cyclosporin A, an alkyl glycoside, and olive oil.

Another embodiment comprises about 0.05% cyclosporin A, an alkyl glycoside, and caraway oil.

Another embodiment comprises about 0.05% cyclosporin A, an alkyl glycoside, and rosemary oil.

Another embodiment comprises about 0.05% cyclosporin A, an alkyl glycoside, and peanut oil.

Another embodiment comprises about 0.05% cyclosporin A, an alkyl glycoside, and peppermint oil.

Another embodiment comprises about 0.05% cyclosporin A, an alkyl glycoside, and sunflower oil.

Another embodiment comprises about 0.05% cyclosporin A, an alkyl glycoside, and eucalpytus oil.

Another embodiment comprises about 0.05% cyclosporin A, an alkyl glycoside, and sesame oil.

Another embodiment comprises about 0.05% cyclosporin A, an alkyl glycoside, and an oil having a specific gravity below 0.9.

Another embodiment comprises about 0.05% cyclosporin A, an alkyl glycoside, and mineral oil.

Another embodiment comprises about 0.05% cyclosporin A, an alkyl glycoside, and coriander oil.

Another embodiment comprises about 0.05% cyclosporin A, an alkyl glycoside, and lavender oil.

Another embodiment comprises about 0.05% cyclosporin A, an alkyl glycoside, and citronella oil.

Another embodiment comprises about 0.05% cyclosporin A, an alkyl glycoside, and juniper oil.

Another embodiment comprises about 0.05% cyclosporin A, an alkyl glycoside, and lemon oil.

Another embodiment comprises about 0.05% cyclosporin A, an alkyl glycoside, and orange oil.

Another embodiment comprises about 0.05% cyclosporin A, an alkyl glycoside, and clary sage oil.

Another embodiment comprises about 0.05% cyclosporin A, an alkyl glycoside, and nutmeg oil.

Another embodiment comprises about 0.05% cyclosporin A, an alkyl glycoside, and tea tree oil.

Another embodiment comprises about 0.05% cyclosporin A, alkyl polyglycoside, and an oil having a specific gravity between 0.90 and 0.95.

Another embodiment comprises about 0.05% cyclosporin A, alkyl polyglycoside, and almond oil.

Another embodiment comprises about 0.05% cyclosporin A, alkyl polyglycoside, and corn oil.

Another embodiment comprises about 0.05% cyclosporin A, alkyl polyglycoside, and arachis oil.

Another embodiment comprises about 0.05% cyclosporin A, alkyl polyglycoside, and cottonseed oil.

Another embodiment comprises about 0.05% cyclosporin A, alkyl polyglycoside, and safflower oil.

Another embodiment comprises about 0.05% cyclosporin A, alkyl polyglycoside, and maize oil.

Another embodiment comprises about 0.05% cyclosporin A, alkyl polyglycoside, and linseed oil.

Another embodiment comprises about 0.05% cyclosporin A, alkyl polyglycoside, and rapeseed oil.

Another embodiment comprises about 0.05% cyclosporin A, alkyl polyglycoside, and soybean oil.
Another embodiment comprises about 0.05% cyclosporin A, alkyl polyglycoside, and olive oil.
Another embodiment comprises about 0.05% cyclosporin A, alkyl polyglycoside, and caraway oil.
Another embodiment comprises about 0.05% cyclosporin A, alkyl polyglycoside, and rosemary oil.
Another embodiment comprises about 0.05% cyclosporin A, alkyl polyglycoside, and peanut oil.
Another embodiment comprises about 0.05% cyclosporin A, alkyl polyglycoside, and peppermint oil.
Another embodiment comprises about 0.05% cyclosporin A, alkyl polyglycoside, and sunflower oil.
Another embodiment comprises about 0.05% cyclosporin A, alkyl polyglycoside, and eucalpytus oil.
Another embodiment comprises about 0.05% cyclosporin A, alkyl polyglycoside, and sesame oil.
Another embodiment comprises about 0.05% cyclosporin A, alkyl polyglycoside, and an oil having a specific gravity below 0.9.
Another embodiment comprises about 0.05% cyclosporin A, alkyl polyglycoside, and mineral oil.
Another embodiment comprises about 0.05% cyclosporin A, alkyl polyglycoside, and coriander oil.
Another embodiment comprises about 0.05% cyclosporin A, alkyl polyglycoside, and lavender oil.
Another embodiment comprises about 0.05% cyclosporin A, alkyl polyglycoside, and citronella oil.
Another embodiment comprises about 0.05% cyclosporin A, alkyl polyglycoside, and juniper oil.
Another embodiment comprises about 0.05% cyclosporin A, alkyl polyglycoside, and lemon oil.
Another embodiment comprises about 0.05% cyclosporin A, alkyl polyglycoside, and orange oil.
Another embodiment comprises about 0.05% cyclosporin A, alkyl polyglycoside, and clary sage oil.
Another embodiment comprises about 0.05% cyclosporin A, alkyl polyglycoside, and nutmeg oil.
Another embodiment comprises about 0.05% cyclosporin A, alkyl polyglycoside, and tea tree oil.
Another embodiment comprises about 0.05% cyclosporin A, a fatty alcohol, and an oil having a specific gravity between 0.90 and 0.95.
Another embodiment comprises about 0.05% cyclosporin A, a fatty alcohol, and almond oil.
Another embodiment comprises about 0.05% cyclosporin A, a fatty alcohol, and corn oil.
Another embodiment comprises about 0.05% cyclosporin A, a fatty alcohol, and arachis oil.
Another embodiment comprises about 0.05% cyclosporin A, a fatty alcohol, and cottonseed oil.
Another embodiment comprises about 0.05% cyclosporin A, a fatty alcohol, and safflower oil.
Another embodiment comprises about 0.05% cyclosporin A, a fatty alcohol, and maize oil.
Another embodiment comprises about 0.05% cyclosporin A, a fatty alcohol, and linseed oil.
Another embodiment comprises about 0.05% cyclosporin A, a fatty alcohol, and rapeseed oil.
Another embodiment comprises about 0.05% cyclosporin A, a fatty alcohol, and soybean oil.
Another embodiment comprises about 0.05% cyclosporin A, a fatty alcohol, and olive oil.
Another embodiment comprises about 0.05% cyclosporin A, a fatty alcohol, and caraway oil.
Another embodiment comprises about 0.05% cyclosporin A, a fatty alcohol, and rosemary oil.
Another embodiment comprises about 0.05% cyclosporin A, a fatty alcohol, and peanut oil.
Another embodiment comprises about 0.05% cyclosporin A, a fatty alcohol, and peppermint oil.
Another embodiment comprises about 0.05% cyclosporin A, a fatty alcohol, and sunflower oil.
Another embodiment comprises about 0.05% cyclosporin A, a fatty alcohol, and eucalpytus oil.
Another embodiment comprises about 0.05% cyclosporin A, a fatty alcohol, and sesame oil.
Another embodiment comprises about 0.05% cyclosporin A, a fatty alcohol, and an oil having a specific gravity below 0.9.
Another embodiment comprises about 0.05% cyclosporin A, a fatty alcohol, and mineral oil.
Another embodiment comprises about 0.05% cyclosporin A, a fatty alcohol, and coriander oil.
Another embodiment comprises about 0.05% cyclosporin A, a fatty alcohol, and lavender oil.
Another embodiment comprises about 0.05% cyclosporin A, a fatty alcohol, and citronella oil.
Another embodiment comprises about 0.05% cyclosporin A, a fatty alcohol, and juniper oil.
Another embodiment comprises about 0.05% cyclosporin A, a fatty alcohol, and lemon oil.
Another embodiment comprises about 0.05% cyclosporin A, a fatty alcohol, and orange oil.
Another embodiment comprises about 0.05% cyclosporin A, a fatty alcohol, and clary sage oil.
Another embodiment comprises about 0.05% cyclosporin A, a fatty alcohol, and nutmeg oil.
Another embodiment comprises about 0.05% cyclosporin A, a fatty alcohol, and tea tree oil.
Another embodiment comprises about 0.05% cyclosporin A, hydroxypropylmethyl cellulose, and an oil having a specific gravity between 0.90 and 0.95.
Another embodiment comprises about 0.05% cyclosporin A, hydroxypropylmethyl cellulose, and almond oil.
Another embodiment comprises about 0.05% cyclosporin A, hydroxypropylmethyl cellulose, and corn oil.
Another embodiment comprises about 0.05% cyclosporin A, hydroxypropylmethyl cellulose, and arachis oil.
Another embodiment comprises about 0.05% cyclosporin A, hydroxypropylmethyl cellulose, and cottonseed oil.
Another embodiment comprises about 0.05% cyclosporin A, hydroxypropylmethyl cellulose, and safflower oil.
Another embodiment comprises about 0.05% cyclosporin A, hydroxypropylmethyl cellulose, and maize oil.
Another embodiment comprises about 0.05% cyclosporin A, hydroxypropylmethyl cellulose, and linseed oil.
Another embodiment comprises about 0.05% cyclosporin A, hydroxypropylmethyl cellulose, and rapeseed oil.
Another embodiment comprises about 0.05% cyclosporin A, hydroxypropylmethyl cellulose, and soybean oil.
Another embodiment comprises about 0.05% cyclosporin A, hydroxypropylmethyl cellulose, and olive oil.
Another embodiment comprises about 0.05% cyclosporin A, hydroxypropylmethyl cellulose, and caraway oil.
Another embodiment comprises about 0.05% cyclosporin A, hydroxypropylmethyl cellulose, and rosemary oil.
Another embodiment comprises about 0.05% cyclosporin A, hydroxypropylmethyl cellulose, and peanut oil.
Another embodiment comprises about 0.05% cyclosporin A, hydroxypropylmethyl cellulose, and peppermint oil.

Another embodiment comprises about 0.05% cyclosporin A, hydroxypropylmethyl cellulose, and sunflower oil.

Another embodiment comprises about 0.05% cyclosporin A, hydroxypropylmethyl cellulose, and eucalpytus oil.

Another embodiment comprises about 0.05% cyclosporin A, hydroxypropylmethyl cellulose, and sesame oil.

Another embodiment comprises about 0.05% cyclosporin A, hydroxypropylmethyl cellulose, and an oil having a specific gravity below 0.9.

Another embodiment comprises about 0.05% cyclosporin A, hydroxypropylmethyl cellulose, and mineral oil.

Another embodiment comprises about 0.05% cyclosporin A, hydroxypropylmethyl cellulose, and coriander oil.

Another embodiment comprises about 0.05% cyclosporin A, hydroxypropylmethyl cellulose, and lavender oil.

Another embodiment comprises about 0.05% cyclosporin A, hydroxypropylmethyl cellulose, and citronella oil.

Another embodiment comprises about 0.05% cyclosporin A, hydroxypropylmethyl cellulose, and juniper oil.

Another embodiment comprises about 0.05% cyclosporin A, hydroxypropylmethyl cellulose, and lemon oil.

Another embodiment comprises about 0.05% cyclosporin A, hydroxypropylmethyl cellulose, and orange oil.

Another embodiment comprises about 0.05% cyclosporin A, hydroxypropylmethyl cellulose, and clary sage oil.

Another embodiment comprises about 0.05% cyclosporin A, hydroxypropylmethyl cellulose, and nutmeg oil.

Another embodiment comprises about 0.05% cyclosporin A, hydroxypropylmethyl cellulose, and tea tree oil.

Another embodiment comprises about 0.05% cyclosporin A, carboxymethyl cellulose, and an oil having a specific gravity between 0.90 and 0.95.

Another embodiment comprises about 0.05% cyclosporin A, carboxymethyl cellulose, and almond oil.

Another embodiment comprises about 0.05% cyclosporin A, carboxymethyl cellulose, and corn oil.

Another embodiment comprises about 0.05% cyclosporin A, carboxymethyl cellulose, and arachis oil.

Another embodiment comprises about 0.05% cyclosporin A, carboxymethyl cellulose, and cottonseed oil.

Another embodiment comprises about 0.05% cyclosporin A, carboxymethyl cellulose, and safflower oil.

Another embodiment comprises about 0.05% cyclosporin A, carboxymethyl cellulose, and maize oil.

Another embodiment comprises about 0.05% cyclosporin A, carboxymethyl cellulose, and linseed oil.

Another embodiment comprises about 0.05% cyclosporin A, carboxymethyl cellulose, and rapeseed oil.

Another embodiment comprises about 0.05% cyclosporin A, carboxymethyl cellulose, and soybean oil.

Another embodiment comprises about 0.05% cyclosporin A, carboxymethyl cellulose, and olive oil.

Another embodiment comprises about 0.05% cyclosporin A, carboxymethyl cellulose, and caraway oil.

Another embodiment comprises about 0.05% cyclosporin A, carboxymethyl cellulose, and rosemary oil.

Another embodiment comprises about 0.05% cyclosporin A, carboxymethyl cellulose, and peanut oil.

Another embodiment comprises about 0.05% cyclosporin A, carboxymethyl cellulose, and peppermint oil.

Another embodiment comprises about 0.05% cyclosporin A, carboxymethyl cellulose, and sunflower oil.

Another embodiment comprises about 0.05% cyclosporin A, carboxymethyl cellulose, and eucalpytus oil.

Another embodiment comprises about 0.05% cyclosporin A, carboxymethyl cellulose, and sesame oil.

Another embodiment comprises about 0.05% cyclosporin A, carboxymethyl cellulose, and an oil having a specific gravity below 0.9.

Another embodiment comprises about 0.05% cyclosporin A, carboxymethyl cellulose, and mineral oil.

Another embodiment comprises about 0.05% cyclosporin A, carboxymethyl cellulose, and coriander oil.

Another embodiment comprises about 0.05% cyclosporin A, carboxymethyl cellulose, and lavender oil.

Another embodiment comprises about 0.05% cyclosporin A, carboxymethyl cellulose, and citronella oil.

Another embodiment comprises about 0.05% cyclosporin A, carboxymethyl cellulose, and juniper oil.

Another embodiment comprises about 0.05% cyclosporin A, carboxymethyl cellulose, and lemon oil.

Another embodiment comprises about 0.05% cyclosporin A, carboxymethyl cellulose, and orange oil.

Another embodiment comprises about 0.05% cyclosporin A, carboxymethyl cellulose, and clary sage oil.

Another embodiment comprises about 0.05% cyclosporin A, carboxymethyl cellulose, and nutmeg oil.

Another embodiment comprises about 0.05% cyclosporin A, carboxymethyl cellulose, and tea tree oil.

Another embodiment comprises about 0.05% cyclosporin A, a polyacrylic acid, and an oil having a specific gravity between 0.90 and 0.95.

Another embodiment comprises about 0.05% cyclosporin A, a polyacrylic acid, and almond oil.

Another embodiment comprises about 0.05% cyclosporin A, a polyacrylic acid, and corn oil.

Another embodiment comprises about 0.05% cyclosporin A, a polyacrylic acid, and arachis oil.

Another embodiment comprises about 0.05% cyclosporin A, a polyacrylic acid, and cottonseed oil.

Another embodiment comprises about 0.05% cyclosporin A, a polyacrylic acid, and safflower oil.

Another embodiment comprises about 0.05% cyclosporin A, a polyacrylic acid, and maize oil.

Another embodiment comprises about 0.05% cyclosporin A, a polyacrylic acid, and linseed oil.

Another embodiment comprises about 0.05% cyclosporin A, a polyacrylic acid, and rapeseed oil.

Another embodiment comprises about 0.05% cyclosporin A, a polyacrylic acid, and soybean oil.

Another embodiment comprises about 0.05% cyclosporin A, a polyacrylic acid, and olive oil.

Another embodiment comprises about 0.05% cyclosporin A, a polyacrylic acid, and caraway oil.

Another embodiment comprises about 0.05% cyclosporin A, a polyacrylic acid, and rosemary oil.

Another embodiment comprises about 0.05% cyclosporin A, a polyacrylic acid, and peanut oil.

Another embodiment comprises about 0.05% cyclosporin A, a polyacrylic acid, and peppermint oil.

Another embodiment comprises about 0.05% cyclosporin A, a polyacrylic acid, and sunflower oil.

Another embodiment comprises about 0.05% cyclosporin A, a polyacrylic acid, and eucalpytus oil.

Another embodiment comprises about 0.05% cyclosporin A, a polyacrylic acid, and sesame oil.

Another embodiment comprises about 0.05% cyclosporin A, a polyacrylic acid, and an oil having a specific gravity below 0.9.

Another embodiment comprises about 0.05% cyclosporin A, a polyacrylic acid, and mineral oil.

Another embodiment comprises about 0.05% cyclosporin A, a polyacrylic acid, and coriander oil.

Another embodiment comprises about 0.05% cyclosporin A, a polyacrylic acid, and lavender oil.

Another embodiment comprises about 0.05% cyclosporin A, a polyacrylic acid, and citronella oil.

Another embodiment comprises about 0.05% cyclosporin A, a polyacrylic acid, and juniper oil.

Another embodiment comprises about 0.05% cyclosporin A, a polyacrylic acid, and lemon oil.

Another embodiment comprises about 0.05% cyclosporin A, a polyacrylic acid, and orange oil.

Another embodiment comprises about 0.05% cyclosporin A, a polyacrylic acid, and clary sage oil.

Another embodiment comprises about 0.05% cyclosporin A, a polyacrylic acid, and nutmeg oil.

Another embodiment comprises about 0.05% cyclosporin A, a polyacrylic acid, and tea tree oil.

Another embodiment comprises about 0.05% cyclosporin A, a Carbomer, and an oil having a specific gravity between 0.90 and 0.95.

Another embodiment comprises about 0.05% cyclosporin A, a Carbomer, and almond oil.

Another embodiment comprises about 0.05% cyclosporin A, a Carbomer, and corn oil.

Another embodiment comprises about 0.05% cyclosporin A, a Carbomer, and arachis oil.

Another embodiment comprises about 0.05% cyclosporin A, a Carbomer, and cottonseed oil.

Another embodiment comprises about 0.05% cyclosporin A, a Carbomer, and safflower oil.

Another embodiment comprises about 0.05% cyclosporin A, a Carbomer, and maize oil.

Another embodiment comprises about 0.05% cyclosporin A, a Carbomer, and linseed oil.

Another embodiment comprises about 0.05% cyclosporin A, a Carbomer, and rapeseed oil.

Another embodiment comprises about 0.05% cyclosporin A, a Carbomer, and soybean oil.

Another embodiment comprises about 0.05% cyclosporin A, a Carbomer, and olive oil.

Another embodiment comprises about 0.05% cyclosporin A, a Carbomer, and caraway oil.

Another embodiment comprises about 0.05% cyclosporin A, a Carbomer, and rosemary oil.

Another embodiment comprises about 0.05% cyclosporin A, a Carbomer, and peanut oil.

Another embodiment comprises about 0.05% cyclosporin A, a Carbomer, and peppermint oil.

Another embodiment comprises about 0.05% cyclosporin A, a Carbomer, and sunflower oil.

Another embodiment comprises about 0.05% cyclosporin A, a Carbomer, and eucalpytus oil.

Another embodiment comprises about 0.05% cyclosporin A, a Carbomer, and sesame oil.

Another embodiment comprises about 0.05% cyclosporin A, a Carbomer, and an oil having a specific gravity below 0.9.

Another embodiment comprises about 0.05% cyclosporin A, a Carbomer, and mineral oil.

Another embodiment comprises about 0.05% cyclosporin A, a Carbomer, and coriander oil.

Another embodiment comprises about 0.05% cyclosporin A, a Carbomer, and lavender oil.

Another embodiment comprises about 0.05% cyclosporin A, a Carbomer, and citronella oil.

Another embodiment comprises about 0.05% cyclosporin A, a Carbomer, and juniper oil.

Another embodiment comprises about 0.05% cyclosporin A, a Carbomer, and lemon oil.

Another embodiment comprises about 0.05% cyclosporin A, a Carbomer, and orange oil.

Another embodiment comprises about 0.05% cyclosporin A, a Carbomer, and clary sage oil.

Another embodiment comprises about 0.05% cyclosporin A, a Carbomer, and nutmeg oil.

Another embodiment comprises about 0.05% cyclosporin A, a Carbomer, and tea tree oil.

Another embodiment comprises about 0.05% cyclosporin A, a phosphalipid, and an oil having a specific gravity between 0.90 and 0.95.

Another embodiment comprises about 0.05% cyclosporin A, a phosphalipid, and almond oil.

Another embodiment comprises about 0.05% cyclosporin A, a phosphalipid, and corn oil.

Another embodiment comprises about 0.05% cyclosporin A, a phosphalipid, and arachis oil.

Another embodiment comprises about 0.05% cyclosporin A, a phosphalipid, and cottonseed oil.

Another embodiment comprises about 0.05% cyclosporin A, a phosphalipid, and safflower oil.

Another embodiment comprises about 0.05% cyclosporin A, a phosphalipid, and maize oil.

Another embodiment comprises about 0.05% cyclosporin A, a phosphalipid, and linseed oil.

Another embodiment comprises about 0.05% cyclosporin A, a phosphalipid, and rapeseed oil.

Another embodiment comprises about 0.05% cyclosporin A, a phosphalipid, and soybean oil.

Another embodiment comprises about 0.05% cyclosporin A, a phosphalipid, and olive oil.

Another embodiment comprises about 0.05% cyclosporin A, a phosphalipid, and caraway oil.

Another embodiment comprises about 0.05% cyclosporin A, a phosphalipid, and rosemary oil.

Another embodiment comprises about 0.05% cyclosporin A, a phosphalipid, and peanut oil.

Another embodiment comprises about 0.05% cyclosporin A, a phosphalipid, and peppermint oil.

Another embodiment comprises about 0.05% cyclosporin A, a phosphalipid, and sunflower oil.

Another embodiment comprises about 0.05% cyclosporin A, a phosphalipid, and eucalpytus oil.

Another embodiment comprises about 0.05% cyclosporin A, a phosphalipid, and sesame oil.

Another embodiment comprises about 0.05% cyclosporin A, a phosphalipid, and an oil having a specific gravity below 0.9.

Another embodiment comprises about 0.05% cyclosporin A, a phosphalipid, and mineral oil.

Another embodiment comprises about 0.05% cyclosporin A, a phosphalipid, and coriander oil.

Another embodiment comprises about 0.05% cyclosporin A, a phosphalipid, and lavender oil.

Another embodiment comprises about 0.05% cyclosporin A, a phosphalipid, and citronella oil.

Another embodiment comprises about 0.05% cyclosporin A, a phosphalipid, and juniper oil.

Another embodiment comprises about 0.05% cyclosporin A, a phosphalipid, and lemon oil.

Another embodiment comprises about 0.05% cyclosporin A, a phosphalipid, and orange oil.

Another embodiment comprises about 0.05% cyclosporin A, a phosphalipid, and clary sage oil.

Another embodiment comprises about 0.05% cyclosporin A, a phosphalipid, and nutmeg oil.

Another embodiment comprises about 0.05% cyclosporin A, a phosphalipid, and tea tree oil.

Another embodiment comprises about 0.05% cyclosporin A, phosphatidyl chloline, and an oil having a specific gravity between 0.90 and 0.95.

Another embodiment comprises about 0.05% cyclosporin A, phosphatidyl chloline, and almond oil.

Another embodiment comprises about 0.05% cyclosporin A, phosphatidyl chloline, and corn oil.

Another embodiment comprises about 0.05% cyclosporin A, phosphatidyl chloline, and arachis oil.

Another embodiment comprises about 0.05% cyclosporin A, phosphatidyl chloline, and cottonseed oil.

Another embodiment comprises about 0.05% cyclosporin A, phosphatidyl chloline, and safflower oil.

Another embodiment comprises about 0.05% cyclosporin A, phosphatidyl chloline, and maize oil.

Another embodiment comprises about 0.05% cyclosporin A, phosphatidyl chloline, and linseed oil.

Another embodiment comprises about 0.05% cyclosporin A, phosphatidyl chloline, and rapeseed oil.

Another embodiment comprises about 0.05% cyclosporin A, phosphatidyl chloline, and soybean oil.

Another embodiment comprises about 0.05% cyclosporin A, phosphatidyl chloline, and olive oil.

Another embodiment comprises about 0.05% cyclosporin A, phosphatidyl chloline, and caraway oil.

Another embodiment comprises about 0.05% cyclosporin A, phosphatidyl chloline, and rosemary oil.

Another embodiment comprises about 0.05% cyclosporin A, phosphatidyl chloline, and peanut oil.

Another embodiment comprises about 0.05% cyclosporin A, phosphatidyl chloline, and peppermint oil.

Another embodiment comprises about 0.05% cyclosporin A, phosphatidyl chloline, and sunflower oil.

Another embodiment comprises about 0.05% cyclosporin A, phosphatidyl chloline, and eucalpytus oil.

Another embodiment comprises about 0.05% cyclosporin A, phosphatidyl chloline, and sesame oil.

Another embodiment comprises about 0.05% cyclosporin A, phosphatidyl chloline, and an oil having a specific gravity below 0.9.

Another embodiment comprises about 0.05% cyclosporin A, phosphatidyl chloline, and mineral oil.

Another embodiment comprises about 0.05% cyclosporin A, phosphatidyl chloline, and coriander oil.

Another embodiment comprises about 0.05% cyclosporin A, phosphatidyl chloline, and lavender oil.

Another embodiment comprises about 0.05% cyclosporin A, phosphatidyl chloline, and citronella oil.

Another embodiment comprises about 0.05% cyclosporin A, phosphatidyl chloline, and juniper oil.

Another embodiment comprises about 0.05% cyclosporin A, phosphatidyl chloline, and lemon oil.

Another embodiment comprises about 0.05% cyclosporin A, phosphatidyl chloline, and orange oil.

Another embodiment comprises about 0.05% cyclosporin A, phosphatidyl chloline, and clary sage oil.

Another embodiment comprises about 0.05% cyclosporin A, phosphatidyl chloline, and nutmeg oil.

Another embodiment comprises about 0.05% cyclosporin A, phosphatidyl chlorine, and tea tree oil.

Another embodiment comprises about 0.05% cyclosporin A, phosphatidyl serine, and an oil having a specific gravity between 0.90 and 0.95.

Another embodiment comprises about 0.05% cyclosporin A, phosphatidyl serine, and almond oil.

Another embodiment comprises about 0.05% cyclosporin A, phosphatidyl serine, and corn oil.

Another embodiment comprises about 0.05% cyclosporin A, phosphatidyl serine, and arachis oil.

Another embodiment comprises about 0.05% cyclosporin A, phosphatidyl serine, and cottonseed oil.

Another embodiment comprises about 0.05% cyclosporin A, phosphatidyl serine, and safflower oil.

Another embodiment comprises about 0.05% cyclosporin A, phosphatidyl serine, and maize oil.

Another embodiment comprises about 0.05% cyclosporin A, phosphatidyl serine, and linseed oil.

Another embodiment comprises about 0.05% cyclosporin A, phosphatidyl serine, and rapeseed oil.

Another embodiment comprises about 0.05% cyclosporin A, phosphatidyl serine, and soybean oil.

Another embodiment comprises about 0.05% cyclosporin A, phosphatidyl serine, and olive oil.

Another embodiment comprises about 0.05% cyclosporin A, phosphatidyl serine, and caraway oil.

Another embodiment comprises about 0.05% cyclosporin A, phosphatidyl serine, and rosemary oil.

Another embodiment comprises about 0.05% cyclosporin A, phosphatidyl serine, and peanut oil.

Another embodiment comprises about 0.05% cyclosporin A, phosphatidyl serine, and peppermint oil.

Another embodiment comprises about 0.05% cyclosporin A, phosphatidyl serine, and sunflower oil.

Another embodiment comprises about 0.05% cyclosporin A, phosphatidyl serine, and eucalpytus oil.

Another embodiment comprises about 0.05% cyclosporin A, phosphatidyl serine, and sesame oil.

Another embodiment comprises about 0.05% cyclosporin A, phosphatidyl serine, and an oil having a specific gravity below 0.9.

Another embodiment comprises about 0.05% cyclosporin A, phosphatidyl serine, and mineral oil.

Another embodiment comprises about 0.05% cyclosporin A, phosphatidyl serine, and coriander oil.

Another embodiment comprises about 0.05% cyclosporin A, phosphatidyl serine, and lavender oil.

Another embodiment comprises about 0.05% cyclosporin A, phosphatidyl serine, and citronella oil.

Another embodiment comprises about 0.05% cyclosporin A, phosphatidyl serine, and juniper oil.

Another embodiment comprises about 0.05% cyclosporin A, phosphatidyl serine, and lemon oil.

Another embodiment comprises about 0.05% cyclosporin A, phosphatidyl serine, and orange oil.

Another embodiment comprises about 0.05% cyclosporin A, phosphatidyl serine, and clary sage oil.

Another embodiment comprises about 0.05% cyclosporin A, phosphatidyl serine, and nutmeg oil.

Another embodiment comprises about 0.05% cyclosporin A, phosphatidyl serine, and tea tree oil.

The present compositions are stable emulsions of cyclosporin.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

In accordance with the present invention, the emulsions can be further stabilized using a polyelectrolyte, or polyelectrolytes if more than one, from the family of cross-linked polyacrylates, such as carbomers and Pemulen®.

Pemulen® is a registered trademark of B. F. Goodrich for polymeric emulsifiers and commercially available from B. F. Goodrich Company, Specialty Polymers & Chemicals Division, Cleveland, Ohio. Pemulens are Acrylates/C10-30 Alkyl Acrylate Cross-Polymers. They are high molecular weight co-polymers of acrylic acid and a long chain alkyl methacrylate cross-linked with allyl ethers of pentaerythritol. They contain not less than 52.0 percent and not more than 62.0 percent of carboxylic acid groups. The viscosity of a neutralized 1.0 percent aqueous dispersion is between 9,500 and 26,500 centipoises.

In addition, the tonicity of the emulsions can be further adjusted using glycerine, mannitol, or sorbitol if desired. The pH of the emulsions can be adjusted in a conventional manner using sodium hydroxide to a near physiological pH level and while buffering agents are not required, suitable buffers may include phosphates, citrates, acetates and borates.

Some useful examples are shown in the table below.

| Ingredients | 1 | 2 |
|---|---|---|
| Cyclosporine A | 0.02 | 0.05 |
| Lavender oil | | 1.00 |
| Olive oil | 1.00 | |
| Polysorbate-80 | | 0.60 |
| Brij78 | 0.80 | |
| Desonic 9D | | 0.40 |
| Glycerin | 1.20 | 2.00 |
| CMC | 0.50 | |
| Purified Water | QS | QS |
| Sodium Hydroxide | pH adj | pH adj |
| pH | 7.6 | 5.9 |

Although there has been hereinabove described a particular pharmaceutical composition in the form of a nonirritating emulsion for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A composition comprising from about 0.001% to about 0.4% cyclosporin A, a surfactant, and almond oil, wherein said composition is an ophthalmically acceptable emulsion.

2. The composition of claim 1 comprising from about 0.005% to about 0.05% cyclosporin A.

3. The composition of claim 2 comprising about 0.05% cyclosporin A.

* * * * *

UNITED STATES PATENT AND TRADEMARK OFFICE
CERTIFICATE OF CORRECTION

PATENT NO.       : 7,297,679 B2
APPLICATION NO.  : 11/181178
DATED            : November 20, 2007
INVENTOR(S)      : Chang et al.

It is certified that error appears in the above-identified patent and that said Letters Patent is hereby corrected as shown below:

In column 2, line 17, delete "eucalpytus" and insert -- eucalyptus --, therefor.

In column 3, line 28, delete "eucalpytus" and insert -- eucalyptus --, therefor.

In column 4, line 20, delete "eucalpytus" and insert -- eucalyptus --, therefor.

In column 5, line 12, delete "eucalpytus" and insert -- eucalyptus --, therefor.

In column 6, line 4, delete "eucalpytus" and insert -- eucalyptus --, therefor.

In column 6, line 63, delete "eucalpytus" and insert -- eucalyptus --, therefor.

In column 7, line 55, delete "eucalpytus" and insert -- eucalyptus --, therefor.

In column 8, line 47, delete "eucalpytus" and insert -- eucalyptus --, therefor.

In column 9, line 39, delete "eucalpytus" and insert -- eucalyptus --, therefor.

In column 10, line 32, delete "eucalpytus" and insert -- eucalyptus --, therefor.

In column 11, line 24, delete "eucalpytus" and insert -- eucalyptus --, therefor.

In column 12, line 18, delete "eucalpytus" and insert -- eucalyptus --, therefor.

In column 13, line 10, delete "eucalpytus" and insert -- eucalyptus --, therefor.

In column 14, line 2, delete "eucalpytus" and insert -- eucalyptus --, therefor.

In column 14, line 61, delete "eucalpytus" and insert -- eucalyptus --, therefor.

In column 16, line 3, delete "eucalpytus" and insert -- eucalyptus --, therefor.

In column 17, line 8, delete "eucalpytus" and insert -- eucalyptus --, therefor.

In column 17, line 67, delete "eucalpytus" and insert -- eucalyptus --, therefor.

In column 18, line 61, delete "eucalpytus" and insert -- eucalyptus --, therefor.

In column 19, line 54, delete "eucalpytus" and insert -- eucalyptus --, therefor.

UNITED STATES PATENT AND TRADEMARK OFFICE
CERTIFICATE OF CORRECTION

PATENT NO. : 7,297,679 B2
APPLICATION NO. : 11/181178
DATED : November 20, 2007
INVENTOR(S) : Chang et al.

It is certified that error appears in the above-identified patent and that said Letters Patent is hereby corrected as shown below:

In column 20, line 47, delete "eucalpytus" and insert -- eucalyptus --, therefor.

In column 21, line 39, delete "eucalpytus" and insert -- eucalyptus --, therefor.

In column 22, line 32, delete "eucalpytus" and insert -- eucalyptus --, therefor.

In column 23, line 26, delete "eucalpytus" and insert -- eucalyptus --, therefor.

In column 24, line 18, delete "eucalpytus" and insert -- eucalyptus --, therefor.

In column 24, lines 43-44, delete "phosphalipid" and insert -- phospholipid --, therefor.

In column 24, lines 46-47, delete "phosphalipid" and insert -- phospholipid --, therefor.

In column 24, lines 48-49, delete "phosphalipid" and insert -- phospholipid --, therefor.

In column 24, lines 50-51, delete "phosphalipid" and insert -- phospholipid --, therefor.

In column 24, lines 52-53, delete "phosphalipid" and insert -- phospholipid --, therefor.

In column 24, lines 54-55, delete "phosphalipid" and insert -- phospholipid --, therefor.

In column 24, lines 56-57, delete "phosphalipid" and insert -- phospholipid --, therefor.

In column 24, lines 58-59, delete "phosphalipid" and insert -- phospholipid --, therefor.

In column 24, lines 60-61, delete "phosphalipid" and insert -- phospholipid --, therefor.

In column 24, lines 62-63, delete "phosphalipid" and insert -- phospholipid --, therefor.

In column 24, lines 64-65, delete "phosphalipid" and insert -- phospholipid --, therefor.

In column 24, lines 66-67, delete "phosphalipid" and insert -- phospholipid --, therefor.

In column 25, lines 1-2, delete "phosphalipid" and insert -- phospholipid --, therefor.

In column 25, lines 3-4, delete "phosphalipid" and insert -- phospholipid --, therefor.

In column 25, lines 5-6, delete "phosphalipid" and insert -- phospholipid --, therefor.

UNITED STATES PATENT AND TRADEMARK OFFICE
CERTIFICATE OF CORRECTION

PATENT NO. : 7,297,679 B2
APPLICATION NO. : 11/181178
DATED : November 20, 2007
INVENTOR(S) : Chang et al.

It is certified that error appears in the above-identified patent and that said Letters Patent is hereby corrected as shown below:

In column 25, lines 7-8, delete "phosphalipid" and insert -- phospholipid --, therefor.

In column 25, lines 9-10, delete "phosphalipid" and insert -- phospholipid --, therefor.

In column 25, line 10, delete "eucalpytus" and insert -- eucalyptus --, therefor.

In column 25, lines 11-12, delete "phosphalipid" and insert -- phospholipid --, therefor.

In column 25, lines 13-14, delete "phosphalipid" and insert -- phospholipid --, therefor.

In column 25, lines 15-16, delete "phosphalipid" and insert -- phospholipid --, therefor.

In column 25, lines 17-18, delete "phosphalipid" and insert -- phospholipid --, therefor.

In column 25, lines 19-20, delete "phosphalipid" and insert -- phospholipid --, therefor.

In column 25, lines 21-22, delete "phosphalipid" and insert -- phospholipid --, therefor.

In column 25, lines 23-24, delete "phosphalipid" and insert -- phospholipid --, therefor.

In column 25, lines 25-26, delete "phosphalipid" and insert -- phospholipid --, therefor.

In column 25, lines 27-28, delete "phosphalipid" and insert -- phospholipid --, therefor.

In column 25, lines 29-30, delete "phosphalipid" and insert -- phospholipid --, therefor.

In column 25, lines 31-32, delete "phosphalipid" and insert -- phospholipid --, therefor.

In column 25, lines 33-34, delete "phosphalipid" and insert -- phospholipid --, therefor.

In column 25, line 39, delete "chlorine" and insert -- chloline --, therefor.

In column 25, line 41, delete "chlorine" and insert -- chloline --, therefor.

In column 25, line 43, delete "chlorine" and insert -- chloline --, therefor.

In column 25, line 55, delete "chlorine" and insert -- chloline --, therefor.

UNITED STATES PATENT AND TRADEMARK OFFICE
CERTIFICATE OF CORRECTION

| | |
|---|---|
| PATENT NO. | : 7,297,679 B2 |
| APPLICATION NO. | : 11/181178 |
| DATED | : November 20, 2007 |
| INVENTOR(S) | : Chang et al. |

It is certified that error appears in the above-identified patent and that said Letters Patent is hereby corrected as shown below:

In column 26, line 2, delete "eucalpytus" and insert -- eucalyptus --, therefor.

In column 26, line 19, delete "chlorine" and insert -- chloline --, therefor.

In column 26, line 23, delete "chlorine" and insert -- chloline --, therefor.

In column 26, line 25, delete "chlorine" and insert -- chloline --, therefor.

In column 26, line 27, delete "chlorine" and insert -- chloline --, therefor.

In column 26, line 62, delete "eucalpytus" and insert -- eucalyptus --, therefor.

In column 27, line 64, delete "eucalpytus" and insert -- eucalyptus --, therefor.

In column 29, line 2, delete "eucalpytus" and insert -- eucalyptus --, therefor.

In column 30, line 8, delete "eucalpytus" and insert -- eucalyptus --, therefor.

In column 31, line 13, delete "eucalpytus" and insert -- eucalyptus --, therefor.

In column 32, line 18, delete "eucalpytus" and insert -- eucalyptus --, therefor.

In column 33, line 16, delete "eucalpytus" and insert -- eucalyptus --, therefor.

In column 34, lines 22-23, delete "eucalpytus" and insert -- eucalyptus --, therefor.

In column 35, lines 41-42, delete "eucalpytus" and insert -- eucalyptus --, therefor.

In column 36, lines 60-61, delete "eucalpytus" and insert -- eucalyptus --, therefor.

In column 38, line 15, delete "eucalpytus" and insert -- eucalyptus --, therefor.

In column 39, line 28, delete "eucalpytus" and insert -- eucalyptus --, therefor.

In column 40, line 46, delete "eucalpytus" and insert -- eucalyptus --, therefor.

In column 41, line 67, delete "eucalpytus" and insert -- eucalyptus --, therefor.

In column 43, line 21, delete "eucalpytus" and insert -- eucalyptus --, therefor.

UNITED STATES PATENT AND TRADEMARK OFFICE
CERTIFICATE OF CORRECTION

PATENT NO.       : 7,297,679 B2
APPLICATION NO.  : 11/181178
DATED            : November 20, 2007
INVENTOR(S)      : Chang et al.

It is certified that error appears in the above-identified patent and that said Letters Patent is hereby corrected as shown below:

In column 44, line 42, delete "eucalpytus" and insert -- eucalyptus --, therefor.

In column 45, line 64, delete "eucalpytus" and insert -- eucalyptus --, therefor.

In column 47, line 18, delete "eucalpytus" and insert -- eucalyptus --, therefor.

In column 48, lines 38-39, delete "eucalpytus" and insert -- eucalyptus --, therefor.

In column 49, line 61, delete "eucalpytus" and insert -- eucalyptus --, therefor.

In column 51, line 5, delete "eucalpytus" and insert -- eucalyptus --, therefor.

In column 52, line 18, delete "eucalpytus" and insert -- eucalyptus --, therefor.

In column 53, line 40, delete "eucalpytus" and insert -- eucalyptus --, therefor.

In column 54, lines 57-58, delete "eucalpytus" and insert -- eucalyptus --, therefor.

In column 55, line 62, delete "eucalpytus" and insert -- eucalyptus --, therefor.

In column 56, line 22, delete "phosphalipid" and insert -- phospholipid --, therefor.

In column 56, line 61, delete "eucalpytus" and insert -- eucalyptus --, therefor.

In column 56, line 64, delete "phosphalipid" and insert -- phospholipid --, therefor.

In column 56, line 66, delete "phosphalipid" and insert -- phospholipid --, therefor.

In column 57, line 2, delete "phosphalipid" and insert -- phospholipid --, therefor.

In column 57, line 4, delete "phosphalipid" and insert -- phospholipid --, therefor.

In column 57, line 7, delete "phosphalipid" and insert -- phospholipid --, therefor.

In column 57, line 10, delete "phosphalipid" and insert -- phospholipid --, therefor.

In column 57, line 13, delete "phosphalipid" and insert -- phospholipid --, therefor.

In column 57, line 15, delete "phosphalipid" and insert -- phospholipid --, therefor.

UNITED STATES PATENT AND TRADEMARK OFFICE
CERTIFICATE OF CORRECTION

PATENT NO. : 7,297,679 B2
APPLICATION NO. : 11/181178
DATED : November 20, 2007
INVENTOR(S) : Chang et al.

It is certified that error appears in the above-identified patent and that said Letters Patent is hereby corrected as shown below:

In column 57, line 17, delete "phosphalipid" and insert -- phospholipid --, therefor.

In column 57, line 19, delete "phosphalipid" and insert -- phospholipid --, therefor.

In column 57, line 22, delete "phosphalipid" and insert -- phospholipid --, therefor.

In column 57, line 24, delete "phosphalipid" and insert -- phospholipid --, therefor.

In column 57, line 26, delete "chlorine" and insert -- chloline --, therefor.

In column 57, line 36, delete "chlorine" and insert -- chloline --, therefor.

In column 57, line 42, delete "chlorine" and insert -- chloline --, therefor.

In column 57, line 45, delete "chlorine" and insert -- chloline --, therefor.

In column 57, line 48, delete "chlorine" and insert -- chloline --, therefor.

In column 57, line 54, delete "chlorine" and insert -- chloline --, therefor.

In column 57, line 57, delete "chlorine" and insert -- chloline --, therefor.

In column 57, line 63, delete "chlorine" and insert -- chloline --, therefor.

In column 58, line 2, delete "chlorine" and insert -- chloline --, therefor.

In column 58, line 9, delete "eucalpytus" and insert -- eucalyptus --, therefor.

In column 58, line 11, delete "eucalpytus" and insert -- eucalyptus --, therefor.

In column 58, line 14, delete "eucalpytus" and insert -- eucalyptus --, therefor.

In column 58, line 17, delete "chlorine" and insert -- chloline --, therefor.

In column 58, line 20, delete "chlorine" and insert -- chloline --, therefor.

In column 58, line 23, delete "chlorine" and insert -- chloline --, therefor.

In column 58, line 26, delete "chlorine" and insert -- chloline --, therefor.

UNITED STATES PATENT AND TRADEMARK OFFICE
CERTIFICATE OF CORRECTION

PATENT NO.        : 7,297,679 B2
APPLICATION NO.   : 11/181178
DATED             : November 20, 2007
INVENTOR(S)       : Chang et al.

It is certified that error appears in the above-identified patent and that said Letters Patent is hereby corrected as shown below:

In column 58, line 45, delete "chlorine" and insert -- chloline --, therefor.

In column 59, line 30, delete "chlorine" and insert -- chloline --, therefor.

In column 60, line 35, delete "eucalpytus" and insert -- eucalyptus --, therefor.

In column 61, line 28, delete "eucalpytus" and insert -- eucalyptus --, therefor.

In column 62, line 22, delete "eucalpytus" and insert -- eucalyptus --, therefor.

In column 63, line 16, delete "eucalpytus" and insert -- eucalyptus --, therefor.

In column 64, line 10, delete "eucalpytus" and insert -- eucalyptus --, therefor.

In column 65, line 4, delete "eucalpytus" and insert -- eucalyptus --, therefor.

In column 65, line 65, delete "eucalpytus" and insert -- eucalyptus --, therefor.

In column 66, line 58, delete "eucalpytus" and insert -- eucalyptus --, therefor.

In column 67, line 52, delete "eucalpytus" and insert -- eucalyptus --, therefor.

In column 68, line 46, delete "eucalpytus" and insert -- eucalyptus --, therefor.

In column 69, line 39, delete "eucalpytus" and insert -- eucalyptus --, therefor.

In column 70, line 32, delete "eucalpytus" and insert -- eucalyptus --, therefor.

In column 71, line 26, delete "eucalpytus" and insert -- eucalyptus --, therefor.

In column 72, line 20, delete "eucalpytus" and insert -- eucalyptus --, therefor.

In column 73, line 30, delete "eucalpytus" and insert -- eucalyptus --, therefor.

In column 74, line 35, delete "eucalpytus" and insert -- eucalyptus --, therefor.

In column 75, line 28, delete "eucalpytus" and insert -- eucalyptus --, therefor.

UNITED STATES PATENT AND TRADEMARK OFFICE
CERTIFICATE OF CORRECTION

PATENT NO.        : 7,297,679 B2
APPLICATION NO.   : 11/181178
DATED             : November 20, 2007
INVENTOR(S)       : Chang et al.

It is certified that error appears in the above-identified patent and that said Letters Patent is hereby corrected as shown below:

In column 76, line 22, delete "eucalpytus" and insert -- eucalyptus --, therefor.

In column 77, line 16, delete "eucalpytus" and insert -- eucalyptus --, therefor.

In column 78, line 10, delete "eucalpytus" and insert -- eucalyptus --, therefor.

In column 79, line 4, delete "eucalpytus" and insert -- eucalyptus --, therefor.

In column 79, line 65, delete "eucalpytus" and insert -- eucalyptus --, therefor.

In column 80, line 58, delete "eucalpytus" and insert -- eucalyptus --, therefor.

In column 81, line 52, delete "eucalpytus" and insert -- eucalyptus --, therefor.

In column 82, line 12, delete "phosphalipid" and insert -- phospholipid --, therefor.

In column 82, line 15, delete "phosphalipid" and insert -- phospholipid --, therefor.

In column 82, line 17, delete "phosphalipid" and insert -- phospholipid --, therefor.

In column 82, line 19, delete "phosphalipid" and insert -- phospholipid --, therefor.

In column 82, line 21, delete "phosphalipid" and insert -- phospholipid --, therefor.

In column 82, line 23, delete "phosphalipid" and insert -- phospholipid --, therefor.

In column 82, line 25, delete "phosphalipid" and insert -- phospholipid --, therefor.

In column 82, line 27, delete "phosphalipid" and insert -- phospholipid --, therefor.

In column 82, line 29, delete "phosphalipid" and insert -- phospholipid --, therefor.

In column 82, line 31, delete "phosphalipid" and insert -- phospholipid --, therefor.

In column 82, line 33, delete "phosphalipid" and insert -- phospholipid --, therefor.

In column 82, line 35, delete "phosphalipid" and insert -- phospholipid --, therefor.

In column 82, line 37, delete "phosphalipid" and insert -- phospholipid --, therefor.

UNITED STATES PATENT AND TRADEMARK OFFICE
CERTIFICATE OF CORRECTION

PATENT NO.        : 7,297,679 B2
APPLICATION NO.   : 11/181178
DATED             : November 20, 2007
INVENTOR(S)       : Chang et al.

It is certified that error appears in the above-identified patent and that said Letters Patent is hereby corrected as shown below:

In column 82, line 40, delete "phosphalipid" and insert -- phospholipid --, therefor.

In column 82, line 42, delete "phosphalipid" and insert -- phospholipid --, therefor.

In column 82, line 44, delete "phosphalipid" and insert -- phospholipid --, therefor.

In column 82, line 46, delete "phosphalipid" and insert -- phospholipid --, therefor.

In column 82, line 46, delete "eucalpytus" and insert -- eucalyptus --, therefor.

In column 82, line 48, delete "eucalpytus" and insert -- eucalyptus --, therefor.

In column 82, line 50, delete "phosphalipid" and insert -- phospholipid --, therefor.

In column 82, line 53, delete "phosphalipid" and insert -- phospholipid --, therefor.

In column 82, line 55, delete "phosphalipid" and insert -- phospholipid --, therefor.

In column 82, line 57, delete "phosphalipid" and insert -- phospholipid --, therefor.

In column 82, line 59, delete "phosphalipid" and insert -- phospholipid --, therefor.

In column 82, line 61, delete "phosphalipid" and insert -- phospholipid --, therefor.

In column 82, line 63, delete "phosphalipid" and insert -- phospholipid --, therefor.

In column 82, line 65, delete "phosphalipid" and insert -- phospholipid --, therefor.

In column 82, line 67, delete "phosphalipid" and insert -- phospholipid --, therefor.

In column 83, line 2, delete "phosphalipid" and insert -- phospholipid --, therefor.

In column 83, line 4, delete "phosphalipid" and insert -- phospholipid --, therefor.

UNITED STATES PATENT AND TRADEMARK OFFICE
CERTIFICATE OF CORRECTION

PATENT NO. : 7,297,679 B2
APPLICATION NO. : 11/181178
DATED : November 20, 2007
INVENTOR(S) : Chang et al.

It is certified that error appears in the above-identified patent and that said Letters Patent is hereby corrected as shown below:

In column 83, line 39, delete "eucalpytus" and insert -- eucalyptus --, therefor.

In column 83, line 64, delete "chlorine" and insert -- chloline --, therefor.

In column 84, line 32, delete "eucalpytus" and insert -- eucalyptus --, therefor.

Signed and Sealed this

Twenty Second Day of April, 2008

JON W. DUDAS
*Director of the United States Patent and Trademark Office*